US009799837B2

(12) United States Patent
Nagayama et al.

(10) Patent No.: US 9,799,837 B2
(45) Date of Patent: Oct. 24, 2017

(54) IRIDIUM COMPLEX COMPOUND, SOLUTION COMPOSITION CONTAINING THE COMPOUND, ORGANIC ELECTROLUMINESCENT ELEMENT, DISPLAY, AND LIGHTING

(71) Applicant: MITSUBISHI CHEMICAL CORPORATION, Chiyoda-ku (JP)

(72) Inventors: Kazuhiro Nagayama, Kanagawa (JP); Hideji Komatsu, Kanagawa (JP); Akira Migita, Fukuoka (JP); Hideki Gorohmaru, Kanagawa (JP); Koichiro Iida, Kanagawa (JP); Takashi Oya, Kanagawa (JP); Koichi Ishibashi, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 332 days.

(21) Appl. No.: 14/330,442

(22) Filed: Jul. 14, 2014

(65) Prior Publication Data

US 2014/0319505 A1     Oct. 30, 2014

Related U.S. Application Data

(63) Continuation of application No. PCT/JP2013/050333, filed on Jan. 10, 2013.

(30) Foreign Application Priority Data

Jan. 13, 2012  (JP) .................................. 2012-005118
Sep. 14, 2012  (JP) .................................. 2012-202908

(51) Int. Cl.
H01L 51/54    (2006.01)
C09K 11/06    (2006.01)
H01L 51/00    (2006.01)
C07F 15/00    (2006.01)
H01L 51/50    (2006.01)

(52) U.S. Cl.
CPC ...... *H01L 51/0085* (2013.01); *C07F 15/0033* (2013.01); *C09K 11/06* (2013.01); *H01L 51/50* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/185* (2013.01); *H01L 51/005* (2013.01); *H01L 51/5016* (2013.01)

(58) Field of Classification Search
None
See application file for complete search history.

(56) References Cited

U.S. PATENT DOCUMENTS

| | | |
|---|---|---|
| 2005/0116622 A1 | 6/2005 | Lo et al. |
| 2005/0164029 A1 | 7/2005 | Burn et al. |
| 2006/0127696 A1 | 6/2006 | Stossel et al. |
| 2006/0194073 A1 | 8/2006 | Okada |
| 2008/0050604 A1 | 2/2008 | Takahashi et al. |
| 2010/0228022 A1 | 9/2010 | Burn et al. |
| 2010/0252822 A1 | 10/2010 | Takahashi |
| 2012/0068170 A1 | 3/2012 | Pflumm et al. |
| 2012/0175561 A1 | 7/2012 | Franz et al. |
| 2012/0228552 A1 | 9/2012 | Parham et al. |
| 2012/0228554 A1 | 9/2012 | Franz et al. |
| 2012/0238105 A1 | 9/2012 | Anémian et al. |
| 2013/0082209 A1 | 4/2013 | Stoessel et al. |
| 2013/0181174 A1 | 7/2013 | Pan et al. |
| 2014/0048745 A1 | 2/2014 | Anémian et al. |
| 2015/0155502 A1* | 6/2015 | Ishibashi et al. ... C07F 15/0033 257/40 |

FOREIGN PATENT DOCUMENTS

| | | |
|---|---|---|
| GB | 2 415 960 A | 1/2006 |
| JP | 2003-231692 | 8/2003 |
| JP | 2004-292436 | 10/2004 |
| JP | 2005-537320 | 12/2005 |
| JP | 2006-290781 | 10/2006 |
| JP | 2009-176963 | 8/2009 |
| JP | 2011-511821 A | 4/2011 |

(Continued)

OTHER PUBLICATIONS

Combined Chinese Office Action and Search Report dated Apr. 29, 2015 in Patent Application No. 201380005274.3 (with English language translation and English translation of Category of Cited Documents).
International Search Report dated Mar. 26, 2013 in PCT/JP2013/050333 filed on Jan. 10, 2013 (with English translation).
Written Opinion dated Mar. 26, 2013 in PCT/JP2013/050333 filed on Jan. 10, 2013 (with English translation).
Notification of Reasons for Refusal dated Oct. 1, 2013 in Japanese Patent Application No. 2013-530270 (with English translation).
Marc Lepeltier et al., "Synthesis and photophysical properties of bis-cyclometalated iridium(III)-styryl complexes and their saturated analogues", European Journal of Inorganic Chemistry, 2007, 18, pp. 2734-2747.

(Continued)

*Primary Examiner* — Marie R. Yamnitzky
(74) *Attorney, Agent, or Firm* — Oblon, McClelland, Maier & Neustadt, L.L.P.

(57) ABSTRACT

The present invention is to provide an iridium complex compound, which is soluble in an organic solvent, which can be stored for long periods without reprecipitation thereof and which secures a low driving voltage and a high luminescent efficiency of an organic electroluminescent element produced using the compound, to provide an organic electroluminescent element containing the compound and to provide a display and a lighting using the organic electroluminescent element. The present invention relates to the iridium complex compound having a specific chemical structure. Further, the invention also relates to the organic electroluminescent element produced using the compound, which requires a low operating voltage and has a long operating lifetime.

20 Claims, 1 Drawing Sheet

(56) References Cited

FOREIGN PATENT DOCUMENTS

| | | |
|---|---|---|
| JP | 2012-6878 A | 1/2012 |
| JP | 2014-58457 A | 4/2014 |
| WO | WO 2004/026886 A2 | 4/2004 |
| WO | WO 2006/001150 A1 | 1/2006 |
| WO | WO 2009/022594 A1 | 2/2009 |
| WO | WO 2009/034987 A1 | 3/2009 |
| WO | WO 2010/031738 A1 | 3/2010 |
| WO | WO 2011/032626 A1 | 3/2011 |
| WO | WO 2012/038028 A1 | 3/2012 |

OTHER PUBLICATIONS

Marc Lepeltier et al., "Tris-Cyclometalated Iridium(III), Styryl Complexes and Their Saturated . . . Ir(4-Me-ppy)3 Transfer Process", Organomettalics, 2005, 24(24), pp. 6069-6072.

Toshimitsu Tsuzuki et al., "Organic light-emitting diodes using multifunctional phosphorescent dendrimers with iridium-complex core and charge-transporting dendrons", Japanese Journal of Applied Physics, vol. 44, No. 6A, 2005, pp. 4151-4154.

Hyun-shin Lee, et al., "Synthesis and luminescence studies of hydrocarbon-branched tris-cyclometallated iridium(III) complexes", Molecular Crystals and Liquid Crystals, 2010, vol. 520, pp. 60/336-67/343.

L. S. Hung et al., "Enhanced electron injection in organic electroluminescence devices using an Al/LiF electrode", Appl. Phys. Lett. vol. 70, (2), Jan. 1997, pp. 152-154.

Takeo Wakimoto et al., "Organic EL Cells Using Alkaline Metal Compounds as Electron Injection Materials", IEEE Transactions on Electron Devices, vol. 44, No. 8, Aug. 1997, pp. 1245-1248.

"Basic structure of display panel", Organic Electroluminescence Display, OEL Display 1-4, Aug. 20, 2004, pp. 120-139 and 150-153 (cover page) (with partial English translation).

T. Hasegawa et al., "11.3:Novel Electron-Injection Layers for Top-Emission OLEDs", SID 04 Digest, 2004, pp. 154-157.

Office Action dated Nov. 4, 2015 in Chinese Patent Application No. 201380005274.3 (with English language translation).

Combined Office Action and Search Report dated May 20, 2016 in Taiwanese Patent Application No. 102101216 (with English language translation).

Extended European Search Report dated Nov. 5, 2014 in Patent Application No. 13736249.7.

Office Action dated Oct. 18, 2016 in Japanese Patent Application No. 2014-005992 (with unedited computer generated English translation).

Tadashi Yamashita, et al., "Enhanced insulin sensitivity in mice lacking ganglioside GM3", Proceeding of the National Academy of Sciences of the United States of America, vol. 100, No. 6, 2003, pp. 3445-3449 and Cover Page.

Shih-Chun Lo, et al., "The development of phenylethylene dendrons for blue phosphorescent emitters", Journal of Materials Chemistry, vol. 19, 2009, pp. 3213-3227.

S. Salinas, et al., "New iridium cyclometallated complexes with potential application in OLED", Polyhedron, vol. 30, 2011, pp. 2863-2869.

A Decision of Refusal dated Apr. 18, 2017, in Japanese Patent Application No. 2014-005992 (with English Translation).

* cited by examiner

[Fig. 1]
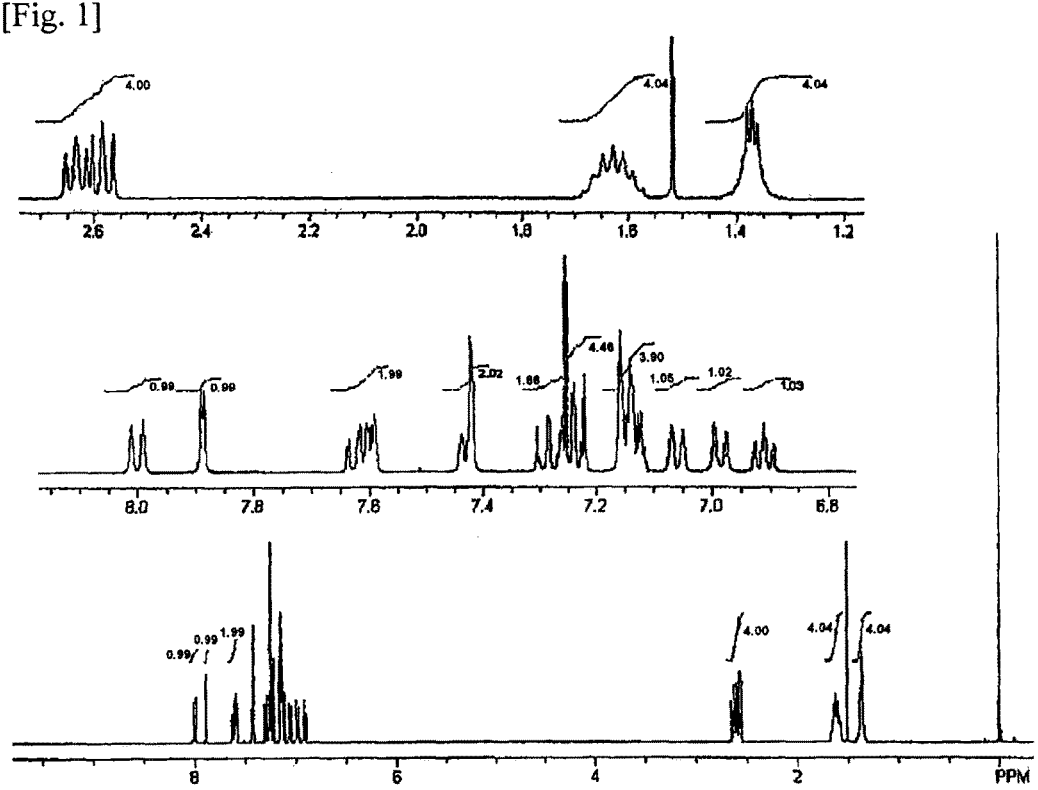
[Fig. 2]
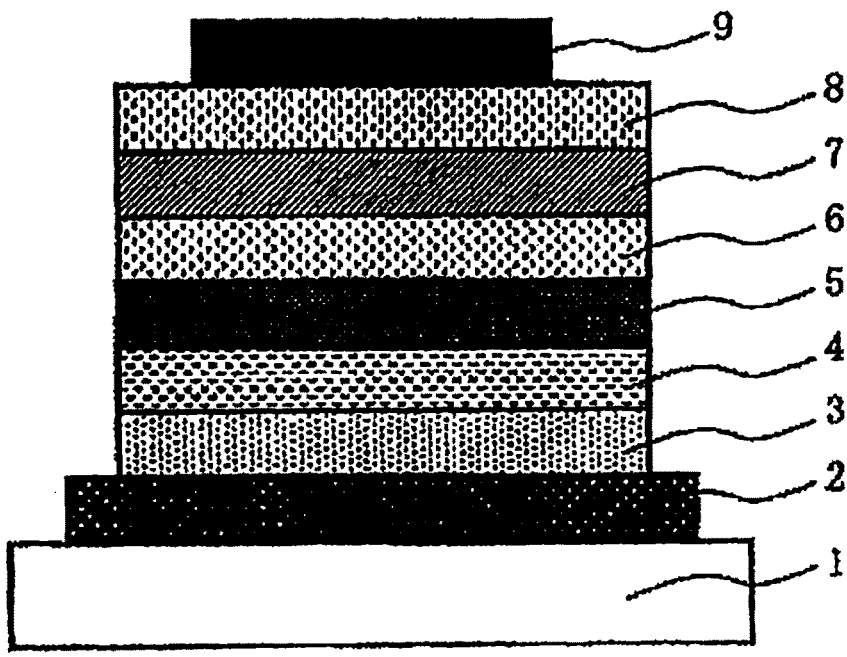

IRIDIUM COMPLEX COMPOUND, SOLUTION COMPOSITION CONTAINING THE COMPOUND, ORGANIC ELECTROLUMINESCENT ELEMENT, DISPLAY, AND LIGHTING

TECHNICAL FIELD

The present invention relates to an iridium complex compound, and especially to an iridium complex compound useful as a material for light-emitting layers in organic electroluminescent elements, a composition containing the compound, an organic electroluminescent element produced using the composition, and a display and a lighting containing the organic electroluminescent element.

TECHNICAL FIELD

Recently, various electronic devices that utilize organic electroluminescent elements (hereinafter these may be referred to as "organic EL elements"), such as organic electroluminescent lighting (organic EL lighting), organic electroluminescent display (organic EL display) and the like are being put into practical use. Organic EL elements need low applied voltage and need little electricity to work, and they are planar light-emitting elements and enable emitting of three primary colors, and therefore their applications to lightings and displays are being much investigated. Accordingly, it is desired to improve the luminescent efficiency of those elements. For improving the luminescent efficiency, for example, it has been proposed to use a phosphorescent material in the light-emitting layer in organic EL elements. As the phosphorescent material, for example, widely known are ortho-metallized iridium complexes such as typically bis(2-phenylpyridinato-N,C2')iridium acetylacetonate ($Ir(ppy)_2(acac)$) and tris(2-phenylpyridinato-N,C2')iridium ($Ir(ppy)_3$).

As a method of manufacturing an organic EL element using such a phosphorescent material, mainly used is a vacuum deposition method. However, in general, since the element is produced by providing multiple layers such as a light-emitting layer, a charge injection layer, a charge transport layer, etc., the vacuum deposition method involves some problems in that the vapor deposition process is complicated and the productivity thereof is low and in addition, it is extremely difficult to enlarge the size of panels of lightings and displays that comprise these elements.

On the other hand, the organic EL element can be produced by providing layers through film formation according to a coating method. As compared with the vacuum vapor deposition method, the coating method can form stable layers with ease and at high yield, and is therefore expected for mass production of displays and lightings and for application to large-size devices.

For film formation according to the coating method, it is necessary that the organic material to be contained in the layer is in a state easily soluble in an organic solvent. In general, the organic solvent to be used is a solvent having a low boiling point and a low viscosity such as, for example, toluene. The ink prepared using such a solvent can readily form a film according to a spin coating method or the like. Also regarding the organic solvent, from the viewpoint of uniformity of coating film and the safety in operation, an organic solvent that is poorly volatile and has a high ignition point such as phenylcyclohexane is more favorably used. Further, the composition that contains an organic material and a solvent must keep a uniform state with no reprecipitation of the organic material during storage therein, or that is, the composition is required to have a sufficiently long pot life.

Regarding production of organic EL elements according to a coating method, there are disclosed an element produced according to a coating method where an iridium complex having $Ir(ppy)_2(acac)$ as the main backbone is dissolved in 1,2-dichloroethane (PTL 1), and an element produced according to a coating method where an iridium complex with a biphenylpyridine ligand having a specific substituent is dissolved in an organic solvent such as toluene or the like (PTL 2).

Though produced according to a coating method, these elements still have room for improvement in that they require a high driving voltage and have a low luminescent efficiency.

Given the circumstances, improvement of an iridium complex effective for driving voltage reduction has been proposed (PTL 3).

CITATION LIST

Patent Literature

PTL 1: JP-A 2006-290781
PTL 2: WO2004/026886
PTL 3: WO2011/032626

SUMMARY OF INVENTION

Technical Problem

However, nothing is referred to relating to the pot life of the composition with an iridium complex compound dissolved therein, and the discussion is still insufficient in point of industrial mass-production.

The present invention has been made in consideration of the above-mentioned problems, and its one object is to provide an iridium complex compound, which is soluble in an organic solvent such as toluene or phenylcyclohexane, which can be stored for long periods without reprecipitation of any solid fraction in the composition containing the compound and which secures a low driving voltage and a high luminescent efficiency of the element produced using the compound.

Other objects of the present invention are to provide an organic electroluminescent element that needs a low driving voltage but has a high luminescent efficiency, and to provide a display and a lighting containing the organic electroluminescent element.

Solution to Problem

The present inventors have assiduously studied in consideration of the above-mentioned problems and, as a result, have found that an iridium complex compound having a specific chemical structure has a sufficiently high solubility in an organic solvent such as toluene, phenylcyclohexane or the like, that a composition containing the compound and a solvent can be stored for long periods without reprecipitation of any solid fraction therein, and further that the element produced using the composition needs a low driving voltage but has a high luminescent efficiency, and have hereby completed the present invention.

Specifically, the present invention resides in the following [1] to [22].

[1] An iridium complex compound represented by the following formula (1):

[Chem. 1]

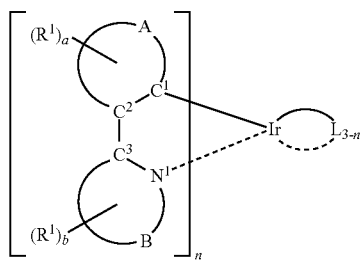

in the formula (1), the ring A represents a 6-membered or 5-membered aromatic hydrocarbon ring containing the carbon atoms $C^1$ and $C^2$ or a 6-membered or 5-membered heteroaromatic ring containing the carbon atoms $C^1$ and $C^2$, the ring B represents a 6-membered or 5-membered nitrogen-containing heteroaromatic ring containing the carbon atom $C^3$ and the nitrogen atom $N^1$; L represents an organic ligand; a and b each independently indicate an integer of from 1 to 4; n indicates an integer of from 1 to 3;

$R^1$ and $R^2$ each represent a substituent bonding to the carbon atom or the nitrogen atom that constitutes the ring A and the ring B, respectively, multiple $R^1$s and $R^2$s each are the same or different, and $R^1$ and $R^2$ represents any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms;

when a is 2 or more and multiple $R^1$s neighbor to each other, then the neighboring $R^1$s may bond directly, or may bond via an alkylene group having from 3 to 12 carbon atoms, an alkenylene group having from 3 to 12 carbon atoms, or an arylene group having from 6 to 12 carbon atoms thereby to further form a ring; when b is 2 or more and multiple $R^2$s neighbor to each other, then the neighboring $R^2$s may bond directly, or may bond via an alkylene group having from 3 to 12 carbon atoms, an alkenylene group having from 3 to 12 carbon atoms, or an arylene group having from 6 to 12 carbon atoms thereby to further form a ring; $R^1$ and $R^2$ may bond directly, or may bond via an alkylene group having from 3 to 12 carbon atoms, an alkenylene group having from 3 to 12 carbon atoms, or an arylene group having from 6 to 12 carbon atoms thereby to further form a ring; the ring formed by bonding of $R^1$s, $R^2$s or $R^1$ and $R^2$ may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms;

provided that at least one of $R^1$ and $R^2$ is represented by the following formula (2):

[Chem. 2]

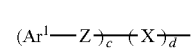

(2)

in the formula (2), multiple Xs are the same or different, and X represents a (hetero)arylene group having from 6 to 20 carbon atoms, multiple $Ar^1$s are the same or different, and $Ar^1$ represents a (hetero)aryl group having from 3 to 20 carbon atoms; these groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms; Z is represented by the following formula (3); c indicates an integer of from 1 to 3; d indicates an integer of from 0 to 3:

[Chem. 3]

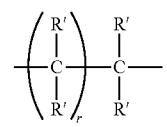

(3)

in the formula (3), multiple R's are the same or different, and R' represents a hydrogen atom, a fluorine atom, a chlorine atom, a bromine atom, an alkyl group having from 1 to 20 carbon atoms, an alkoxy group having from 1 to 20 carbon atoms, a (hetero)aryloxy group having from 3 to 20 carbon atoms, or a (hetero)aryl group having from 3 to 20 carbon atoms; r indicates an integer of from 1 to 20.

[2] The iridium complex compound according to [1] above, wherein in the formula (1), at least one of the substituents $R^1$s bonding to the ring A is represented by the formula (2).

[3] The iridium complex compound according to [1] or [2], wherein in the formula (1), at least one of the substituents $R^2$s bonding to the ring B is represented by the formula (2).

[4] The iridium complex compound according to any one of [1] to [3], wherein in the formula (1), the ring A is a benzene ring or a pyridine ring.

[5] The iridium complex compound according to any one of [1] to [4], which is represented by the following formula (1-1):

[Chem. 4]

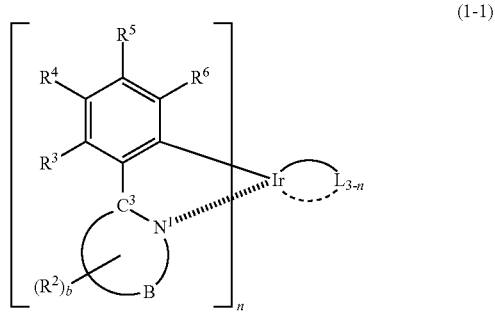

(1-1)

in the formula (1-1), the ring B, $R^2$, L, b and n each have the same meanings as in the formula (1);

$R^3$ to $R^6$ each are the same or different, and represent any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms; these groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms;

regarding $R^3$ to $R^6$, the neighboring $R^3$s to $R^6$s may bond directly, or may bond via an alkylene group having from 3 to 12 carbon atoms, an alkenylene group having from 3 to 12 carbon atoms, or an arylene group having from 6 to 12 carbon atoms thereby to form a ring; these rings may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms;

provided that the iridium complex compound represented by the formula (1-1) has at least one group represented by the formula (2) at $R^2$ to $R^6$.

[6] The iridium complex compound according to [5], wherein $R^4$ is represented by the formula (2).

[7] The iridium complex compound according to [5], wherein $R^5$ is represented by the formula (2).

[8] The iridium complex compound according to any one of [1] to [7], wherein the ring B is a pyridine ring, a pyrazine ring, a pyrimidine ring, an imidazole ring, an oxazole ring or a thiazole ring.

[9] The iridium complex compound according to any one of [1] to [7], wherein the ring B is a pyridine ring.

[10] The iridium complex compound according to any one of [1] to [7], wherein the ring B is a pyrazine ring.

[11] The iridium complex compound according to any one of [1] to [7], wherein the ring B is a pyrimidine ring.

[12] The iridium complex compound according to any one of [1] to [7], wherein the ring B is an imidazole ring.

[13] The iridium complex compound according to any one of [1] to [12], wherein in the formula (2), d is an integer of from 1 to 3.

[14] The iridium complex compound according to any one of [1] to [13], wherein in the formula (2), $Ar^1$ is an aromatic hydrocarbon group having from 6 to 20 carbon atoms.

[15] The iridium complex compound according to any one of [1] to [14], wherein in the formula (2), the substituent with which $Ar^1$ may be substituted is a fluorine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 1 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

[16] A light-emitting material comprising the iridium complex compound according to any one of [1] to [15].

[17] A composition comprising the iridium complex compound according to any one of [1] to [15] and a solvent.

[18] An organic electroluminescent element comprising an anode, a cathode and at least one organic layer between the anode and the cathode, wherein at least one layer of the organic layers contains the iridium complex compound according to any one of [1] to [15].

[19] The organic electroluminescent element according to [18], wherein the organic layer further contains a nitrogen-containing aromatic heterocyclic compound as a charge transport material.

[20] The organic electroluminescent element according to [18] or [19], wherein the organic layer is a layer formed using the composition according to [17].

[21] A display using the electroluminescent element according to any one of [18] to [20].

[22] A lighting using the electroluminescent element according to any one of [18] to [20].

Specifically having a configuration where a ligand of a substituted phenylpyridine or substituted phenylquinoline backbone is substituted with an aromatic ring having from 3 to 20 carbon atoms, via an alkyl group with a carbon chain having from 2 to 20 carbon atoms and at the end thereof, the iridium complex compound of the present invention has a high solubility and can exhibit good performance as a material for organic electroluminescent elements. In addition, the organic electroluminescent element containing the iridium complex compound of the present invention exhibits good performance in point of the luminescent efficiency, the driving voltage, etc.

Advantageous Effects of Invention

The iridium complex compound of the present invention is soluble in an organic solvent such as toluene or phenylcyclohexane, and in addition, a composition containing the iridium complex compound and a solvent can be stored for long periods without precipitation of any solid fraction. Further, an organic electroluminescent element containing the iridium complex compound has a high luminescent efficiency and can be driven even at a low voltage, and the driving stability thereof is high. Accordingly, the iridium complex compound of the present invention is useful as a material for organic electroluminescent elements, the organic electroluminescent element containing the compound can be produced according to a coating method, and the organic electroluminescent element is useful for displays and lightings.

BRIEF DESCRIPTION OF DRAWINGS

FIG. 1 shows the $^1$H-NMR chart of a compound D-1.

FIG. 2 is a cross-sectional view schematically showing one example of a configuration of the organic electroluminescent element of the present invention.

DESCRIPTION OF EMBODIMENTS

Embodiments of the present invention are described in detail hereinunder. However, the present invention is not limited to the following embodiments but can be modified variously within the scope and the spirit thereof.

In this description, (hetero)aryl group means both an aromatic hydrocarbon group and an aromatic heterocyclic group having one free atomic valence.

Here, in the present invention, the free atomic valence means one capable of forming a bond with any other free atomic valence, as described in Organic Chemistry/Biochemistry Nomenclature (Part 1) (Revised 2nd Ed., published by Nanko-do, 1992). Specifically, for example, "benzene ring having one free atomic valence" means a phenyl group; and "benzene ring having two free atomic valences" means a phenylene group.

Simple expression of "ppm" indicates "ppm by weight".

<Iridium Complex Compound>

The iridium complex compound of the present invention is represented by the following formula (1):

[Chem. 5]

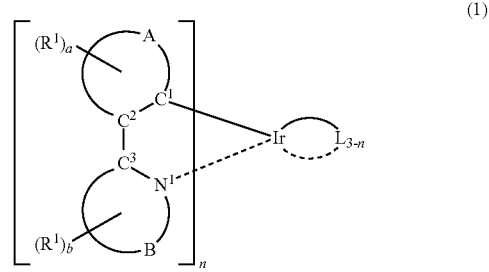

(1)

In the formula (1), the ring A represents, containing the carbon atoms $C^1$ and $C^2$, a 6-membered or 5-membered aromatic hydrocarbon ring or a 6-membered or 5-membered heteroaromatic ring, the ring B represents, containing the carbon atom $C^3$ and the nitrogen atom $N^1$, a 6-membered or 5-membered nitrogen-containing hetero aromatic ring.

The 6-membered or 5-membered aromatic hydrocarbon ring or the 6-membered or 5-membered heteroaromatic ring includes a benzene ring, a pyridine ring, a pyrimidine ring, a pyrazine ring, an imidazole ring, a furan ring, a thiophene ring, etc. From the viewpoint of durability and synthesis, preferred are a benzene ring, a pyridine ring and a pyrimidine ring. Above all, more preferred are a benzene ring and a pyridine ring, and even more preferred is a benzene ring.

The 6-membered or 5-membered nitrogen-containing heteroaromatic ring includes a pyridine ring, a pyrazine ring, a pyrimidine ring, a 1,3,5-triazine ring, an imidazole ring, a triazole ring, an oxazole ring, an oxadiazole ring, a thiazole ring, a thiadiazole ring, etc. From the viewpoint of durability and synthesis, preferred are a pyridine ring, a pyrazine ring, a pyrimidine ring, an imidazole ring, an oxazole ring and a thiazole ring. Above all, more preferred are a pyridine ring, a pyrazine ring, a pyrimidine ring and an imidazole ring, and even more preferred are a pyridine ring, a pyrazine ring and a pyrimidine ring.

L represents an organic ligand. a and b each independently indicate an integer of from 1 to 4. n indicates an integer of from 1 to 3.

In the chemical formulae in this description, the bond represented by a dashed line means a coordinate bond.

$R^1$ and $R^2$ each represent a substituent bonding to the carbon atom or the nitrogen atom that constitutes the ring A and the ring B, respectively, and multiple $R^1$s and $R^2$s each are the same or different, representing any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

These groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

When a is 2 or more and multiple $R^1$s neighbor to each other, then the neighboring $R^1$s may bond directly, or may bond via an alkylene group having from 3 to 12 carbon atoms, an alkenylene group having from 3 to 12 carbon atoms, or an arylene group having from 6 to 12 carbon atoms thereby to further form a ring.

Concretely there are mentioned a fluorene ring, a naphthalene ring, a phenanthrene ring, a triphenylene ring, a chrysene ring, a benzofuran ring, a dibenzofuran ring, a benzothiophene ring, a dibenzothiophene ring, a carbazole ring, a carboline ring, a diazacarbazole ring, a tetrahydronaphthalene ring, a quinoline ring, a quinazoline ring, an azaphenanthrene ring, an azatriphenylene ring, etc. Above all, preferred are a fluorene ring, a naphthalene ring, a carbazole ring, a carboline ring, a quinoline ring, a quinazoline ring, a quinoxaline ring, and an azatriphenylene ring, and more preferred are a fluorene ring, a naphthalene ring and a carbazole ring.

When b is 2 or more and multiple $R^2$s neighbor to each other, then the neighboring $R^2$s may bond directly, or may bond via an alkylene group having from 3 to 12 carbon atoms, an alkenylene group having from 3 to 12 carbon atoms, or an arylene group having from 6 to 12 carbon atoms thereby to further form a ring.

Specific examples of the ring include a carboline ring, a diazacarbazole ring, an azadibenzofuran ring, an azadibenzothiophene ring, a benzimidazole ring, a benzoxazole ring, a benzoxadiazole ring, a benzothiazole ring, a benzothiadiazole ring, a quinoline ring, a tetrahydroquinoline ring, an isoquinoline ring, a tetrahydroisoquinoline ring, a quinoxaline ring, a quinazoline ring, a diazaanthracene ring, an azaphenanthrene ring, a diazaphenanthrene ring, an azatriphenylene ring, a diazatriphenylene ring, etc. Above all, preferred are a benzoxazole ring, a benzothiazole ring, a quinoline ring, an isoquinoline ring, an quinoxaline ring, a quinazoline ring, an azaphenanthrene ring, and an azatriphenylene ring, and more preferred are a quinoline ring, an isoquinoline ring, a quinoxaline ring, a quinazoline ring, an azaphenanthrene ring and an azatriphenylene ring.

$R^1$ and $R^2$ may bond directly, or may bond via an alkylene group having from 3 to 12 carbon atoms, an alkenylene group having from 3 to 12 carbon atoms, or an arylene group having from 6 to 12 carbon atoms thereby to further form a ring.

Specific examples of the ring include an azaphenanthrene ring, a diazaphenanthrene ring, an azatriphenylene ring, a diazatriphenylene ring, etc. Above all, preferred are an azatriphenylene ring and a diazatriphenylene ring.

The ring formed by bonding of $R^1$s, $R^2$s or $R^1$ and $R^2$ may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

However, at least one of $R^1$ and $R^2$ is represented by the following formula (2):

[Chem. 6]

(2)

In the formula (2), multiple Xs are the same or different, each representing a (hetero)arylene group having from 6 to 20 carbon atoms, multiple $Ar^1$s are the same or different, each representing a (hetero)aryl group having from 3 to 20 carbon atoms.

These groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

Z is represented by the following formula (3). c indicates an integer of from 1 to 3. From the viewpoint of satisfying both solubility and performance, c is preferably 1 or 2, more preferably 1. d indicates an integer of from 0 to 3. From the viewpoint of durability, d is preferably an integer of from 1 to 3, more preferably 1 or 2.

[Chem. 7]

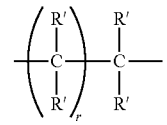

(3)

In the formula (3), multiple R's are the same or different, each representing a hydrogen atom, a fluorine atom, a chlorine atom, a bromine atom, an alkyl group having from 1 to 20 carbon atoms, an alkoxy group having from 1 to 20 carbon atoms, a (hetero)aryloxy group having from 3 to 20 carbon atoms, or a (hetero)aryl group having from 3 to 20 carbon atoms.

From the viewpoint of durability, preferred is a hydrogen atom, an alkyl group having from 1 to 20 carbon atoms, or a (hetero)aryl group having from 3 to 20 carbon atoms. Above all, more preferred is a hydrogen atom.

r indicates an integer of from 1 to 20. From the viewpoint of solubility and electric durability, r is preferably from 2 to less than 18, more preferably from 3 to less than 15, even more preferably from 3 to less than 10.

More preferably, the iridium complex compound represented by the formula (1) of the present invention is represented by the following formula (1-1):

[Chem. 8]

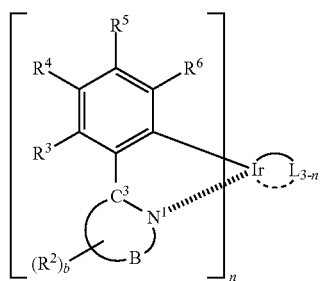

(1-1)

In the formula (1-1), the ring B, $R^2$, L, b and n each have the same meanings as in the formula (1).

$R^3$ to $R^6$ each are the same or different, representing any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

These groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

Regarding $R^3$ to $R^6$, the neighboring $R^3$s to $R^6$s may bond directly, or may bond via an alkylene group having from 3 to 12 carbon atoms, an alkenylene group having from 3 to 12 carbon atoms, or an arylene group having from 6 to 12 carbon atoms thereby to form a ring.

Specific examples of the ring include a fluorene ring, a naphthalene ring, a phenanthrene ring, a triphenylene ring, a chrysene ring, a benzofuran ring, a dibenzofuran ring, a benzothiophene ring, a dibenzothiophene ring, a carbazole ring, a carboline ring, a diazacarbazole ring, a tetrahydronaphthalene ring, a quinoline ring, a quinazoline ring, an azaphenanthrene ring, an azatriphenylene ring, etc. Above all, preferred are a fluorene ring, a naphthalene ring, a carbazole ring, a carboline ring, a quinoline ring, a quinazoline ring, a quinoxaline ring, and an azatriphenylene ring, and more preferred are a fluorene ring, a naphthalene ring and a carbazole ring.

These rings may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

The iridium complex compound represented by the formula (1-1) has at least one group represented by the formula (2) at $R^2$ to $R^6$.

The iridium complex compound of the present invention has a substituent represented by the formula (2). Having the substituent, the iridium complex compound of the present invention has an improved solubility in organic solvents. From the viewpoint of driving voltage and durability, it is desirable that at least one of $R^1$ and $R^2$ has the substituent. Also from the viewpoint of driving voltage and durability, it is desirable that at least one of $R^2$ to $R^6$ has the substituent. More preferably, $R^4$ or $R^5$ has the substituent, and even more preferably $R^4$ has the substituent.

<$R^1$ to $R^6$>

$R^1$ and $R^2$ each represent a substituent bonding to the carbon atom or the nitrogen atom that constitutes the ring A and the ring B, respectively, and multiple $R^1$s and $R^2$s each are the same or different, representing any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

$R^3$ to $R^6$ each are the same or different, representing any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

Specific examples of the alkyl group having from 1 to 20 carbon atoms include a linear alkyl group, a branched alkyl group, a cyclic alkyl group, etc., and more concretely a methyl group, an ethyl group, an n-propyl group, an n-butyl group, an n-pentyl group, an n-hexyl group, an n-octyl group, an isopropyl group, an isobutyl group, an isopentyl group, a t-butyl group, a cyclohexyl group, etc. Above all, preferred is a linear alkyl group such as a methyl group, an ethyl group, an n-butyl group, an n-hexyl group, etc.

The (hetero)aralkyl group having from 7 to 40 carbon atoms is a group derived from a linear alkyl group, a branched alkyl group or a cyclic alkyl group by substituting a part of the hydrogen atoms constituting the group with a (hetero)aryl group, and more concretely, specific examples of the group include a 1-phenyl-1-ethyl group, a cumyl group, a 3-pyridyl-1-propyl group, a 3-phenyl-1-propyl group, a 4-phenyl-1-butyl group, a 5-phenyl-1-pentyl group, a 6-pyridyl-1-hexyl group, a 6-phenyl-1-hexyl group, a 7-phenyl-1-heptyl group, a 4-phenyl-1-cyclohexyl group, a tetrahydronaphthyl group, etc. Above all, preferred are a 5-phenyl-1-pentyl group, a 6-phenyl-1-hexyl group and a 7-phenyl-1-heptyl group.

Specific examples of the alkoxy group having from 1 to 20 carbon atoms include a methoxy group, an ethoxy group, a propyloxy group, an isopropyloxy group, a hexyloxy group, a cyclohexyloxy group, an octadecyloxy group, etc. Above all, preferred is a hexyloxy group.

Specific examples of the (hetero)aryloxy group having from 3 to 20 carbon atoms include a pyridyloxy group, a phenoxy group, a 4-methylphenyloxy group, etc. Above all, preferred is a phenoxy group.

Specific examples of the alkylsilyl group having from 1 to 20 carbon atoms include a trimethylsilyl group, a triethylsilyl group, a triisopropylsilyl group, a dimethylphenyl group, a t-butyldimethylsilyl group, a t-butyldiphenylsilyl group, etc. Above all, preferred is a triisopropyl group, a t-butyldimethylsilyl group, and a t-butyldiphenylsilyl group.

Specific examples of the (hetero)arylsilyl group having from 3 to 20 carbon atoms include a diphenylpyridylsilyl group, a triphenylsilyl group, etc. Above all, preferred is a triphenylsilyl group.

Specific examples of the alkylcarbonyl group having from 2 to 20 carbon atoms include an acetyl group, a propionyl group, a pivaloyl group, a caproyl group, a decanoyl group, a cyclohexylcarbonyl group, etc. Above all, preferred are an acetyl group and a pivaloyl group.

Specific examples of the (hetero)arylcarbonyl group having from 4 to 20 carbon atoms include an arylcarbonyl group, a benzoyl group, a naphthoyl group, an anthroyl group, etc. Above all, preferred is a benzoyl group.

Specific examples of the alkylamino group having from 2 to 20 carbon atoms include a methylamino group, a dimethylamino group, a diethylamino group, an ethylmethylamino group, a dihexylamino group, a dioctylamino group, a dicyclohexylamino group, etc. Above all, preferred are a dimethylamino group and a dicyclohexylamino group.

Specific examples of the (hetero)arylamino group having from 3 to 20 carbon atoms include a (4-pyridylphenyl)phenylamino group, a phenylamino group, a diphenylamino group, a di(4-tolyl)amino group, a di(2,6-dimethylphenyl)amino group, etc. Above all, preferred are a diphenylamino group and a di(4-tolyl)amino group.

The (hetero)aryl group having from 3 to 20 carbon atoms means both an aromatic hydrocarbon group and an aromatic heterocyclic group having one free atomic valence. Specific examples of the group include residues of a benzene ring, a naphthalene ring, an anthracene ring, a phenanthrene ring, a perylene ring, a tetracene ring, a pyrene ring, a benzopyrene ring, a chrysene ring, a triphenylene ring, a fluoranthene ring, a furan ring, a benzofuran ring, a dibenzofuran ring, a thiophene ring, a benzothiophene ring, a dibenzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a perimidine ring, a quinazoline ring, a quinazolinone ring, an azulene ring and the like, all having one free atomic valence.

From the viewpoint of quantum yield and durability, preferred are a benzene ring, a naphthalene ring, a dibenzofuran ring, a dibenzothiophene ring, a carbazole ring, a pyridine ring, a pyrimidine ring and a triazine ring, all having one free valance. Above all, more preferred are a benzene ring and a pyridine ring having one free atomic valence, and even more preferred is a benzene ring having one free atomic valence.

These groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms.

Specific examples of the alkyl group having from 1 to 20 carbon atoms, the (hetero)aralkyl group having from 7 to 40 carbon atoms, the alkoxy group having from 1 to 20 carbon atoms, the (hetero)aryloxy group having from 3 to 20 carbon atoms, the alkylsilyl group having from 1 to 20 carbon atoms, the (hetero)arylsilyl group having from 3 to 20 carbon atoms, the alkylcarbonyl group having form 2 to 20 carbon atoms, the (hetero)arylcarbonyl group having from 4 to 20 carbon atoms, the alkylamino group having from 2 to 20 carbon atoms, the (hetero)arylamino group having from 3 to 20 carbon atoms, and the (hetero)aryl group having from 3 to 20 carbon atoms are the same as those mentioned in the previous section.

When a is 2 or more and multiple $R^1$s neighbor to each other, then the neighboring $R^1$s may bond directly, or may bond via an alkylene group having from 3 to 12 carbon atoms, an alkenylene group having from 3 to 12 carbon atoms, or an arylene group having from 6 to 12 carbon atoms thereby to further form a ring.

Specific examples of the ring include a fluorene ring, a naphthalene ring, a phenanthrene ring, a triphenylene ring, a chrysene ring, a benzofuran ring, a dibenzofuran ring, a benzothiophene ring, a dibenzothiophene ring, a carbazole ring, a carboline ring, a diazacarbazole ring, a tetrahydronaphthalene ring, a quinoline ring, a quinazoline ring, an azaphenanthrene ring, an azatriphenylene ring, etc. Above all, preferred are a fluorene ring, a naphthalene ring, a carbazole ring, a carboline ring, a quinoline ring, a quinazoline ring, a quinoxaline ring, and an azatriphenylene ring, and more preferred are a fluorene ring, a naphthalene ring and a carbazole ring.

When b is 2 or more and multiple $R^2$s neighbor to each other, then the neighboring $R^2$s may bond directly, or may bond via an alkylene group having from 3 to 12 carbon atoms, an alkenylene group having from 3 to 12 carbon atoms, or an arylene group having from 6 to 12 carbon atoms thereby to further form a ring.

Specific examples of the ring include a carboline ring, a diazacarbazole ring, an azadibenzofuran ring, an azadibenzothiophene ring, a benzimidazole ring, a benzoxazole ring, a benzoxadiazole ring, a benzothiazole ring, a benzothiadiazole ring, a quinoline ring, a tetrahydroquinoline ring, an isoquinoline ring, a tetrahydroisoquinoline ring, a quinoxaline ring, a quinazoline ring, a diazaanthracene ring, an azaphenanthrene ring, a diazaphenanthrene ring, an azatriphenylene ring, a diazatriphenylene ring, etc. Above all, preferred are a benzoxazole ring, a benzothiazole ring, a quinoline ring, an isoquinoline ring, an quinoxaline ring, a quinazoline ring, an azaphenanthrene ring, and an azatriphenylene ring, and more preferred are a quinoline ring, an isoquinoline ring, a quinoxaline ring, a quinazoline ring, an azaphenanthrene ring and an azatriphenylene ring.

$R^1$ and $R^2$ may bond directly, or may bond via an alkylene group having from 3 to 12 carbon atoms, an alkenylene group having from 3 to 12 carbon atoms, or an arylene group having from 6 to 12 carbon atoms thereby to further form a ring.

Specific examples of the ring include an azaphenanthrene ring, a diazaphenanthrene ring, an azatriphenylene ring, a diazatriphenylene ring, etc. Above all, preferred are an azatriphenylene ring and a diazatriphenylene ring.

These rings may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms. Specific examples of these substituents are the same as those mentioned in the previous section.

Regarding $R^3$ to $R^6$, the neighboring $R^3$s to $R^6$s may bond directly, or may bond via an alkylene group having from 3 to 12 carbon atoms, an alkenylene group having from 3 to 12 carbon atoms, or an arylene group having from 6 to 12 carbon atoms thereby to form a ring.

Specific examples of the ring include a fluorene ring, a naphthalene ring, a phenanthrene ring, a triphenylene ring, a chrysene ring, a benzofuran ring, a dibenzofuran ring, a benzothiophene ring, a dibenzothiophene ring, a carbazole ring, a carboline ring, a diazacarbazole ring, a tetrahydronaphthalene ring, a quinoline ring, a quinazoline ring, an azaphenanthrene ring, an azatriphenylene ring, etc. Above all, preferred are a fluorene ring, a naphthalene ring, a carbazole ring, a carboline ring, a quinoline ring, a quinazoline ring, a quinoxaline ring, and an azatriphenylene ring, and more preferred are a fluorene ring, a naphthalene ring and a carbazole ring.

These rings may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms. Specific examples of these substituents are the same as those mentioned in the previous section.

<X, $Ar^1$>

Multiple Xs are the same or different, each representing a (hetero)arylene group having from 6 to 20 carbon atoms, multiple $Ar^1$s are the same or different, each representing a (hetero)aryl group having from 3 to 20 carbon atoms.

The (hetero)arylene group having from 6 to 20 carbon atoms means both an aromatic hydrocarbon group and an aromatic heterocyclic group having two free atomic valences.

Specific examples of the group include residues of a benzene ring, a naphthalene ring, an anthracene ring, a phenanthrene ring, a perylene ring, a tetracene ring, a pyrene ring, a benzopyrene ring, a chrysene ring, a triphenylene ring, a fluoranthene ring, a furan ring, a benzofuran ring, a dibenzofuran ring, a thiophene ring, a benzothiophene ring, a dibenzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a benzimidazole ring, a perimidine ring, a quinazoline ring, a quinazolinone ring, an azulene ring and the like, all having two free atomic valences.

From the viewpoint of quantum yield and durability, preferred are a benzene ring, a naphthalene ring, a dibenzofuran ring, a dibenzothiophene ring, a carbazole ring, a pyridine ring, a pyrimidine ring and a triazine ring, all having two free valances. Above all, more preferred are a benzene ring and a pyridine ring having two free atomic valences, and even more preferred is a benzene ring having two free atomic valences.

The (hetero)aryl group having from 3 to 20 carbon atoms means both an aromatic hydrocarbon group and an aromatic heterocyclic group having one free atomic valence.

Specific examples of the group include residues of a benzene ring, a naphthalene ring, an anthracene ring, a phenanthrene ring, a perylene ring, a tetracene ring, a pyrene ring, a benzopyrene ring, a chrysene ring, a triphenylene ring, a fluoranthene ring, a furan ring, a benzofuran ring, a dibenzofuran ring, a thiophene ring, a benzothiophene ring, a dibenzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a benzimidazole ring, a perimidine ring, a quinazoline ring, a quinazolinone ring, an azulene ring and the like, all having one free atomic valence.

From the viewpoint of quantum yield and durability, preferred are a benzene ring, a naphthalene ring, a phenanthrene ring, a dibenzofuran ring, a dibenzothiophene ring, a carbazole ring, a pyridine ring, a pyrimidine ring and a triazine ring, all having one free valance. Above all, more preferred are a benzene ring, a naphthalene ring and a phenanthrene ring, all having one free atomic valence, and even more preferred are a benzene ring and a naphthalene ring having one free atomic valence.

These groups may be further substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms. Specific examples of these substituents are the same as those mentioned in the previous section of <$R^1$ to $R^6$>.

<Z>

Z is represented by the above-mentioned formula (3). Multiple R's are the same or different, each representing a hydrogen atom, a fluorine atom, a chlorine atom, a bromine atom, an alkyl group having from 1 to 20 carbon atoms, an alkoxy group having from 1 to 20 carbon atoms, a (hetero)aryloxy group having from 3 to 20 carbon atoms, or a (hetero)aryl group having from 3 to 20 carbon atoms.

From the viewpoint of durability, preferred are a hydrogen atom, an alkyl group having from 1 to 20 carbon atoms, and a (hetero)aryl group having from 3 to 20 carbon atoms. Above all, more preferred is a hydrogen atom. Specific examples of these substituents are the same as those mentioned in the previous section of <$R^1$ to $R^6$>.

r indicates an integer of from 1 to 20. From the viewpoint of solubility and electric durability, r is preferably from 2 to less than 18, more preferably from 3 to less than 15, even more preferably from 3 to less than 10.

<L>

L represents an organic ligand. Not specifically limited, L is preferably a monovalent bidentate ligand, and is more preferably selected from the following chemical formulae. In the chemical formulae, the dashed line means a coordinate bond.

In case where the formula has two organic ligands Ls, the organic ligands Ls each may have a different structure. When n is 3, L is absent.

[Chem. 9]

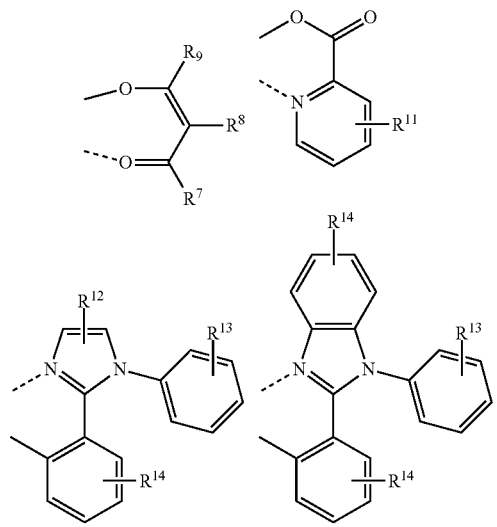

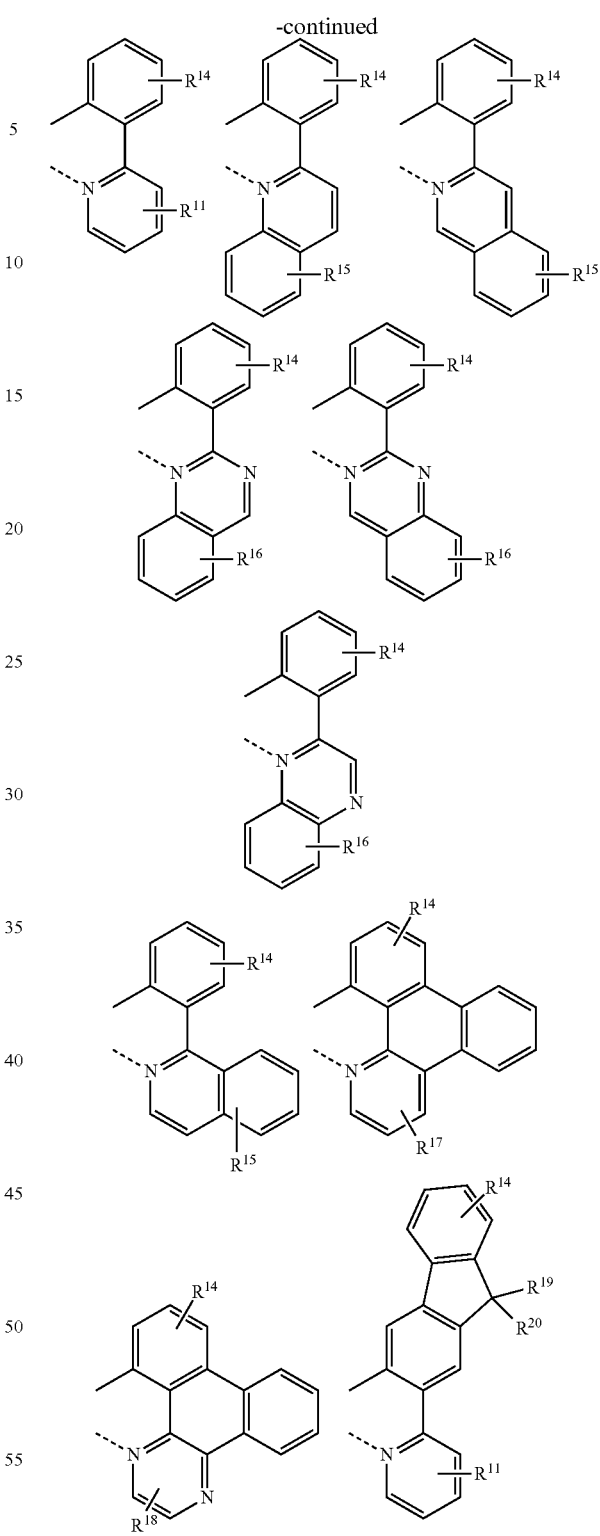

In the above formulae, $R^7$ to $R^9$, and $R^{11}$ to $R^{20}$ each independently represent a hydrogen atom, an alkyl group having from 1 to 20 carbon atoms and optionally substituted with a fluorine atom, a phenyl group optionally substituted with an alkyl group having from 1 to 20 carbon atoms, or a halogen atom. More preferably, $R^7$ and $R^9$ each are a methyl group or a t-butyl group, $R^8$ and $R^{11}$ to $R^{18}$ each are a hydrogen atom, or a phenyl group optionally substituted with an alkyl group having from 1 to 20 carbon atoms or a halogen atom, and $R^{19}$ and $R^{20}$ each are an alkyl group having from 1 to 20 carbon atoms. Specific examples of the alkyl group having from 1 to 20 carbon atoms are the same as those mentioned in the previous section <$R^1$ to $R^6$>.

<Molecular Weight>

The molecular weight of the iridium complex compound of the present invention is generally 850 or more, preferably 900 or more, and is generally 3000 or less, preferably 2000 or less. Falling within the range, the stability of the complex is good.

SPECIFIC EXAMPLES

Next, preferred examples of the iridium complex compound of the present invention are mentioned below, to which, however, the present invention is not limited. In the structural formulae, Me represents a methyl group, and Ph represents a phenyl group.

[Chem. 10]

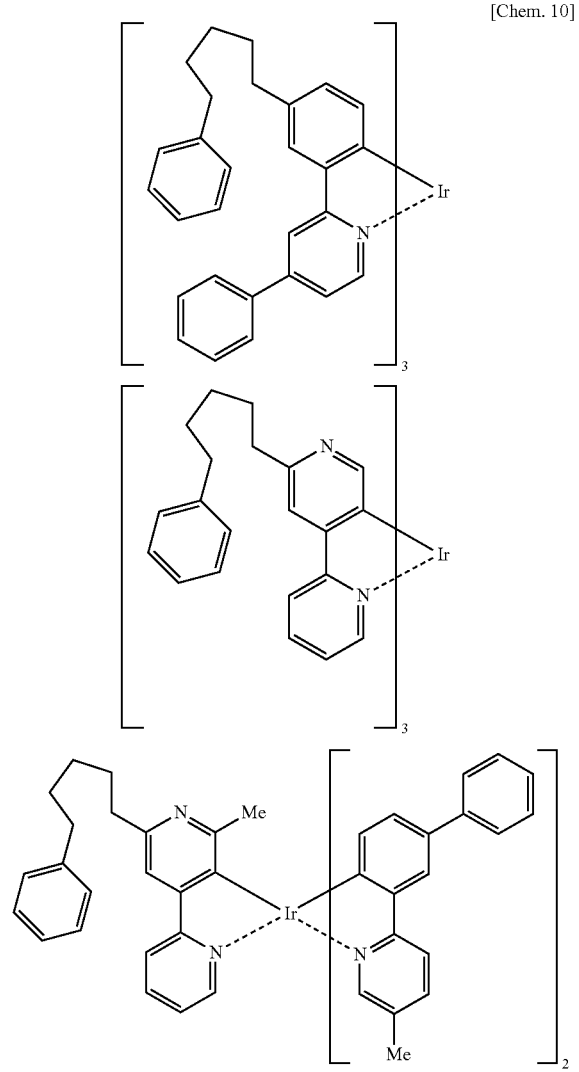

-continued

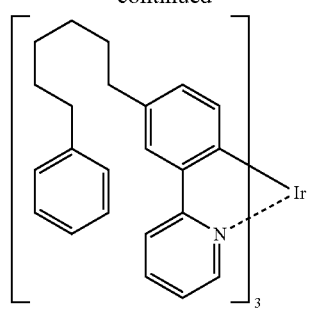

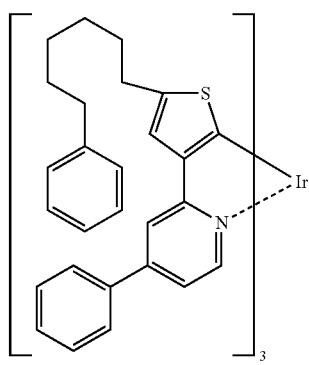

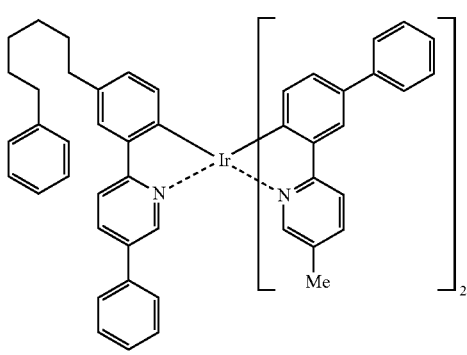

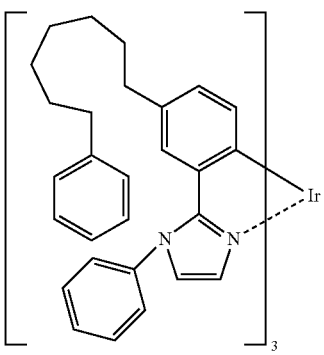

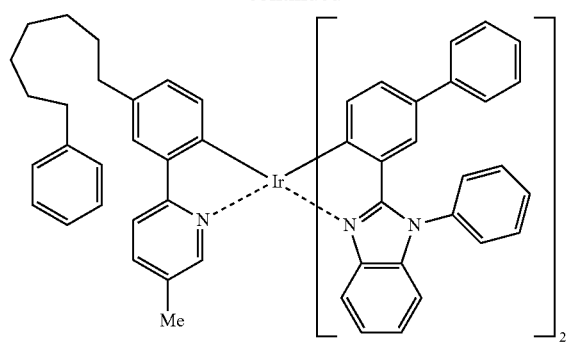
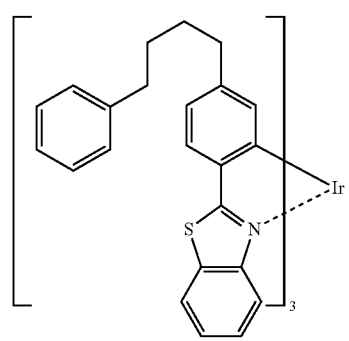
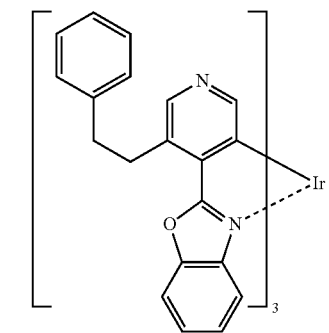
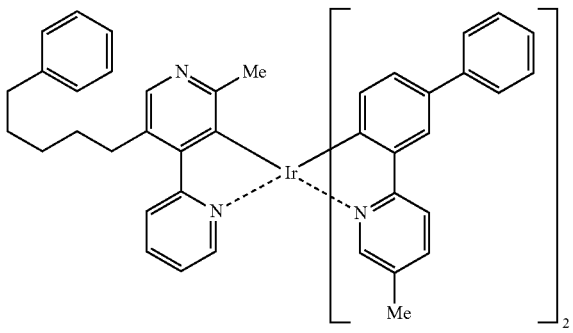
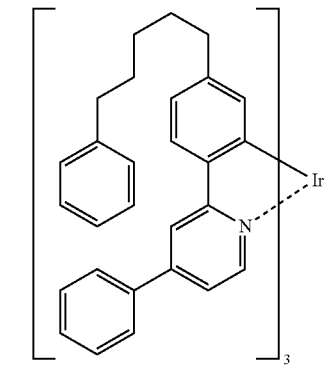
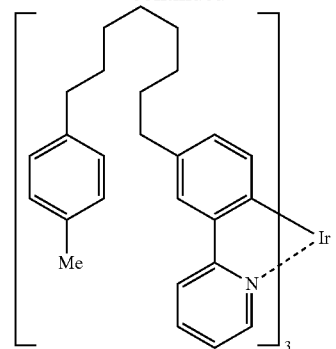
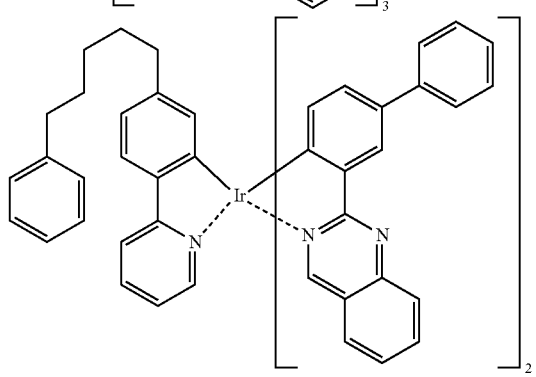
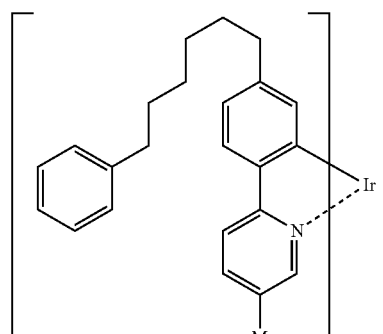
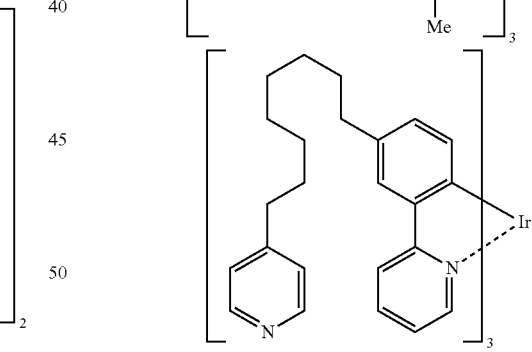
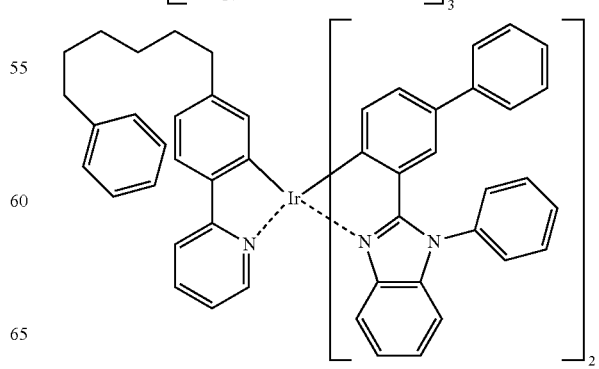

[Chem. 11]
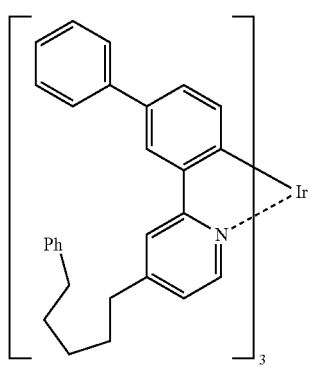
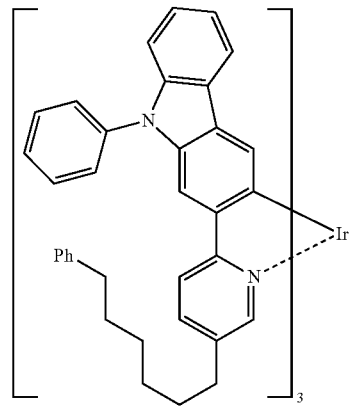
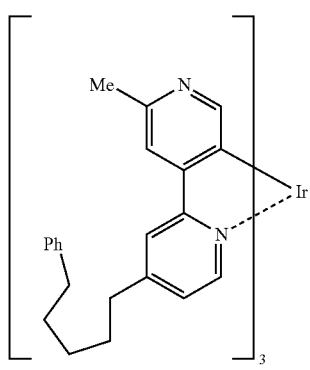
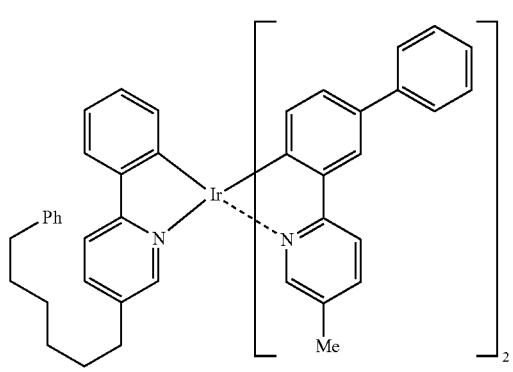
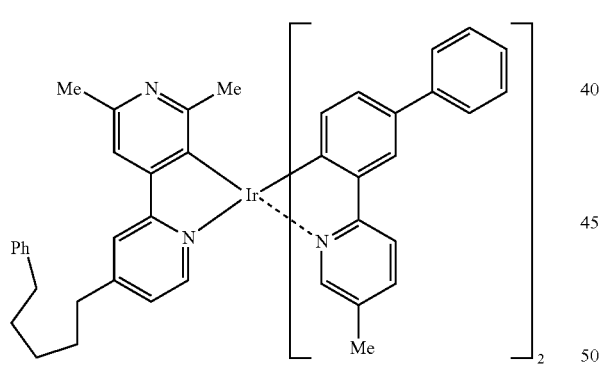
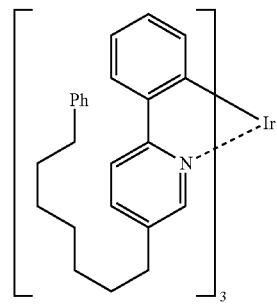
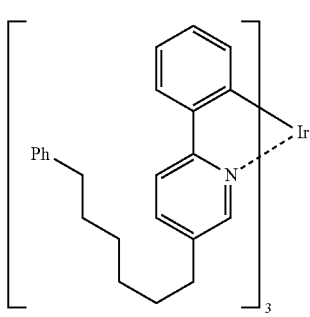
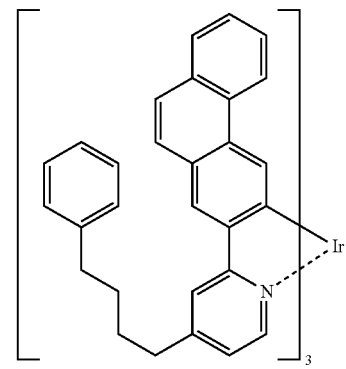

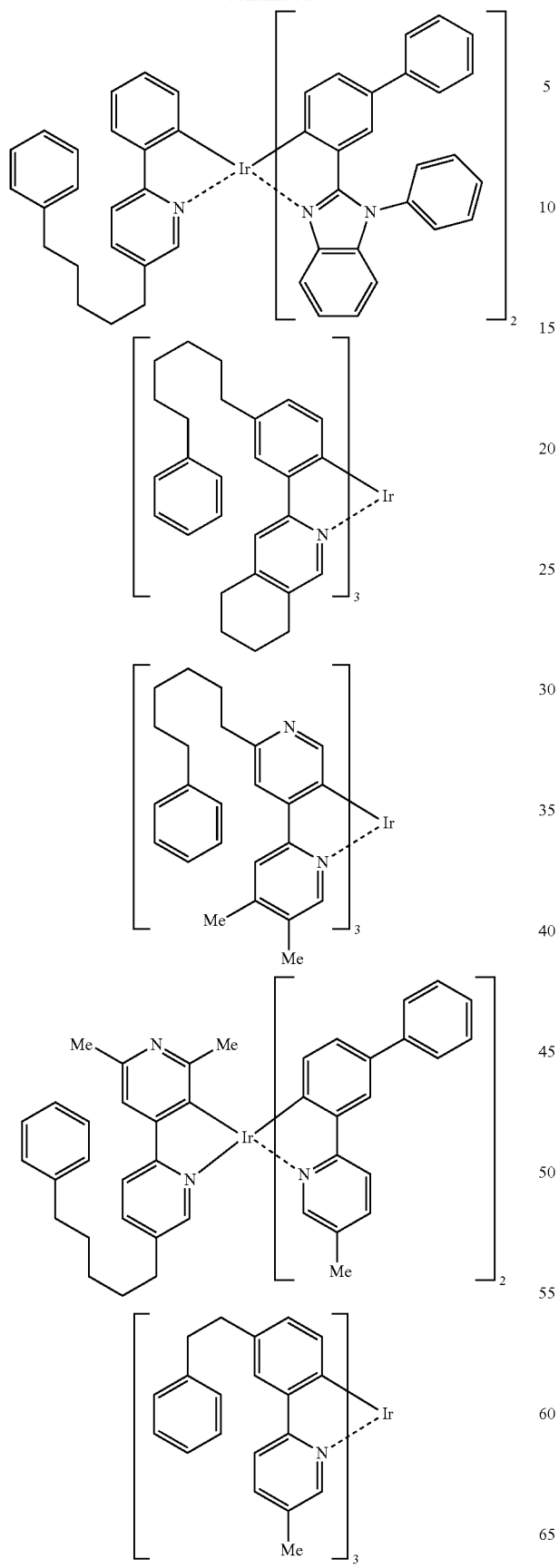
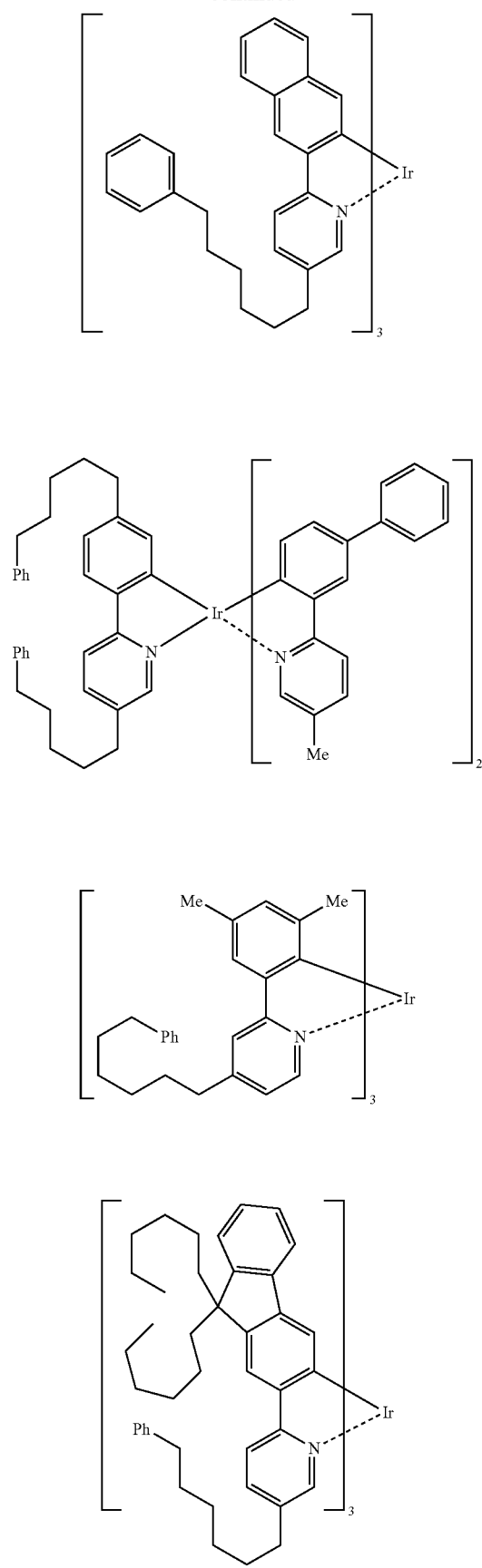

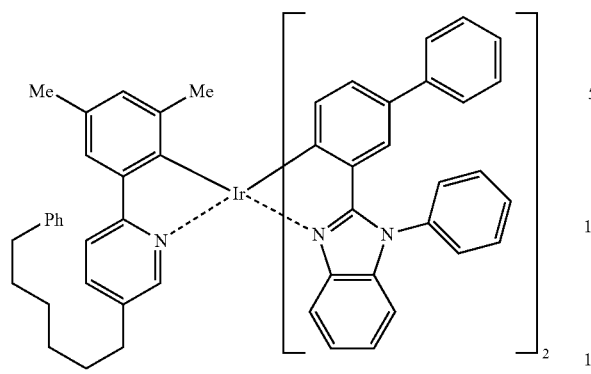
[Chem. 12]
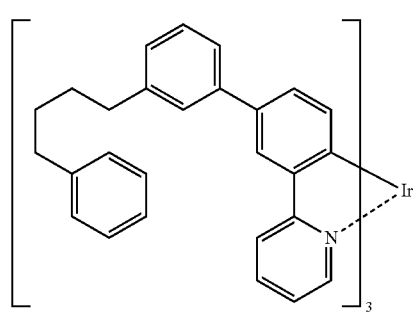
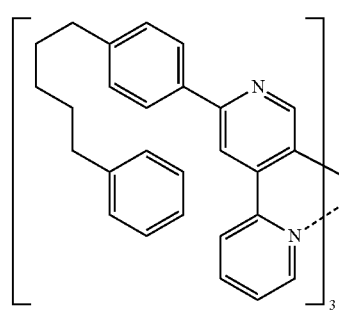
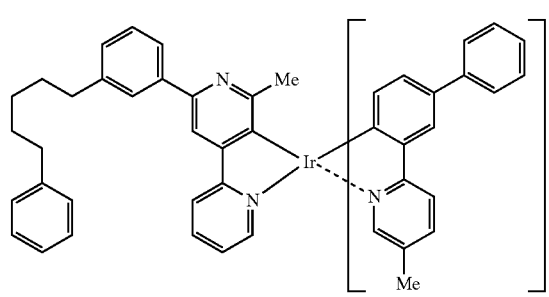
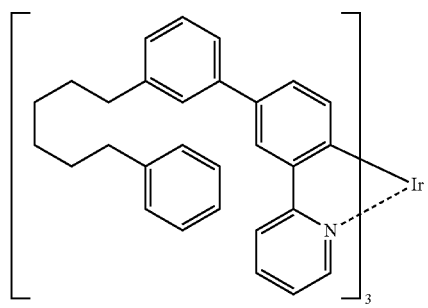
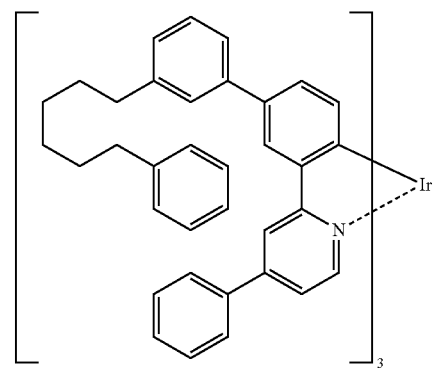
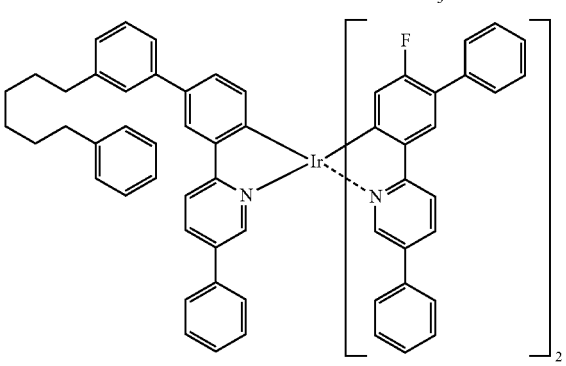
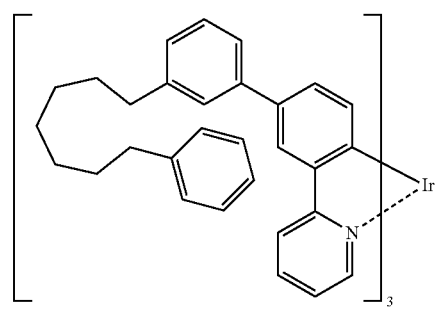
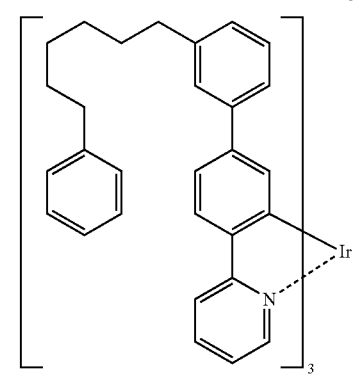
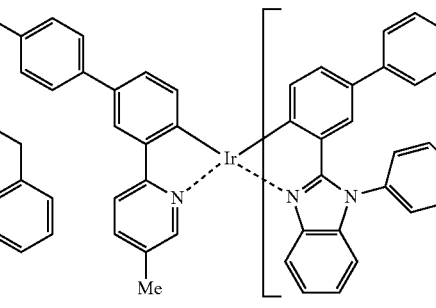

-continued
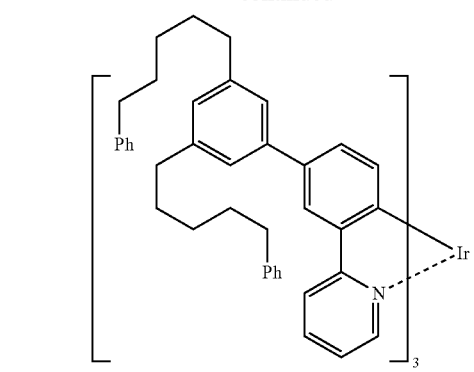
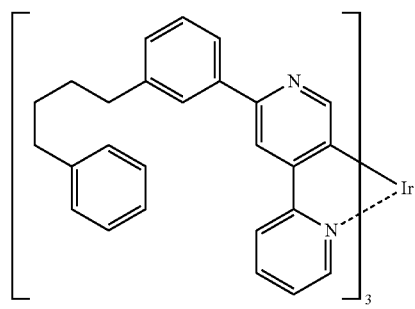
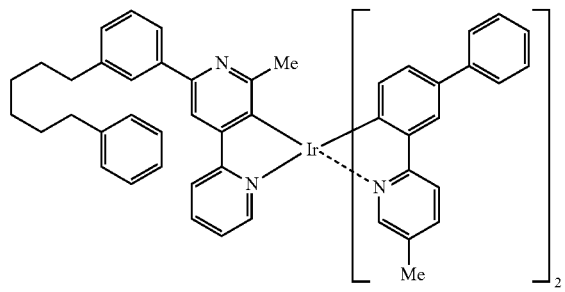
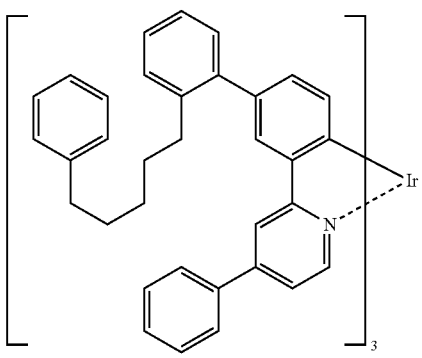
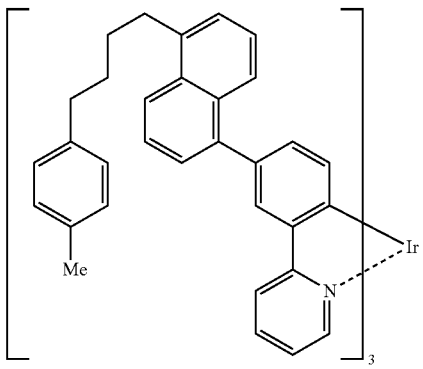
-continued
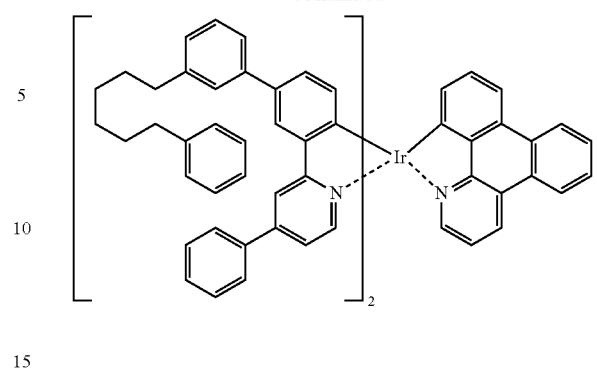
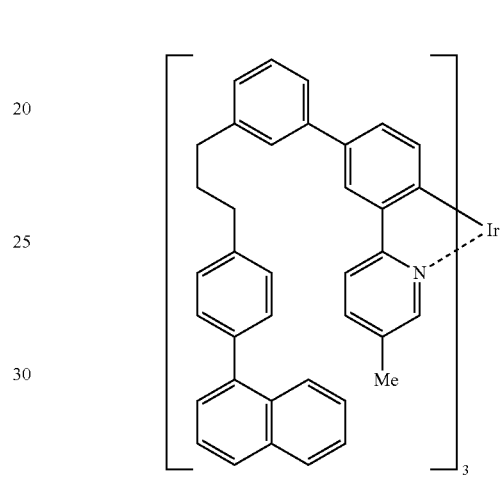
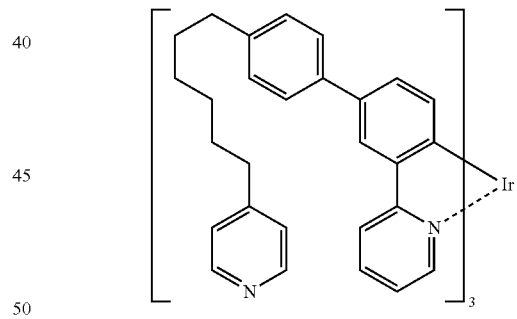
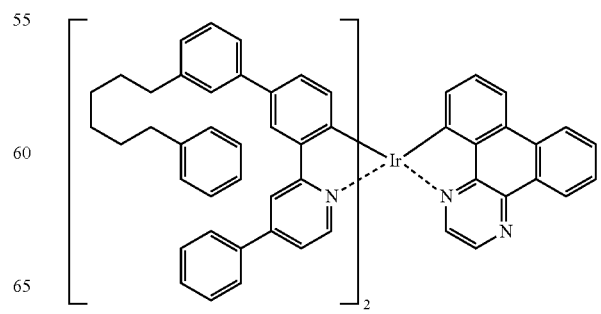

31
-continued
[Chem. 13]
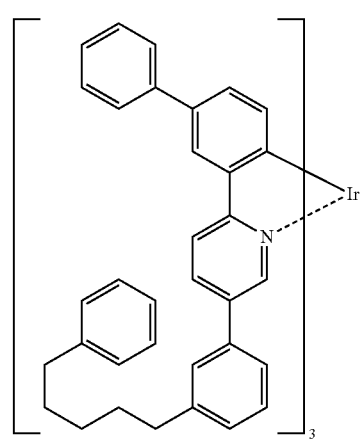
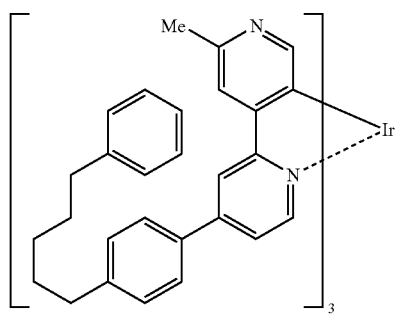
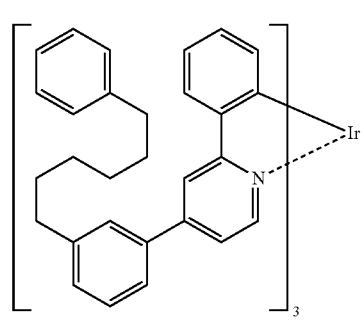
32
-continued
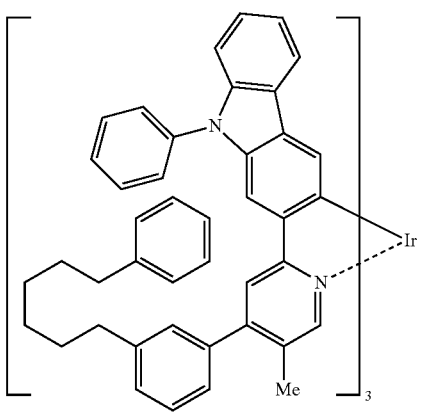
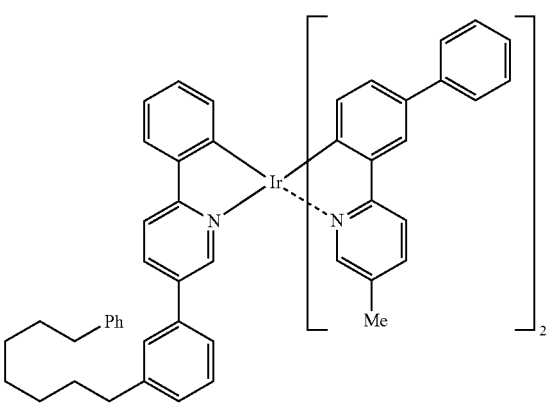
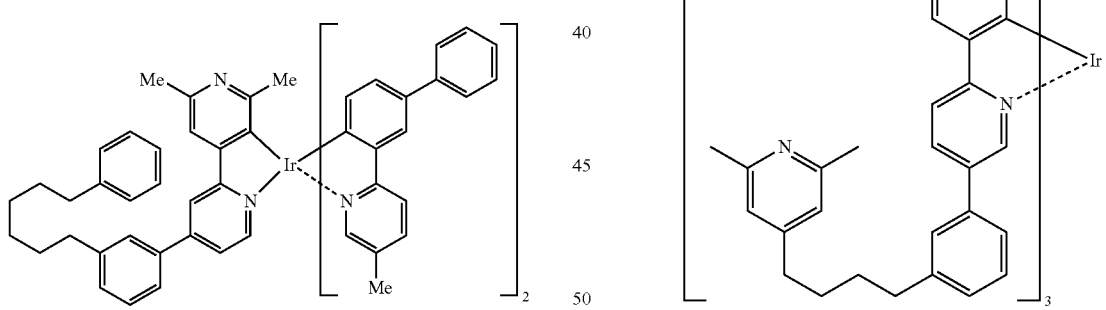
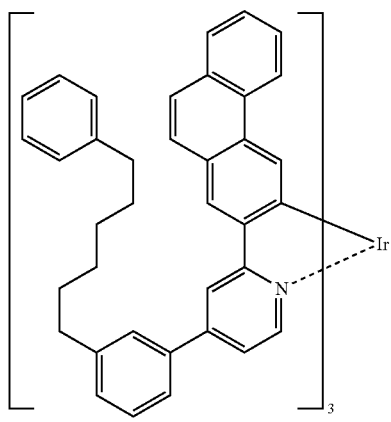

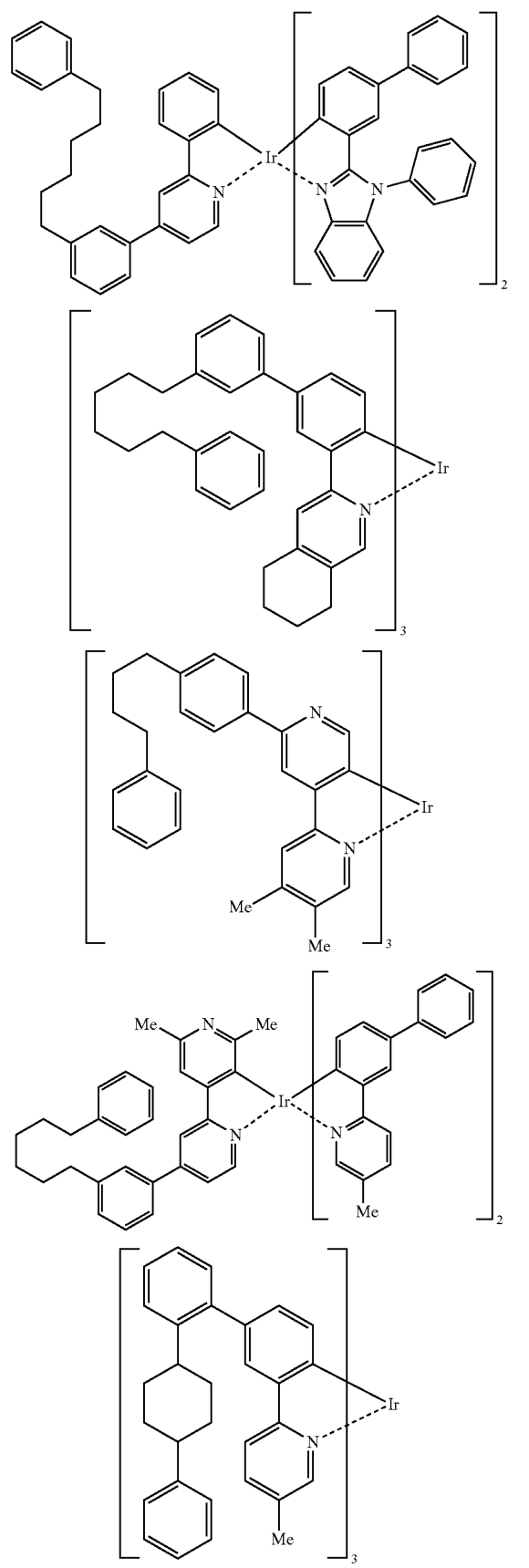
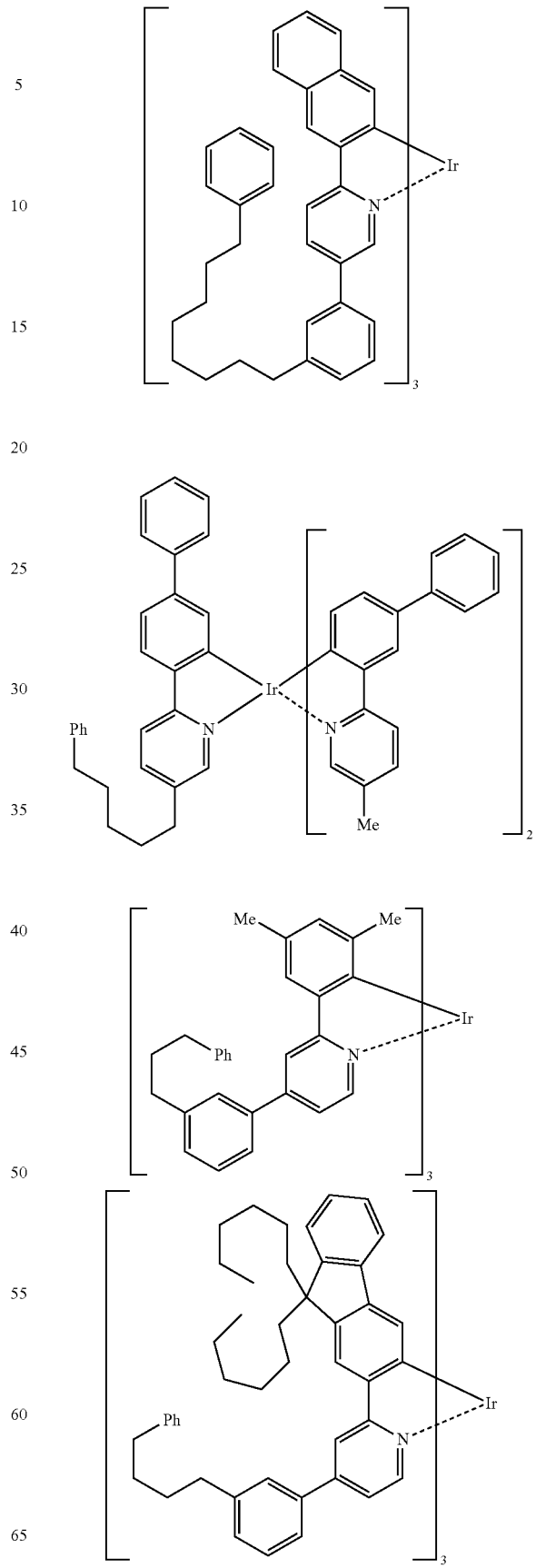

-continued
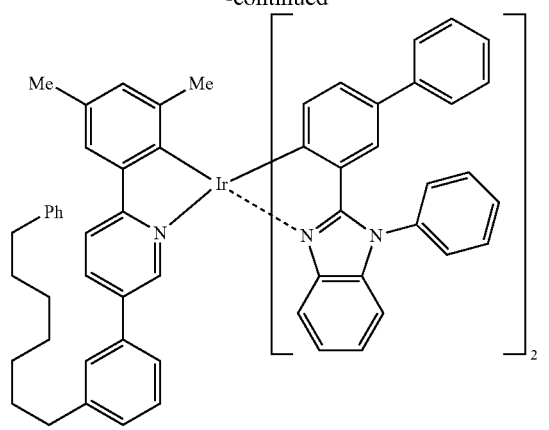
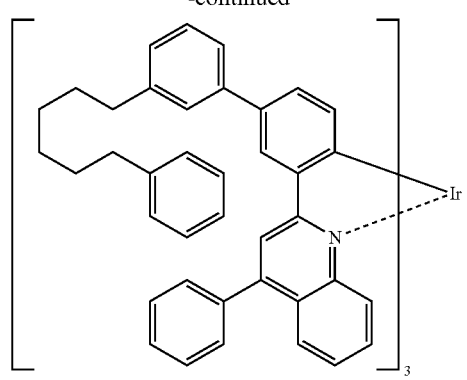
[Chem. 14]
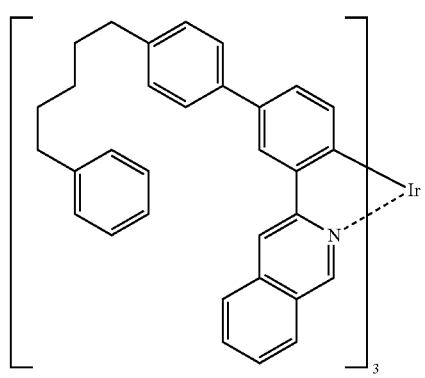
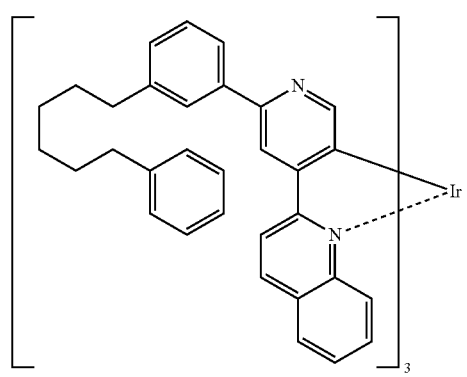
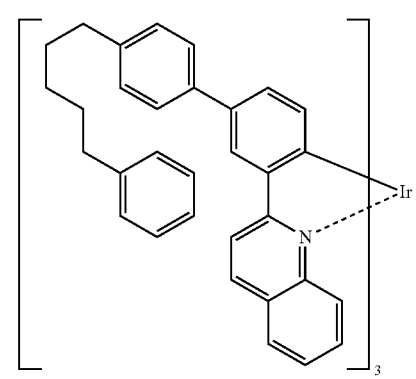
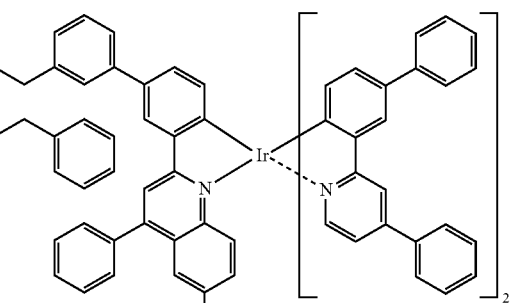
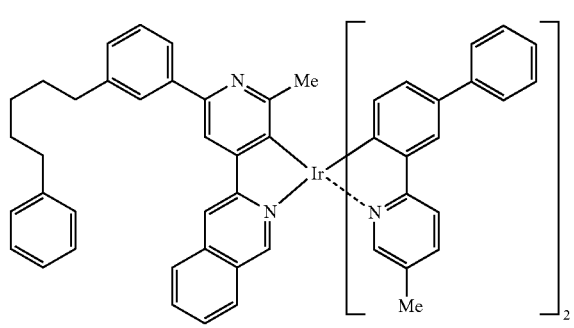
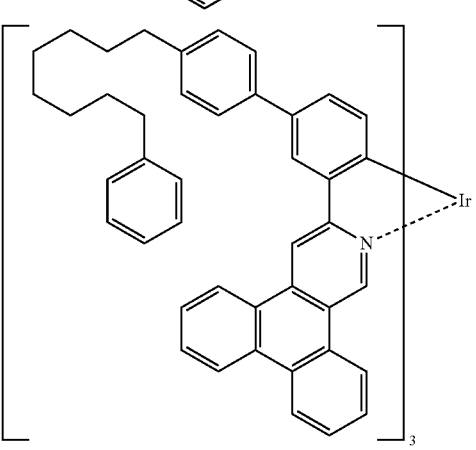

-continued
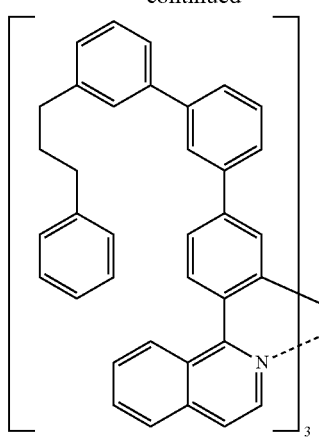
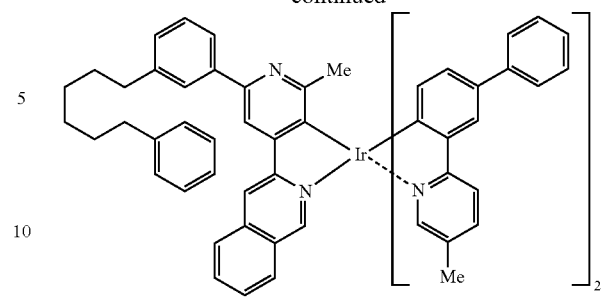
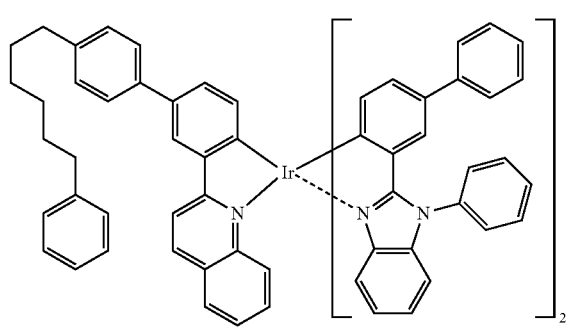
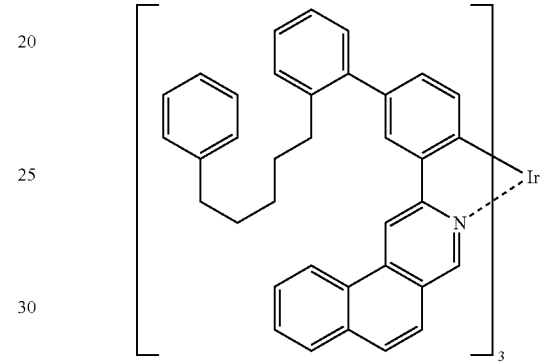
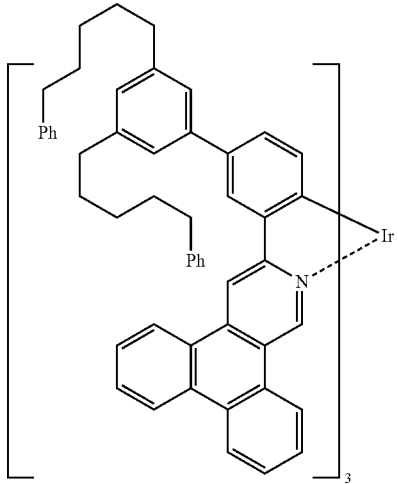
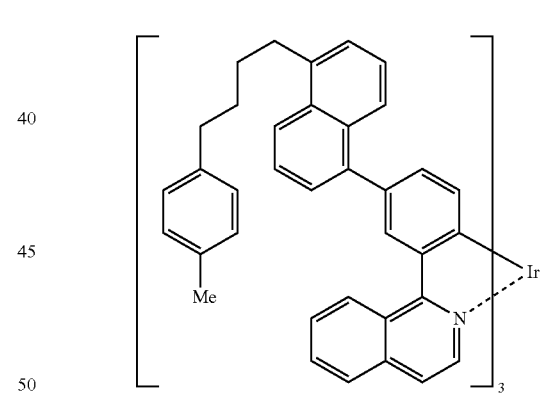
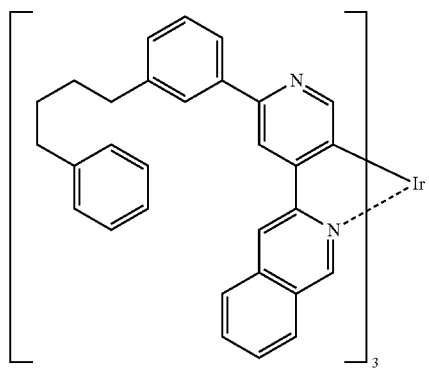
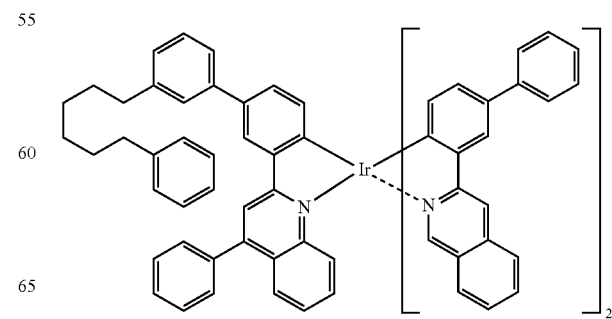

39
-continued
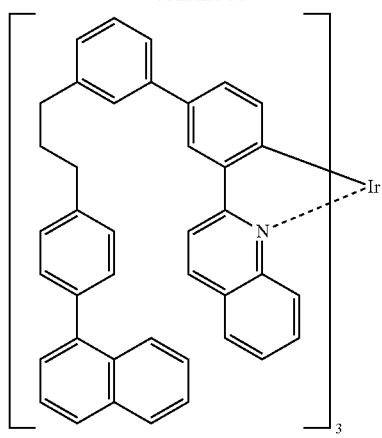
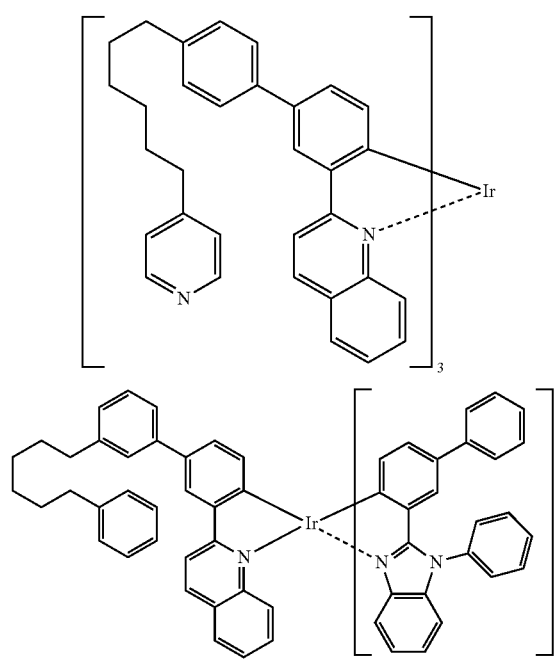
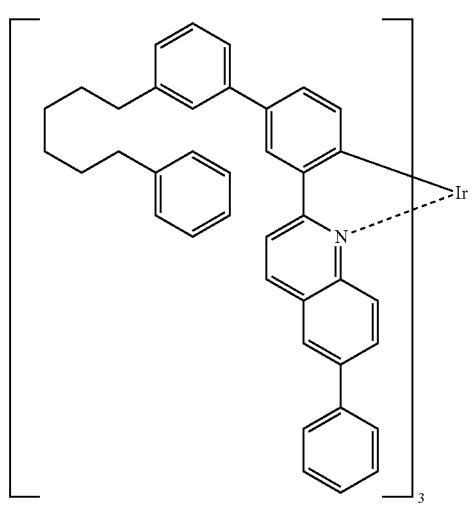
40
-continued
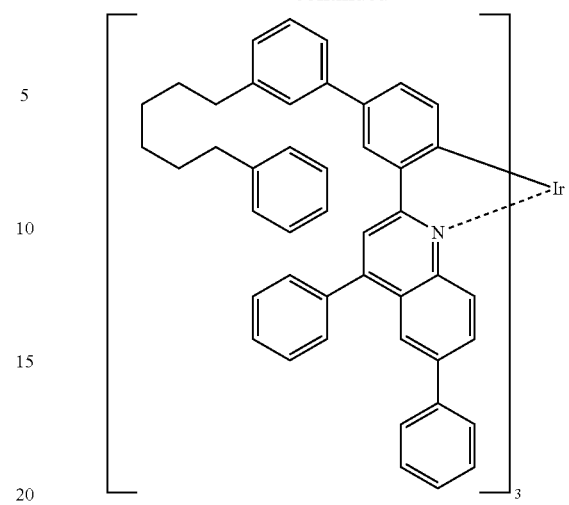
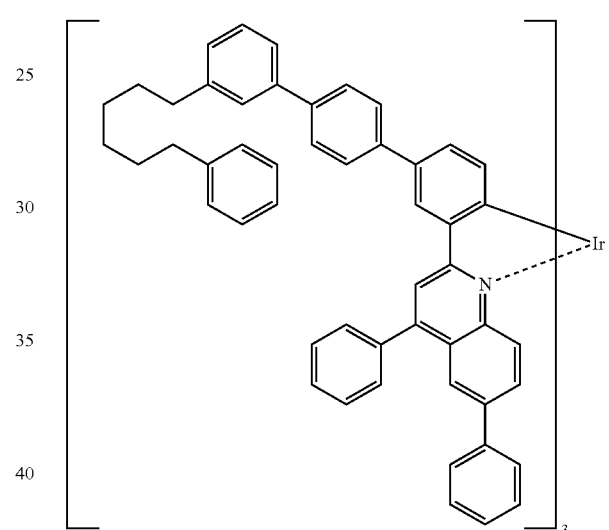
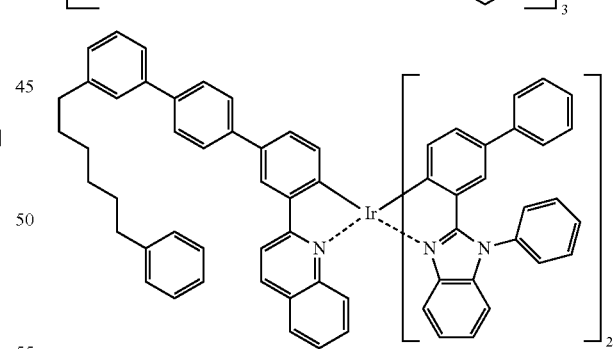
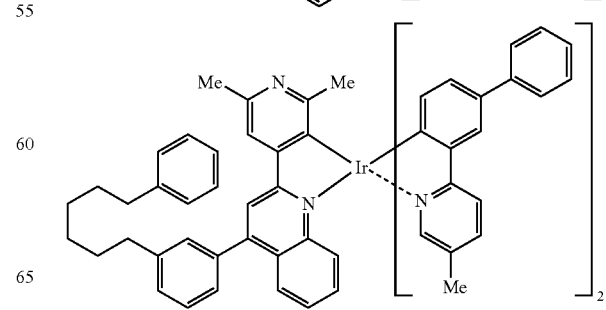
[Chem. 15]

-continued
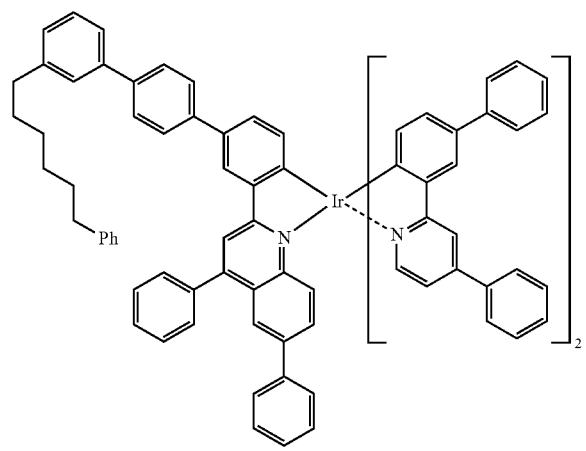
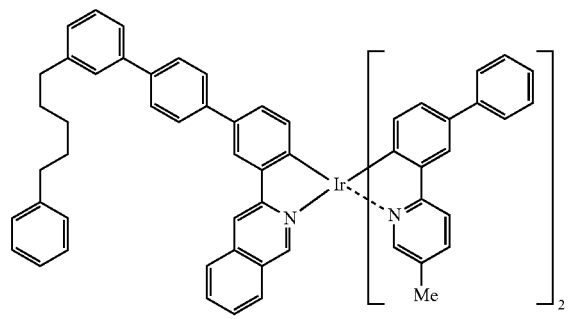
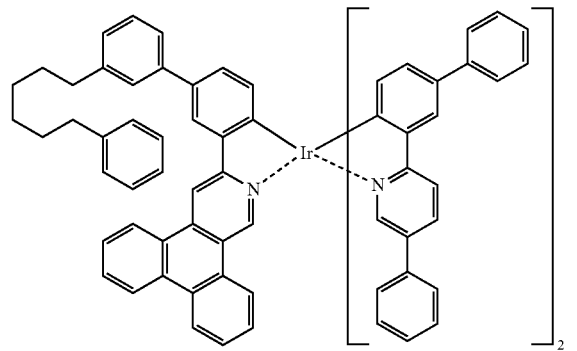
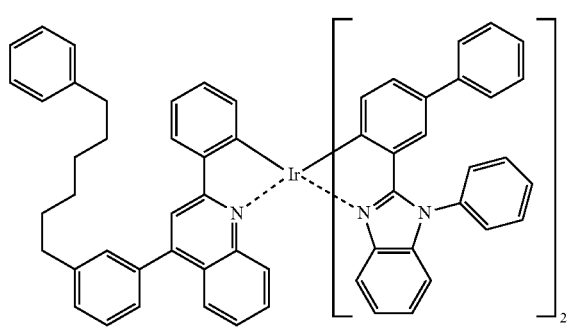
-continued
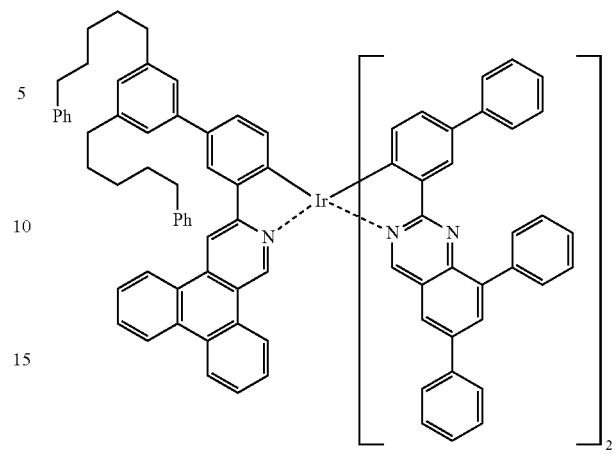
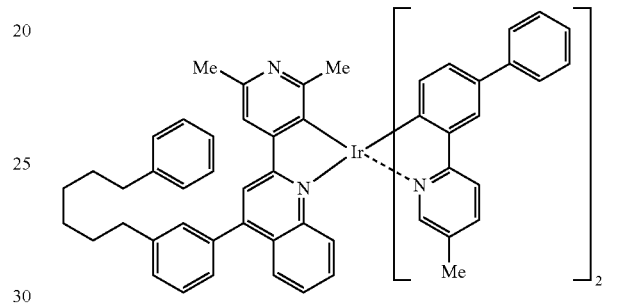
[Chem. 16]
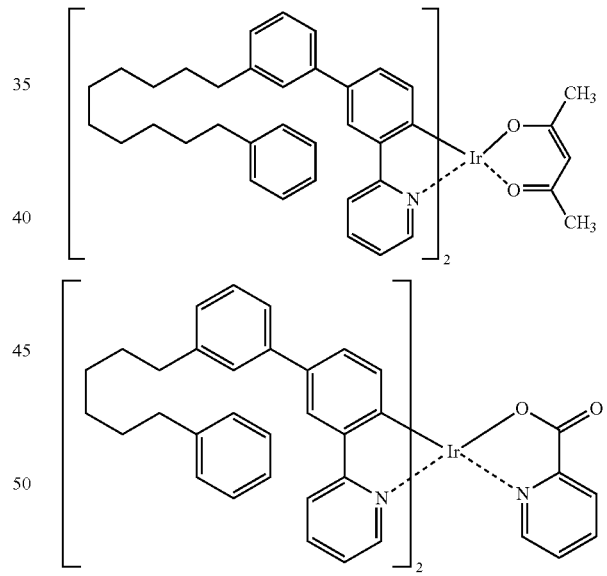
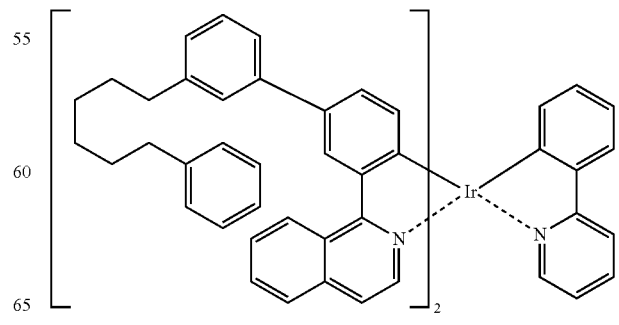

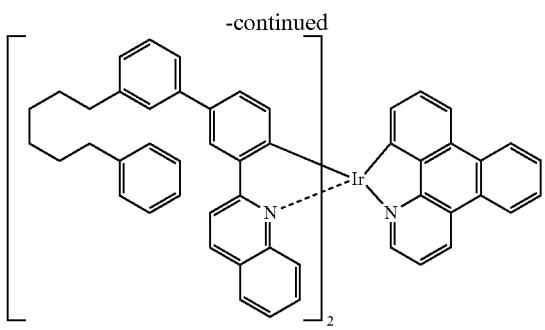

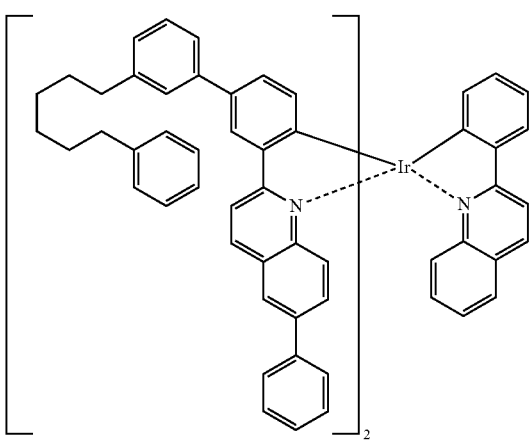

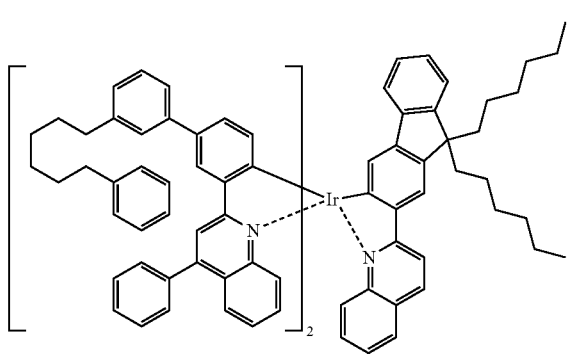

<Structural Characteristics>

The reason why the iridium complex compound of the present invention could have a sufficient high solubility in organic solvents such as toluene and phenylcyclohexane and the reason why elements produced using the compound could have good performance, for example, having a high luminescent efficiency could be presumed as follows:

For increasing solubility in organic solvents, in general, an alkyl group is introduced into the ligand of an iridium complex compound. An alkyl group can have a variety of conformations, and therefore in crystallization, the energy for rearrangement increases. Accordingly, the iridium complex compound hardly crystallizes and is therefore expected to have an increased solubility. However, the inventors' investigations made recently have revealed that mere alkyl group introduction could not always improve the solubility depending on the chain length of the group relative to the molecular size of the iridium complex compound, or that is, when the chain length is short, and also on the substitution position of the group.

On the contrary, when the chain length of the alkyl group is too long, the solubility could be expressed, however, since the site not contributing to light emission in the molecule would increase, there may occur some other problems that the luminescent efficiency may lower and the element performance may therefore worsen.

In addition, the alkyl group introduction involves other two disadvantages mentioned below. One is that the alkyl group is relatively weak in point of the chemical structure thereof, and, as compared with an aromatic ring, the $sp^3$ carbon-hydrogen bond in the group may be radically cleaved with ease to cause decomposition. Consequently, the driving life of the elements produced using the compound is short. Another is that the host compound to be used in a light-emitting layer is generally an aromatic compound, and when the iridium complex is substituted with an alkyl group introduced thereinto, then the solubility thereof in the host material worsens and therefore the complex may easily undergo phase separation from the host in forming a light-emitting layer through coating, and as a result, the dispersibility of the iridium complex compound in the in-layer host material worsens. This causes reduction in the luminescent efficiency and increase in the driving voltage.

The iridium complex compound of the present invention is substituted with an alkyl group having at least one aromatic ring at the end thereof, and therefore, while securing the improved solubility thereof in organic solvents and at the same time, the $sp^3$ carbon-hydrogen bond site of the alkyl group can be sterically protected to inhibit radical cleavage, and further, by improving the solubility thereof with an aromatic compound host material, the dispersibility of the iridium complex compound can be thereby improved. Owing to these synergistic effects, the iridium complex compound of the present invention has a high solubility and a sufficiently long pot life suitable to a coating method, and further have other advantages that the luminescent efficiency of the elements to be produced using the compound is increased and the driving voltage needed by the elements is lowered and additionally the driving life of the elements is long.

As described above, when the iridium complex compound of the present invention is used in an organic layer of an organic electroluminescent element to be produced through wet-process film formation, the organic electroluminescent element can have improved performance, or that is, the driving voltage to be needed by the element can be reduced and the driving life of the element can be prolonged.

<Description of Solubility>

Wet-process film formation is a method of film formation that comprises once dissolving an organic material for a light-emitting layer in an organic solvent and then applying the resulting solution onto a substrate according to spin-coating or inkjet technology, and thereafter removing the organic solvent through evaporation and vaporization by heating or depressurization or by applying an inert gas jet thereto. If desired, for making the formed film of the organic material insoluble in solvents, for example, a crosslinking group such as a C=C group, a C≡C group or a benzocyclobutene group may be made to exist in the molecule of the organic material, or according to a known method of heating or photoirradiation, the material may be crosslinked for insolubilization.

Regarding the type thereof, the organic solvent favorably used in such wet-process film formation includes optionally-substituted aliphatic compounds such as hexane, heptane, methyl ethyl ketone, ethyl acetate, butyl acetate; optionally-substituted aromatic compounds such as toluene, xylene, phenylcyclohexane, ethyl benzoate; optionally substituted alicyclic compounds such as cyclohexane, cyclohexanone, methylcyclohexanone, 3,3,5-trimethylcyclohexane, etc. These may be used singly, or multiple types of the solvents may be mixed to give a coating liquid favorable for the coating process for use herein.

Regarding the type thereof, the main organic solvent is preferably an aromatic compound or an aliphatic compound, more preferably an aromatic compound. In particular, phenylcyclohexane is more preferred in point of the viscosity and the boiling point thereof in wet-process film formation.

The solubility of the iridium complex compound favorable for wet-process film formation is generally 0.3% by weight or more in phenylcyclohexane under atmospheric pressure at 25° C., but preferably 1.0% by weight or more, more preferably 1.5% by weight or more.

<Method for Synthesis of Iridium Complex Compound>

The iridium complex compound of the present invention can be synthesized, using a ligand and an Ir compound, and the ligand can be synthesized through combination of known methods.

For the method for synthesis of the iridium complex compound, there can be exemplified a method of forming a tris-complex in one stage as shown in the formula (I), and a method of forming a tris-complex after formation of an intermediate of an Ir binuclear complex as shown in the formula (II). However, the present invention is not limited to these.

For example, as typical reaction shown by the formula (I), there is mentioned a method of obtaining a metal complex through reaction of 3 equivalents of a ligand and one equivalent of Ir(acac)₃ (iridium acetylacetonate complex).

[Chem. 17]

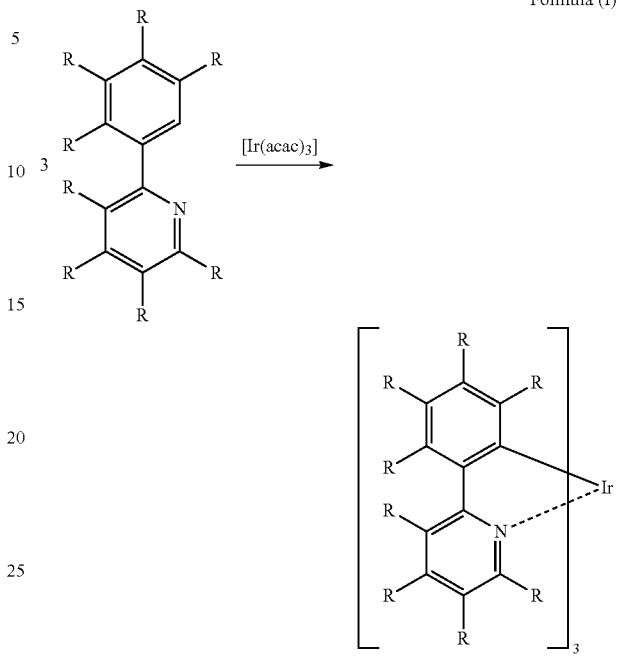

Formula (I)

In the formula (I), R represents a monovalent substituent.

In this, an excessive amount of the ligand may be used for accelerating the reaction, or a small amount thereof may be used for increasing the selectivity. Multiple types of ligands may be used and may be added successively to produce a mixed ligand complex.

As typical reaction represented by the formula (II), for example, there is mentioned a method of reacting two equivalents of a ligand and one equivalent of IrCl₃.xH₂O (iridium chloride.x-hydrate) to give an intermediate of a binuclear metal complex with two Ir atoms followed by further reacting the ligand with the intermediate in an amount of one equivalent relative to Ir to give the intended metal complex. In the formula (II), R has the same meaning as that of R in the formula (I).

[Chem. 18]

Formula (II)

-continued

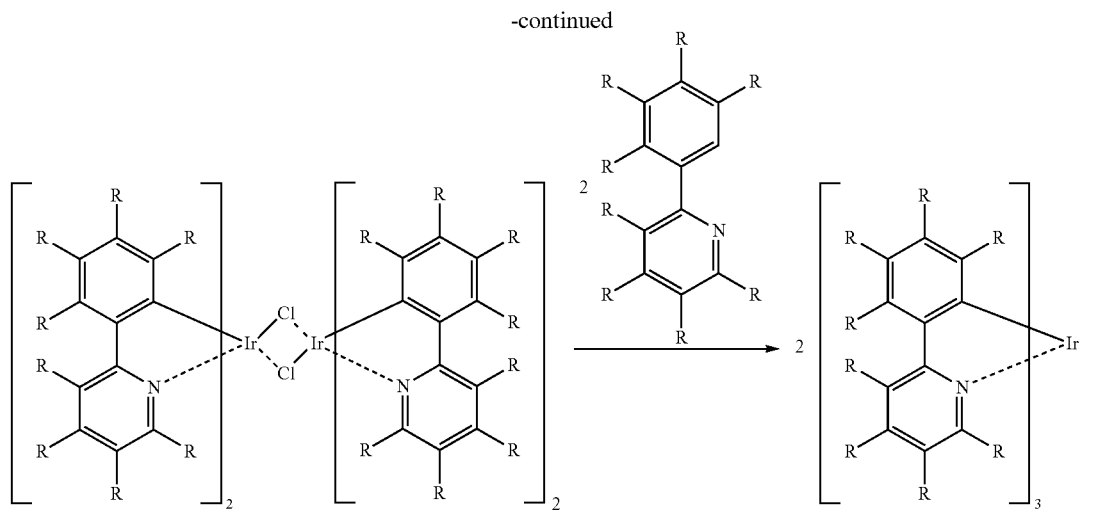

In consideration of the reaction efficiency and selectivity like in the formula (I), the actual compounding ratio of the ligand and the Ir compound can be suitably controlled. In the formula (II), the ligand to be added last may be made to differ from the first ligand to give a mixed ligand complex in a simplified manner.

As the Ir compound, any other suitable Ir compound may also be used here such as Ir cyclooctadienyl complex and the like, in addition to the above-mentioned Ir(acac)$_3$ complex and IrCl$_3$.xH$_2$O. A base compound such as a carbonate or the like, as well as a halogen-trapping agent such as an Ag salt or the like may also be added to accelerate the reaction. The reaction temperature is preferably from 50° C. to 400° C. or so. In general, a high temperature of 100° C. or more is employed. The reaction may be carried out in the absence of a solvent, or a known solvent may be used therein. In case where the reaction is at a high temperature, a high-boiling-point solvent such as glycerin or the like is preferably used.

<Use of Iridium Complex Compound>

The iridium complex compound of the present invention is favorable usable as a material for organic electroluminescent elements, or that is as an organic electroluminescent element material, and is also favorable usable as a light-emitting material for organic electroluminescent elements and other luminescent elements, etc.

<Iridium Complex Compound-Containing Composition>

The iridium complex compound of the present invention is excellent in solubility and is preferably used along with a solvent. A composition containing the iridium complex compound of the present invention and a solvent (hereinafter this may be referred to as "iridium complex compound-containing composition") is described below.

The iridium complex compound-containing composition of the present invention contains the above-mentioned iridium complex compound of the present invention and a solvent. The iridium complex compound-containing composition of the present invention is used generally for forming layers and films according to wet-process film formation, and in particular, favorably used for forming organic layers of organic electroluminescent elements. The organic layer is especially preferably a light-emitting layer.

In other words, the iridium complex compound-containing composition is preferably a composition for organic electroluminescent elements, and is more preferably used as a composition for forming a light-emitting layer.

The content of the iridium complex compound of the present invention in the iridium complex compound-containing composition is generally 0.01% by weight or more, preferably 0.1% by weight or more, and is generally 15% by mass or less, preferably 10% by mass or less. When the content of the iridium complex compound in the composition falls within the range, then holes and electron can be efficiently injected from the adjacent layers (for example, hole transport layer, hole-blocking layer) into the light-emitting layer, and the driving voltage can be thereby reduced. The iridium complex compound-containing composition may contain only one type of the iridium complex compound of the present invention, or may contain two or more different types of the compound as combined.

In case where the iridium complex compound-containing composition of the present invention is used, for example, for organic electroluminescent elements, the composition may further contain a charge-transporting compound for use in organic electroluminescent elements, especially in light-emitting layers, in addition to the above-mentioned iridium complex compound and solvent.

In case where the iridium complex compound-containing composition of the present invention is used in forming a light-emitting layer of an organic electroluminescent element, preferably, the composition contains the iridium complex compound of the present invention serves as a dopant material and a charge-transporting compound as a host material therein.

The solvent to be contained in the iridium complex compound-containing composition of the present invention is a volatile liquid component that is used for forming a layer containing the iridium complex compound through wet-process film formation.

Regarding the solvent, a solute of the iridium complex compound of the present invention is highly soluble therein, and therefore, not specifically defined, the solvent may be any and every solvent capable of well dissolving therein the charge-transporting compound to be mentioned below. Preferred solvents include, for example, alkanes such as n-decane, cyclohexane, ethylcyclohexane, decalin, bicyclohexane, etc.; aromatic hydrocarbons such as toluene, xylene, mesitylene, phenylcyclohexane, tetralin, etc.; halogenoaromatic hydrocarbons such as chlorobenzene, dichlorobenzene, trichlorobenzene, etc.; aromatic ethers such as 1,2-dimethoxybenzene, 1,3-dimethoxybenzene, anisole, phenetol, 2-methoxytoluene, 3-methoxytoluene, 4-methoxytoluene, 2,3-dimethylanisole, 2,4-dimethylanisole, diphenyl ether, etc.; aromatic esters such as phenyl acetate, phenyl propionate, methyl benzoate, ethyl benzoate, propyl benzoate, n-butyl benzoate, etc.; alicyclic ketones such as cyclohexanone, cyclooctanone, fenchone, etc.; alicyclic alcohols such as cyclohexanol, cyclooctanol, etc.; aliphatic ketones such as methyl ethyl ketone, dibutyl ketone, etc.; aliphatic alcohols such as butanol, hexanol, etc.; aliphatic ethers such as ethylene glycol dimethyl ether, ethylene glycol diethyl ether, propylene glycol 1-monomethyl ether acetate (PGMEA), etc.; etc. Above all, preferred are alkanes and aromatic hydrocarbons, and more preferred are aromatic hydrocarbons. In particular, phenylcyclohexane has a viscosity and a boiling point favorable for wet-process film formation.

One alone of those solvents may be used or two or more different types thereof may be used here, either singly or as combined in any desired manner and in any desired ratio.

The boiling point of the solvent is generally 80° C. or higher, preferably 100° C. or higher, more preferably 150° C. or higher, even more preferably 200° C. or higher. In general, the boiling point is 300° C. or lower, preferably 270° C. or lower, more preferably 250° C. or lower. When the boiling point is lower than the range, the film formation stability may worsen owing to solvent evaporation from the composition in wet-process film formation.

The solvent content is preferably 10 parts by weight or more, relative to 100 parts by weight of the composition, more preferably 50 parts by weight or more, even more preferably 80 parts by weigh for more. Also preferably, the content is 99.95 parts by weight or less, more preferably 99.9 parts by weight or less, even more preferably 99.8 parts by weight or less. In general, the thickness of the light-emitting layer is from 3 to 200 nm or so. However, when the solvent content is lower than the lower limit, the viscosity of the composition may be too high and the film formation workability may thereby worsen. On the other hand, when the content is higher than the upper limit, the thickness of the film to be formed through solvent removal after film formation could not be enough so that the film formation would be difficult.

The charge-transporting compound which the iridium complex compound-containing composition of the present invention may contain may be any one heretofore used in the art as a material for organic electroluminescent elements. For example, there are mentioned derivatives of benzene, naphthalene, anthracene, biphenyl, phenanthrene, pyridine, pyrimidine, triazine, carbazole, carboline, indolocarbazole, quinoline, phenanthroline and triphenylamine. Above all, preferred are derivatives of benzene, naphthalene, biphenyl, pyridine, pyrimidine, triazine, carbazole, carboline, quinoline and triphenylamine, since they are excellent in charge transportability and are highly stable and since, owing to high triplet energy thereof, the luminescent efficiency of the iridium complex compound of the present invention can be therefore high. Concretely, there are mentioned the compounds described in WO2012/096263, and above all, preferred are the compounds represented by the general formula (A) and the general formula (E) described in WO2012/096263. For use in a light-emitting layer, preferred are essentially hole-transporting compounds and essentially electron-transporting compounds.

One alone of those compounds may be used or two or more different types thereof may be used here, either singly or as combined in any desired manner and in any desired ratio.

The content of the charge-transporting compound in the iridium complex compound-containing composition of the present invention is generally 0.1 parts by weight or more, relative to 100 parts by weight of the composition, preferably 0.5 parts by weight or more, and is generally 50 parts by weight or less, preferably 30 parts by weight or less.

The content of the iridium complex compound in the iridium complex compound-containing composition of the present invention is generally 100% by weight or less relative to the charge-transporting compound din the iridium complex compound-containing composition, preferably 50% by weight or less, more preferably 30% by weight or less, and is generally 1% by weight or more, preferably 2% by weight or more, more preferably 5% by weight or more.

If desired, the iridium complex compound-containing composition of the present invention may contain any other compound in addition to the above-mentioned compounds, etc. For example, in addition to the above-mentioned solvent, the composition may contain any other solvent. The additional solvent includes, for example, amides such as N,N-dimethylformamide, N,N-dimethylacetamide, etc.; dimethylsulfoxide, etc. One alone of these may be used or two or more different types thereof may be used here, either singly or as combined in any desired manner and in any desired ratio.

[Organic Electroluminescent Element]

The organic electroluminescent element of the present invention has, as formed on a substrate, at least an anode and a cathode, and a light-emitting layer provided therebetween, and is characterized by having a layer formed using the composition of the present invention through wet-process film formation. Preferably, the layer formed through wet-process film formation is a light-emitting layer in the element.

FIG. 2 is a schematic view of a cross section showing a configuration example favorable for the organic electroluminescent element of the present invention. In FIG. 2, the reference number 1 indicates a substrate, the reference number 2 indicates an anode, the reference number 3 indicates a hole injection layer, the reference number 4 indicates a hole transport layer, the reference number 5 indicates a light-emitting layer, the reference number 6 indicates a hole-blocking layer, the reference number 7 indicates an electron transport layer, the reference number 8 indicates an electron injection layer, and the reference number 9 indicates a cathode.

[1] Substrate

The substrate 1 is a support of the organic electroluminescent element, for which used are a plate of quartz or glass, a metal plate, a metal foil, a plastic film or sheet, etc. Especially preferred are a glass plate, and a transparent synthetic resin plate of polyester, polymethacrylate, polycarbonate, polysulfone, etc. In case where a synthetic resin substrate is used, attention must be paid to gas-barrier performance thereof. When the gas-barrier performance of the substrate is too poor, then it is unfavorable since the organic electroluminescent element would be deteriorated owing to the outer air having passed through the substrate. Accordingly, a method of providing a dense silicon oxide film or the like on at least one side of the synthetic resin substrate to secure the gas-barrier performance is one preferred method.

[2] Anode

The anode 2 is provided on the substrate 1. The anode 2 plays a role in hole injection into the layer on the side of the light-emitting layer (hole injection layer 3, hole transport layer 4, light-emitting layer 5, etc.).

In general, the anode 2 is formed of a metal such as aluminium, gold, silver, nickel, palladium, platinum, etc.; a metal oxide such as indium and/or tin oxide, etc.; a metal halide such as copper iodide, etc.; carbon black; or a conductive polymer such as poly(3-methylthiophene), polypyrrole, polyaniline, etc.

In many cases and in general, the anode 2 is formed according to a sputtering method, a vacuum vapor deposition method or the like. On the other hand, in a case where an anode is formed using metal fine particles of silver or the like, fine particles of copper iodide or the like, carbon black, conductive metal oxide fine particles, conductive polymer fine powder or the like, the material may be dispersed in a suitable binder resin solution and may be applied onto the substrate 1 by coating to form the anode 2. Further, in a case of using a conductive polymer, a thin film may be formed directly on the substrate 1 through electrolytic polymerization, or a conductive polymer may be applied onto the substrate 1 by coating to form the anode 2 (Appl. Phys. Lett., Vol. 60, p. 2711, 1992).

The anode 2 generally has a single-layer structure, but if desired, may have a laminate structure comprising different types of materials.

The thickness of the anode 2 may vary depending on the needed transparency. In case where the transparency is needed, it is desirable that the visible light transmittance is generally 60% or more, preferably 80% or more. In this case, the thickness of the anode is generally 5 nm or more, preferably 10 nm or more, and is generally 1000 nm or less, preferably 500 nm or less or so. In case where the anode 2 may be opaque, the thickness thereof may be any arbitrary one, and the anode 2 may be the same as the substrate 1. Further, any different conductive material may be layered on the anode 2.

For the purpose of improving the hole injectability by removing the impurities having adhered to the anode and by controlling the ionization potential, it is desirable that the anode surface is processed through ultraviolet (UV)/ozone treatment, oxygen plasma treatment or argon plasma treatment.

[3] Hole Injection Layer

The hole injection layer 3 is a layer for transporting holes from the anode 2 to the light-emitting layer 5 and is, in general, formed on the anode 2. The method for forming the hole injection layer 3 in the present invention may be a vacuum vapor deposition method or a wet-process film formation method, and is not specifically defined. From the viewpoint of reducing dark spots, it is desirable that the hole injection layer 3 is formed according to a wet-process film formation method. The thickness of the hole injection layer 3 is in a range of generally 5 nm or more, preferably 10 nm or more, and is generally 1000 nm or less, preferably 500 nm or less.

<Formation of Hole Injection Layer Through Wet-Process Film Formation>

In case where the hole injection layer 3 is formed through wet-process film formation, in general, materials to constitute the hole injection layer 3 are mixed with a suitable solvent (solvent for hole injection layer) to prepare a composition for film formation (composition for forming hole injection layer), and the composition for forming hole injection layer is applied onto a layer that corresponds to an underlayer below the hole injection layer 3 (in general, anode) for film formation thereon according to a suitable method, and dried to form the hole injection layer 3.

(Hole-Transporting Compound)

The composition for forming hole injection layer generally contains a hole-transporting compound as a constitutive material of the hole injection layer, and a solvent. The hole-transporting compound is generally used for the hole injection layer of organic electroluminescent elements. The compound may be any one having hole transportability, including a high-molecular compound such as polymer or the like as well as a low-molecular compound such as monomer or the like, but is preferably a polymer compound.

As the hole-transporting compound, preferred is a compound having an ionization potential of from 4.5 eV to 6.0 eV, from the viewpoint of the barrier against charge injection from the anode 2 to the hole injection layer 3. Examples of the hole-transporting compound include aromatic amine derivatives, phthalocyanine derivatives, porphyrin derivatives, oligothiophene derivatives, polythiophene derivatives, benzylphenyl derivatives, compounds with a tertiary amine bonded via a fluorene group, hydrazone derivatives, silazane derivatives, silanamine derivatives, phosphamine derivatives, quinacridone derivatives, polyaniline derivatives, polypyrrole derivatives, polyphenylenevinylene derivatives, polythienylenevinylene derivatives, polyquinoline derivatives, polyquinoxaline derivatives, carbon, etc.

Derivatives as referred to in the present invention are as follows. Described as one example, aromatic amine derivatives include aromatic amines themselves and compounds having an aromatic amine as the main skeleton thereof, and may be either polymers or monomers.

The hole-transporting material for use as the material of the hole injection layer 3 may contain any one alone of those compounds, or may contain two or more different types of those compounds. In case where the layer contains two or more different types of such hole-transporting materials, the combination thereof is not specifically defined. Preferably, the layer contains one or more aromatic tertiary amine polymer compounds and one or more other hole-transporting compounds, as combined.

Of the above-exemplified ones, preferred are aromatic amine compounds from the viewpoint of the non-crystallinity and the visible light transmittance thereof, and more preferred are aromatic tertiary amine compounds. Here, the aromatic tertiary amine compounds are compounds having an aromatic tertiary amine structure and include compounds having an aromatic tertiary amine-derived group.

The aromatic tertiary amine compounds are not specifically defined in point of the type thereof, but from the viewpoint of uniform light emission owing to the surface-smoothing effect thereof, more preferred are polymer compounds having a weight-average molecular weight of 1000 or more and 1000000 or less (polymerization-type compounds with continuing recurring units). As preferred examples of the aromatic tertiary amine polymer compound, mentioned are polymer compounds having a recurring unit represented by the following formula (IV).

[Chem. 19]

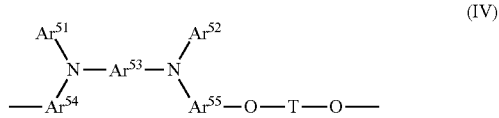

(In the formula (IV), $Ar^{51}$ and $Ar^{52}$ each independently represent an aromatic hydrocarbon group optionally having a substituent, or an aromatic heterocyclic group optionally having a substituent. $Ar^{53}$ to $Ar^{55}$ each independently represent an aromatic hydrocarbon group optionally having a substituent, or an aromatic heterocyclic group optionally having a substituent. T represents one linking group selected from the following linking groups. Of Ar$^{51}$ to Ar$^{55}$, two groups bonding to the same N atom may bond to each other to form a ring.)

<Linking Groups>

[Chem. 20]

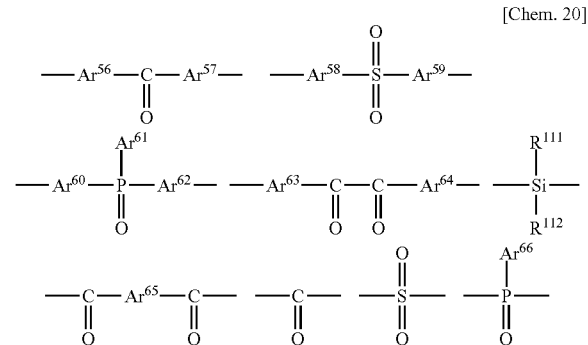

(In the above formulae, Ar$^{56}$ to Ar$^{66}$ each independently represent an aromatic hydrocarbon group optionally having a substituent, or an aromatic heterocyclic group optionally having a substituent. R$^{111}$ and R$^{112}$ each independently represent a hydrogen atom or an arbitrary substituent.)

As the aromatic hydrocarbon group and the aromatic heterocyclic group for Ar$^{51}$ to Ar$^{66}$ in the formula (IV) and the above-mentioned linking groups, preferred are residues having two free atomic valences of a benzene ring, a naphthalene ring, a phenanthrene ring, a thiophene ring and a pyridine ring, from the viewpoint of the solubility, heat resistance and hole injection/transport capability of the polymer compounds; and more preferred are residues having two free atomic valences of a benzene ring and a naphthalene ring.

The aromatic hydrocarbon group and the aromatic heterocyclic group for Ar$^{51}$ to Ar$^{66}$ may further have a substituent. The molecular weight of the substituent is, in general, preferably 400 or less, more preferably 250 or less or so. As the substituent, preferred are an alkyl group, an alkenyl group, an alkoxy group, an aromatic hydrocarbon group, an aromatic heterocyclic group, etc.

In case where R$^{111}$ and R$^{112}$ each are a substituent, the substituent includes an alkyl group, an alkenyl group, an alkoxy group, a silyl group, a siloxy group, an aromatic hydrocarbon group, an aromatic heterocyclic group, etc.

As the hole-transporting compound, also preferred is a conductive polymer (PEDOT/PSS) which is a polythiophene derivative and which is prepared through polymerization of 3,4-ethylenedioxythiophene in a high-molecular-weight polystyrenesulfonic acid. The end of the polymer may be capped with methacrylate or the like for use herein.

As the hole-transporting compound, also usable here is a compound having an insolubilized group as described in the section of "hole transport layer" given hereinunder.

The concentration of the hole-transporting compound in the composition for forming hole injection layer may be any one, not markedly detracting from the advantageous effects of the present invention. The concentration is typically 0.01% by weight or more, preferably 0.1% by weight or more, more preferably 0.5% by weight or more, from the viewpoint of the uniformity of the film thickness, but on the other hand, the concentration is typically 70% by weight or less, preferably 60% by weight or less, more preferably 50% by weight or less. When the concentration is too high, then the film thickness may be uneven; but when too low, then the hole injection layer formed would have defects.

<Electron-Accepting Compound>

Preferably, the composition for forming hole injection layer contains an electron-accepting compound as the constitutive material of the hole injection layer.

The electron-accepting compound is preferably a compound having an oxidation power and having the ability to accept one electron from the above-mentioned hole-transporting compound. Concretely, as the electron-accepting compound, preferred is a compound having an electron affinity of 4 eV or more, more preferably 5 eV or more.

As the electron-accepting compound of the type, for example, there are mentioned one or more compounds selected from a group consisting of triarylboron compounds, metal halides, Lewis acids, organic acids, onium salts, salts of arylamine and metal halide, and salts of arylamine and Lewis acid. More concretely, the electron-accepting compounds include high-valent inorganic compounds such as iron(III) chloride (JP-A 11-251067), ammonium peroxodisulfate, etc.; cyano compounds such as tetracyanoethylene, etc.; aromatic boron compounds such as tris(pentafluorophenyl)borane (JP-A 2003-31365), etc.; onium salts substituted with an organic group (WO2005/089024); fullerene derivatives; iodine; sulfonate ions such as polystyrenesulfonate ions, alkylbenzenesulfonate ions, camphorsulfonate ions, etc.

These electron-accepting compounds may increase the electroconductivity of the hole injection layer, as oxidizing the hole-transporting compound in the layer.

The content of the electron-accepting compound relative to the hole-transporting compound in the hole injection layer or in the composition for forming hole injection layer is generally 0.1 mol % or more, preferably 1 mol % or more, but is generally 100 mol % or less, preferably 40 mol % or less.

(Solvent)

At least one solvent in the composition for forming hole injection layer that is used in a wet-process film formation method is preferably a compound capable of dissolving the constitutive materials of the hole injection layer. The boiling point of the solvent is generally 110° C. or higher, preferably 140° C. or higher, more preferably 200° C. or higher, and is generally 400° C. or lower, preferably 300° C. or lower. When the boiling point of the solvent is too low, then the drying speed would be too high so that the film quality may worsen. On the other hand, when the boiling point of the solvent is too high, then the temperature in the drying step must be high, therefore often having some negative influence on the other layers and the substrate.

As the solvent, for example, there are mentioned ether solvents, ester solvents, aromatic hydrocarbon solvents, amide solvents, etc.

The ether solvents include, for example, aliphatic ethers such as ethylene glycol dimethyl ether, ethylene glycol diethyl ether, propylene glycol 1-monomethyl ether acetate (PGMEA), etc.; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, etc.

The ester solvents include, for example, aromatic esters such as phenyl acetate, phenyl propionate, methyl benzoate, ethyl benzoate, propyl benzoate, n-butyl benzoate, etc.

The aromatic hydrocarbon solvents include, for example, toluene, xylene, cyclohexylbenzene, 3-isopropylbiphenyl, 1,2,3,4-tetramethylbenzene, 1,4-diisopropylbenzene, cyclohexylbenzene, methylnaphthalene, etc. The amide solvents include, for example, N,N-dimethylformamide, N,N-dimethylacetamide, etc.

In addition, dimethyl sulfoxide or the like is also usable here. One alone or two or more different types of those solvents may be used here either singly or as combined in any desired manner and in any desired ratio.

[Method of Film Formation]

After the composition for forming hole injection layer has been prepared, the composition is applied onto the layer that corresponds to the underlayer below the hole injection layer 3 (in general, anode 2) for film formation thereon according to wet-process film formation, and dried to form the hole injection layer 3.

The temperature in the coating step is preferably 10° C. or higher and is preferably 50° C. or lower for preventing the film from having defects owing to crystal formation in the composition.

The relative humidity in the coating step is not specifically defined so far as it does not markedly detract from the advantageous effects of the present invention, but is generally 0.01 ppm or more and is generally 80% or less.

After coating, the film of the composition for forming hole injection layer is dried generally by heating or the like. Examples of the heating means for use in the heating step include clean oven, hot plate, etc.

The heating temperature in the heating step may be any one not markedly detracting from the advantageous effects of the present invention, and preferably, the coating film is heated at a temperature not lower than the boiling point of the solvent used in the composition for forming hole injection layer. In case where a mixed solvent of two or more different types of solvents are used for the hole injection layer, it is desirable that the coating film is heated at a temperature not lower than the boiling point of at least one solvent of the mixed solvent. In consideration of boiling point elevation, it is desirable that the coating film is heated at 120° C. or higher and at 410° C. or lower in the heating step.

In the heating step, the heating time is not specifically defined so far as the heating temperature is not lower than the boiling point of the solvent in the composition for forming hole injection layer and the coating film is not sufficiently insolubilized; however, the heating time is preferably 10 seconds or more and is generally 180 minutes or less. When the heating time is too long, then the components of the other layers may diffuse; but when too short, the hole injection layer would be inhomogeneous. The heating may be carried out two times.

<Formation of Hole Injection Layer According to Vacuum Vapor Deposition Method>

In case where the hole injection layer 3 is formed through vacuum vapor deposition, one or more of the constitutive materials of the hole injection layer 3 (above-mentioned hole-transporting compound, electron-accepting compound, etc.) are put into crucible set in a vacuum chamber (in case where two or more different types of materials are used, the materials are individually put in different crucibles), the vacuum chamber is degassed down to $10^{-4}$ Pa or so via a suitable vacuum pump, then the crucibles are heated (in case where two or more different types of materials are used, the respective crucibles are heated) to thereby evaporate the solvent under control of the evaporation amount thereof (in case where two or more different types of materials are used, each material is evaporated under independent control of the evaporation amount thereof), and thus the hole injection layer 3 is formed on the anode 2 on the substrate put to face the crucibles. In case where two or more different types of materials are used, a mixture thereof may be put in one crucible, and may be heated and evaporated to form the hole injection layer 3.

Not markedly detracting from the advantageous effects of the present invention, the vacuum degree in evaporation is not specifically defined. The vacuum degree in evaporation is typically $0.1 \times 10^{-6}$ Torr ($0.13 \times 10^{-4}$ Pa) or more and $9.0 \times 10^{-6}$ Torr ($12.0 \times 10^{-4}$ Pa) or less. Not markedly detracting from the advantageous effects of the present invention, the evaporation rate is not specifically defined. The evaporation rate is typically 0.1 angstrom/sec or more and is 5.0 angstrom/sec or less.

[4] Hole Transport Layer

The hole transport layer 4 may be formed on the hole injection layer 3 when the hole injection layer is present, but when the hole injection layer 3 is absent, the hole transport layer 4 may be formed on the anode 2. The organic electroluminescent element of the present invention may have a configuration not having the hole transport layer.

The method for formation of the hole transport layer 4 is not specifically defined, and the layer may be formed according to a vacuum vapor deposition method or a wet-process film formation method. Preferably, the hole transport layer 4 is formed according to a wet-process film formation method from the viewpoint of reducing dark spots.

The material for forming the hole transport layer 4 is preferably a material having high hole transportability and capable of efficiently transporting the injected holes. Consequently, it is desirable that the material for forming the hole transport layer 4 has a small ionization potential, is highly transparent to visible light, has a large hole mobility, is excellent in stability and generates few impurities to be traps in production and during use. Kept in adjacent to the light-emitting layer 5, in many cases, it is desirable that the hole transport layer 4 does not quench the emission from the light-emitting layer 5 and does not form an exciplex with the light-emitting layer 5 to lower the luminescent efficiency.

The material for the hole transport layer 4 may be any and every material heretofore used as the constitutive material for hole transport layer, and includes, for example, those exemplified as the hole-transporting compound for use in the above-mentioned hole injection layer 3. As the material, in addition, there are further mentioned arylamine derivatives, fluorene derivatives, spiro derivatives, carbazole derivatives, pyridine derivatives, pyrazine derivatives, pyrimidine derivatives, triazine derivatives, quinoline derivatives, phenanthroline derivatives, phthalocyanine derivatives, porphyrin derivatives, silol derivatives, oligothiophene derivatives, condensed polycyclic aromatic derivatives, metal complexes, etc.

In addition, for example, there are further mentioned polyvinylcarbazole derivatives, polyarylamine derivatives, polyvinyltriphenylamine derivatives, polyfluorene derivatives, polyarylene derivatives, tetraphenylbenzidine-containing polyarylene ether sulfone derivatives, polyarylenevinylene derivatives, polysiloxane derivatives, polythiophene derivatives, poly(p-phenylenevinylene) derivatives, etc. These may be any of alternate copolymers, random polymers, block polymers or graft copolymers. In addition, also employable are polymers and so-called dendrimers having a branched main chain or having 3 or more end parts.

Above all, preferred are polyarylamine derivatives and polyarylene derivatives.

As polyarylamine derivatives, preferred are polymers containing a recurring unit represented by the following formula (V). Especially preferred are polymers comprising the recurring unit represented by the following formula (V), in which $Ar^a$ or $Ar^b$ in each recurring unit may be the same or different.

[Chem. 21]

(In the formula (V), $Ar^a$ and $Ar^b$ each independently represent an aromatic hydrocarbon group or an aromatic heterocyclic group, which may have a substituent.)

The optionally-substituted aromatic hydrocarbon group includes residues having one or two free atomic valences of 6-membered monocyclic or 2 to 5-condensed rings or those formed by linking two or more such rings through direct bonding, such as residues having one or two free atomic valences of a benzene ring, a naphthalene ring, an anthracene ring, a phenanthrene ring, a perylene ring, a tetracene ring, a pyrene ring, a benzopyrene ring, a chrysene ring, a triphenylene ring, an acenaphthene ring, a fluoranthene ring, a fluorene ring, etc.

The optionally-substituted aromatic heterocyclic group includes residues having one or two free atomic valences of 5- or 6-membered monocyclic or 2 to 4-condensed rings or those formed by linking two or more such rings through direct bonding, such as residues having one or two free atomic valences of a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a phenanthridine ring, a benzimidazole ring, a perimidine ring, a quinazoline ring, a quinazolinone ring, an azurene ring, etc.

From the viewpoint of solubility in organic solvent and heat resistance, it is desirable that $Ar^a$ and $Ar^b$ are each independently a residue having one or two free atomic valences of a ring selected from a benzene ring, a naphthalene ring, an anthracene ring, a phenanthrene ring, a triphenylene ring, a pyrene ring, a thiophene ring, a pyridine ring and a fluorene ring, or a group formed by linking two or more benzene rings (for example, a biphenyl group (biphenylene group) or a terphenyl group (terphenylene group)).

Above all, preferred are benzene, biphenyl and fluorene having one or two free atomic valences.

The substituent that the aromatic hydrocarbon group and the aromatic heterocyclic group of $Ar^a$ and $Ar^b$ may have includes an alkyl group, an alkenyl group, an alkynyl group, an alkoxy group, an aryloxy group, an alkoxycarbonyl group, a dialkylamino group, a diarylamino group, an acyl group, a halogen atom, a haloalkyl group, an alkylthio group, an arylthio group, a silyl group, a siloxy group, a cyano group, an aromatic hydrocarbon group, an aromatic heterocyclic group, etc.

As polyarylamine derivatives, also mentioned are polymers having an arylene group such as an aromatic hydrocarbon group or an aromatic heterocyclic group as the recurring unit therein, which may have a substituent as exemplified for $Ar^a$ and $Ar^b$ in the above-mentioned formula (V). As polyarylamine derivatives, preferred are polymers having at least one of recurring units represented by the following formula (VI) and the following formula (VII).

[Chem. 22]

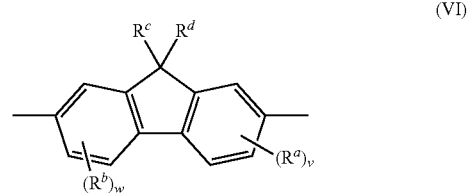

(In the formula (VI), $R^a$, $R^b$, $R^c$ and $R^d$ each independently represent an alkyl group, an alkoxy group, a phenylalkyl group, a phenylalkoxy group, a phenyl group, a phenoxy group, an alkylphenyl group, an alkoxyphenyl group, an alkylcarbonyl group, an alkoxycarbonyl group, or a carboxy group.

v and w each independently indicate an integer of from 0 to 3. When v or w is 2 or more, then multiple $R^a$s or $R^b$s contained in one molecule may be the same or different, and the neighboring $R^a$s or $R^b$s may form a ring.)

[Chem. 23]

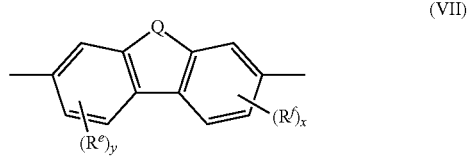

(In the formula (VII), $R^e$ and $R^f$ each independently have the same meaning as those of $R^a$, $R^b$, $R^c$ or $R^d$ in the formula (VI).

x and y each independently indicate an integer of from 0 to 3. When x or y is 2 or more, then multiple $R^e$s or $R^f$s contained in one molecule may be the same or different, and the neighboring $R^e$s or $R^f$s may form a ring. Q represents an atom or an atomic group to constitute a 5-membered ring or a 6-membered ring.)

Specific examples of Q include —O—, —BR—, —NR—, —SiR$_2$—, —PR—, —SR—, —CR$_2$— or a group formed by bonding any of these. Here, R means a hydrogen atom or an arbitrary organic group. The arbitrary organic group in the present invention may be any group containing at least one carbon atoms.

As polyarylene derivatives, also preferred are those further having a recurring unit represented by the following formula (VIII), in addition to at least one recurring unit of the above-mentioned formula (VI) and the above-mentioned formula (VII).

[Chem. 24]

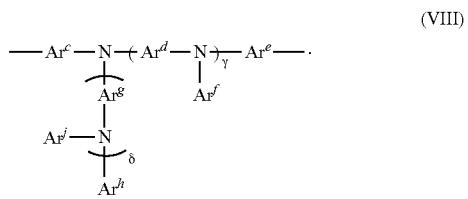

(VIII)

(In the formula (VIII), Ar$^c$ to Ar$^h$ and Ar$^j$ each independent represent an aromatic hydrocarbon group or an aromatic heterocyclic group, which may have a substituent. γ and δ each independently indicate 0 or 1.)

Specific examples of Ar$^c$ to Ar$^h$ and Ar$^j$ are the same as those of Ar$^a$ and Ar$^b$ in the formula (V).

As specific examples of the above-mentioned formulae (VI) to (VIII) and specific examples of polyarylene derivatives, there are mentioned those described in JP-A 2008-98619.

In case where the hole transport layer 4 is formed according to a wet-process film formation method, a composition for forming hole transport layer is first prepared, then processed for film formation and dried under heat, like in the case of forming the above-mentioned hole injection layer 3.

The composition for forming hole transport layer contains a solvent in addition to the above-mentioned hole-transporting compound. The solvent to be used is the same as that used in the composition for forming hole injection layer. In addition, the film formation condition and the heating and drying condition are also the same as in the case of forming the hole injection layer 3. When the hole transport layer is formed according to a vacuum vapor deposition method, the film formation condition and others are also the same as in the case of forming the hole injection layer 3. The hole transport layer 4 may contain various types of light-emitting material, electron-transporting compound, binder resin, coating improver and the like, in addition to the above-mentioned hole-transporting compound.

The hole transport layer 4 is preferably a layer formed by insolubilizing a compound having an insolubilizable group (hereinafter referred to as "insolubilizable compound") from the viewpoint of heat resistance and film formability. The insolubilizable compound is a compound having an insolubilizable group, and forms an insolubilized polymer through insolubilization.

The insolubilizable group is a group capable of reacting under heat and/or through irradiation with active energy rays, and is a group having an effect of lowering the solubility of the compound after reaction in organic solvent and water as compared with that before reaction. In the invention, the insolubilizable compound is preferably a leaving group or a crosslinking group.

The leaving group means a group that dissociates from the aromatic hydrocarbon ring to which it bonds, at 70° C. or higher, and exhibits solubility in solvent. Here, exhibiting solubility in solvent means that the compound dissolves in toluene in an amount of 0.1% by weight or more at room temperature in the original state thereof before reaction under heat and/or through irradiation with active energy rays, and the solubility of the compound in toluene is preferably 0.5% by weight or more, more preferably 1% by weight or more.

Preferably, the leaving group is a thermally-dissociable group not forming a polar group on the side of the aromatic hydrocarbon ring, and is more preferably a group capable of undergoing thermal dissociation through reverse Diels-Alder reaction. Also preferred is a group that may thermally dissociate at 100° C. or higher, and preferred is a group that may thermally dissociate at 300° C. or lower.

Examples of the crosslinking group include groups derived from cyclic ethers such as oxetane, epoxy, etc.; unsaturated double bond-derived groups such as vinyl group, trifluorovinyl group, styryl group, acryl group, methacryloyl, cinnamoyl, etc.; benzocyclobutene-derived group, etc.

The insolubilizable compound may be any of monomer, oligomer and polymer. One alone or two or more different types of insolubilizable compounds may be used here either singly or as combined in any desired manner and in any desired ratio.

As the insolubilizable compound, preferably used here is a hole-transporting compound having a crosslinking group. Examples of the hole-transporting compound include nitrogen-containing aromatic compound derivatives such as pyridine derivatives, pyrazine derivatives, pyrimidine derivatives, triazine derivatives, quinoline derivatives, phenanthroline derivatives, carbazole derivatives, phthalocyanine derivatives, porphyrin derivatives, etc.; triphenylamine derivatives; silol derivatives; oligothiophene derivatives, condensed polycyclic aromatic derivatives, metal complexes, etc. Above all, preferred are nitrogen-containing aromatic derivatives such as pyridine derivatives, pyrazine derivatives, pyrimidine derivatives, triazine derivatives, quinoline derivatives, phenanthroline derivatives, carbazole derivatives, etc.; triphenylamine derivatives, silol derivatives, condensed polycyclic aromatic derivatives, metal complexes, etc.; and more preferred are triphenylamine derivatives.

For forming the hole transport layer 4 by insolubilizing the insolubilizable compound, in general, the insolubilizable compound is dissolved or dispersed in a solvent to prepare a composition for forming hole transport layer, and the composition is processed for film formation and insolubilized according to a wet-process film formation method.

The composition for forming hole transport layer may further contain a coating improver such as a leveling agent, a defoaming agent, etc.; an electron-accepting compound; a binder resin, etc.

The composition for forming hole transport layer contains the insolubilizing compound generally in an amount of 0.01% by weight or more, preferably 0.05% by weight or more, more preferably 0.1% by weight or more, and generally in an amount of 50% by weight or less, preferably 20% by weight or less, more preferably 10% by weight or less.

The composition for forming hole transport layer that contains the insolubilizing compound in the concentration as above is applied onto the underlayer (in general, hole injection layer 3) for film formation thereon, and then exposed to heat and/or light or the like active energy irradiation to thereby insolubilize the insolubilizable compound.

The condition such as temperature and humidity in film formation is the same as that in the case of wet-process film formation for the hole injection layer 3. The heating method after film formation is not specifically defined. The heating temperature condition is generally 120° C. or higher, and is preferably 400° C. or lower. The heating time is generally 1 minute or more and is preferably 24 hours or less. The heating means is not specifically defined. The laminate having the formed layer may be put on a hot plate, or may be heated in an oven. For example, the laminate may be heated on a hot plate at 120° C. or higher for 1 minute or more.

For irradiation with electromagnetic energy such as light or the like, there may be mentioned a method of irradiation using an ultra-high-pressure mercury lamp, a high-pressure mercury lamp, etc.; a method of irradiation using a mask aligner or a conveyor-type photoirradiation apparatus that has the above-mentioned light source as a built-in device inside it, etc.

The thickness of the hole transport layer 4 thus formed is generally 5 nm or more, preferably 10 nm or more, and is generally 300 nm or less, preferably 100 nm or less.

[5] Light-Emitting Layer

The light-emitting layer 5 is generally provided on the hole transport layer 4. The light-emitting layer 5 is, as sandwiched between the electrodes given an electric field, excited though recombination of the holes as injected thereinto from the anode 2 via the hole injection layer 3 and the electrons as injected thereinto from the cathode 9 via the electron transport layer 7, and is a layer to be a main light-emitting source in the element. Preferably, the light-emitting layer 5 contains a light-emitting material (dopant) and one or more host materials. The light-emitting layer 5 may be formed according to a vacuum vapor deposition method, but is preferably a layer formed according to a wet-process film formation method using the composition for organic electroluminescent elements of the present invention.

Here, the wet-process film formation method is a method of film formation in a wet process using a composition containing a solvent, as described above, including a spin coating method, a dip coating method, a die coating method, a bar coating method, a blade coating method, a roll coating method, a spray coating method, a capillary coating method, an inkjet method, a screen printing method, a gravure printing method, a flexographic printing method, etc.

Within a range not detracting from the performance of the present invention, the light-emitting layer 5 may contain any other material and component. In general, in a case where the same materials are used in organic electroluminescent elements, when the thickness between the electrodes is thinner, then the effective electric field could be large and therefore the current to be injected could increase and, as a result, the driving voltage may lower in the case. Consequently, a thin total thickness between electrodes could lower the driving voltage for the organic electroluminescent element; however, when too thin, there may occur short-circuiting owing to electrode-assigned projections such as ITO or the like, and therefore, some thickness is needed.

In the present invention, in case where the element has any other organic layers than the light-emitting layer 5, such as the hole injection layer 3, the electron transport layer 7 to be mentioned below and others, the total thickness of light-emitting layer 5 as combined with the other organic layers such as the hole injection layer 3, the electron transport layer 7 and others is generally 30 nm or more, preferably 50 nm or more, more preferably 100 nm or more, and is generally 1000 nm or less, preferably 500 nm or less, more preferably 300 nm or less. In case where the electroconductivity of the other layers than the light-emitting layer 5, such as the hole injection layer 3 and the electron injection layer 8 to be mentioned below is high, then the charge amount to be injected into the light-emitting layer 5 may increase, and therefore, for example, it is possible to thicken the hole injection layer 3 and to thin the light-emitting layer 5 to thereby lower the driving voltage while the total thickness is kept in some degree.

Accordingly, the thickness of the light-emitting layer 5 is generally 10 nm or more, preferably 20 nm or more, and is generally 300 nm or less, preferably 200 nm or less. In case where the element of the present invention has the light-emitting layer 5 alone between the two electrodes of the anode and the cathode, the thickness of the light-emitting layer 5 is generally 30 nm or more, preferably 50 nm or more, and is generally 500 nm or less, preferably 300 nm or less.

[6] Hole-Blocking Layer

The hole-blocking layer 6 is formed as laminated to be adjacent to the interface on the cathode side of the light-emitting layer 5. In particular, in case where a phosphor material is used as the light-emitting substance or a blue-emitting material is used, it is effective to provide the hole-blocking layer 6. The hole-blocking layer 6 has the function of trapping holes and electrons in the light-emitting layer 5 to thereby increase the luminescent efficiency of the element. Specifically, the hole-blocking layer 6 plays a role in blocking the holes moving from the light-emitting layer 5 from reaching the electron transport layer 7, thereby increasing the probability of recombination with electrons in the light-emitting layer 5 and trapping the formed excitons inside the light-emitting layer 5, and a role in efficiently transporting the electrons injected from the electron transport layer 7 toward the light-emitting layer 5.

Regarding the necessary physical properties thereof, the material to constitute the hole-blocking layer 6 is desired to have a high electron mobility, a low hole mobility, a large energy gap (difference between HOMO and LUMO) and a high excitation triplet energy level (T1).

The hole-blocking layer material satisfying the requirements includes mixed ligand complexes such as bis(2-methyl-8-quinolinolato)(phenolato)aluminium, bis(2-methyl-8-quinolinolato)(triphenylsilanolato)aluminium, etc.; metal complexes such as bis(2-methyl-8-quinolato)aluminium-μ-oxo-bis(2-methyl-8-quinolinolato)aluminium binuclear metal complex, etc.; styryl compounds such as distyrylbiphenyl derivatives, etc. (JP-A 11-242996); triazole derivatives such as 3-(4-biphenylyl)-4-phenyl-5(4-tert-butylphenyl)-1,2,4-triazole, etc. (JP-A 7-41759); phenanthroline derivatives such as bathocuproin, etc. (JP-A 10-79297), etc.

Further, compounds having at least one pyridine ring substituted at the 2,4,6-positions, as described in WO2005/022962, are also preferred as the hole-blocking material. The thickness of the hole-blocking layer 6 is generally 0.3 nm or more, preferably 0.5 nm or more, and is generally 100 nm or less, preferably 50 nm or less. The hole-blocking layer 6 may be formed according to the same method as that for the hole injection layer 3, but in general, a vacuum vapor deposition method is employed.

[7] Electron Transport Layer

The electron transport layer 7 is a layer provided between the hole-blocking layer 6 and the electron injection layer 8 for further improving the luminescent efficiency of the element. The electron transport layer 7 is formed of a compound capable of transporting the electrons injected from the cathode 9 efficiently toward the light-emitting layer 5 between the electrodes given an electric field. The electron-transporting compound to be used for the electron transport layer 7 must be a compound having a high electron injection efficiency from the cathode 9 or the electron injection layer 8, having a high electron mobility, and capable of efficiently transporting the injected electrons.

The material satisfying the requirements includes metal complexes such as aluminium complex of 8-hydroxyquinoline, etc. (JP-A 59-194393), 10-hydroxybenzo [h]quinoline metal complexes, oxadiazole derivatives, distyrylbiphenyl derivatives, silol derivatives, 3- or 5-hydroxyflavone metal complexes, benzoxazole metal complexes, benzothiazole metal complexes, trisbenzimidazolylbenzene (U.S. Pat. No. 5,645,948), quinoxaline compounds (JP-A 6-207169), phenanthroline derivatives (JP-A 5-331459), 2-t-butyl-9,10-N,N-dicyanoanthraquinonediimine, n-type hydrogenated amorphous silicon carbide, n-type zinc sulfide, n-type zinc selenide, etc.

Regarding the thickness of the electron transport layer 7, the lower limit is generally 1 nm, preferably 5 nm or so, and the upper limit is generally 300 nm, preferably 100 nm or so.

Like the hole injection layer 3, the electron transport layer 7 may be formed according to a wet-process film formation method or a vacuum vapor deposition method, but in general, a vacuum vapor deposition method is employed.

[8] Electron Injection Layer

The electron injection layer 8 plays a role in efficiently injecting the electrons injected from the cathode 9, into the light-emitting layer 5. For efficient electron injection, the material to form the electron injection layer 8 is preferably a metal having a low work function. Used here are alkali metals such as sodium, cesium, etc., and alkaline earth metals such as barium, calcium, etc. The thickness of the electron injection layer 8 is preferably from 0.1 to 5 nm.

Inserting an ultrathin insulating film (0.1 to 5 nm) of LiF, $MgF_2$, $Li_2O$, $Cs_2CO_3$ or the like into the interface between the cathode 9 and the electron transport layer 7 is an effective method for increasing the efficiency of the element (Appl. Phys. Lett., Vol. 70, p. 152, 1997; JP-A 10-74586; IEEE Trans. Electron. Devices, Vol. 44, p. 1245, 1997; SID 04 Digest, p. 154).

In addition, also preferred is doping an organic electron-transporting material such as typically a nitrogen-containing heterocyclic compound such as basophenanthroline or the like, or a metal complex such as an aluminium complex of 8-hydroxyquinoline or the like, with an alkali metal such as sodium, potassium, cesium, lithium, rubidium or the like (as described in JP-A 10-270171, 2002-100478, 2002-100482, etc.), as capable of satisfying both good electron injection/transport capability and excellent film quality. In this case, the film thickness is generally 5 nm or more, preferably 10 nm or more and is generally 200 nm or less, preferably 100 nm or less.

Like the light-emitting layer 5, the electron injection layer 8 is formed according to a wet-process film formation method or a vacuum vapor deposition method. The vacuum vapor deposition method is as follows. A vapor deposition source is put into a crucible or a metal boat set in a vacuum chamber, then the vacuum chamber is degassed to $10^{-4}$ Pa or so via a suitable vacuum pump. Subsequently, the crucible or the metal boat is heated to vaporize the source material therein to thereby form an electron injection layer on the substrate arranged to face the crucible or the metal boat.

Alkali metal vapor deposition is attained, using an alkali metal dispenser prepared by filling an alkali metal chromate and a reducing agent in Nichrome. The dispenser is heated in a vacuum chamber whereby the alkali metal chromate is reduced and the alkali metal is thereby evaporated. In case of co-evaporation of an organic electron-transporting material and an alkali metal, the organic electron-transporting material is put in the crucible arranged inside the vacuum chamber, then the vacuum chamber is degassed with a suitable vacuum pump to $10^{-4}$ Pa or so, and the crucible and the dispenser are heated for evaporation at the same time to thereby form the intended electron injection layer on the substrate arranged to face the crucible and the dispenser.

In this, the two are co-deposited uniformly in the thickness direction of the electron injection layer 8, but may have a concentration profile in the thickness direction.

[9] Cathode

The cathode 9 plays a role in injecting electrons into the layer on the side of the light-emitting layer (electron injection layer 8 or light-emitting layer 5). As the material for the cathode 9, the material for use for the above-mentioned anode 2 may be used; however, for efficient electron injection, preferred is a metal having a low work function. Suitable metals such as tin, magnesium, indium, calcium, aluminium or silver or their alloys may be used. Specific examples are low-work-function alloy electrodes of magnesium-silver alloy, magnesium-indium alloy, aluminium-lithium alloy, etc.

The thickness of the cathode 9 is generally the same as that of the anode 2. For the purpose of protecting the cathode formed of a low-work-function metal, a metal layer having a high work function and is stable to air is preferably layered on the cathode, whereby the stability of the element could increase. For this purpose, metals are used, such as aluminium, silver, copper, nickel, chromium, gold, platinum, etc.

[10] Other Constituent Layers

In the above, elements having the layer configuration shown in FIG. 2 have been mainly described; however, the organic electroluminescent element of the present invention may have, between the anode 2 and the cathode 9 and the light-emitting layer 5 therein, any other layers in addition to the above-mentioned layers, not detracting from the performance of the device, or any of the layers except the light-emitting layer 5 may be omitted.

For the same purpose as that for the hole-blocking layer 6, it may also be effective to provide an electron-blocking layer between the hole-transporting layer 4 and the light-emitting layer 5. The electron-blocking layer plays a role in blocking the electrons moving from the light-emitting layer 5 from reaching the hole transport layer 4, thereby increasing the probability of recombination with holes in the light-emitting layer 5 and trapping the formed excitons inside the light-emitting layer 5, and a role in efficiently transporting the holes injected from the hole transport layer 4 toward the light-emitting layer 5.

Regarding the necessary properties thereof, the electron-blocking layer is desired to have a high hole transportability, a large energy gap (difference between HOMO and LUMO) and a high excitation triplet energy level (T1). In case where the light-emitting layer 5 is formed according to a wet-process film formation method, it is desirable that the electron-blocking layer is formed also according to a wet-process film formation method as facilitating the element production.

Consequently, it is desirable that the electron-blocking layer also has wet-process film formation compatibility, and as the material for use for the electron-blocking layer of the type, there are mentioned copolymers of dioctylfluorene and triphenylamine such as typically F8-TFB (WO2004/084260), etc.

An opposite structure to FIG. 2 may also be employed here, or that is, on the substrate 1, a cathode 9, an electron injection layer 8, an electron transport layer 7, a hole-blocking layer 6, a light-emitting layer 5, a hole transport layer 4, a hole injection layer 3 and an anode 2 may be layered in that order; the organic electroluminescent element of the present invention may be arranged between two substrates of which at least one has high transparency.

Further, the present invention may employ a layered structure comprising a plurality of the layer constructions shown in FIG. 2 (laminate structure of multiple light emission units). In this case, in place of the interlayer between the unit layer constructions (light emission units) (when the anode is ITO and the cathode is Al, in place of both the two layers), for example, $V_2O_5$ or the like may be used as a charge generation layer, and this is favorable from the viewpoint of luminescent efficiency/driving voltage since the barrier between the units may be reduced.

The organic electroluminescent element of the present invention may be formed as a single element, or may be applied to a configuration where multiple elements are arranged in an array, or may also be applied to a configuration where the anode and the cathode are arranged in an X-Y matrix.

<Display and Lighting>

The display and the lighting of the present invention use the organic electroluminescent element of the present invention mentioned above. The type and the configuration of the display and the lighting of the present invention are not specifically defined. The display and the lighting can be constructed using the organic electroluminescent element of the present invention and according to any ordinary method.

For example, the display and the lighting of the present invention can be constructed according to the method described in "Organic EL Display" (by Ohm, issued on Aug. 20, 2004, written by Shizuo Tokito, Chihaya Adachi, Hideyuki Murata).

EXAMPLES

The present invention is described in more detail with reference to the following Examples. However, the present invention is not limited to the following Examples, not overstepping the scope and the spirit thereof. Various conditions and the data of evaluation results in the following Examples have the meanings of upper or lower preferred data in the embodiments of the present invention, and the preferred ranges may be the ranges to be defined by the combination of the upper or lower value and the value in the following Example or the combination of the values in the Examples.

Synthesis Example for Compound D-1 of the Invention

Synthesis Example 1: Synthesis Example for Compound 1

In a nitrogen flow, 11.72 g of 2-(3-bromophenyl)pyridine, 15.24 g of bispinacolatodiboron, 1.33 g of [PdCl$_2$(dppf)] CH$_2$Cl$_2$, 14.14 g of potassium acetate, and 100 ml of dewatered dimethyl sulfoxide were put in a 200-mL four-neck flask, and stirred in an oil bath at 90° C. for 3 hours. Subsequently, this was cooled to room temperature, and water and dichloromethane were added thereto for liquid separation washing, and thereafter the oily phase was dried with sodium sulfate. Next, the solvent was removed under reduced pressure. The obtained residue was purified through silica gel column chromatography (eluent: ethyl acetate/hexane=15/85) to give 14.70 g of a white solid (containing the compound 1 and a starting material bispinacolatodiboron as an impurity).

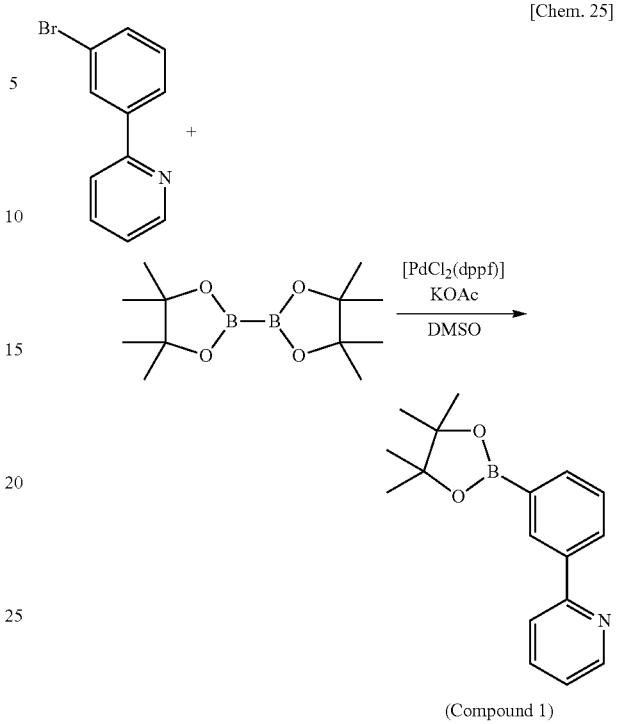

(Compound 1)

Synthesis Example 2: Synthesis Example for Compound 2

In a nitrogen flow, 14.70 g of the compound 1 produced in Synthesis Example 1, 14.81 g of 3-bromo-1-iodobenzene, 1.21 g of [Pd(PPh$_3$)$_4$], 70 ml of aqueous solution of 2 M tripotassium phosphate, 100 ml of toluene and 50 ml of ethanol were put in a 1 L eggplant flask, and stirred under reflux in an oil bath at 105° C. for 4.2 hours. Subsequently, this was cooled to room temperature, and water and toluene were added thereto for liquid separation washing, and thereafter the oily phase was dried with sodium sulfate. Next, the solvent was removed under reduced pressure. The obtained residue was purified through silica gel column chromatography (eluent: dichloromethane/hexane=1/1 to 2/1, followed by ethyl acetate/hexane=25/75) to give 13.50 g of a yellow oil (compound 2).

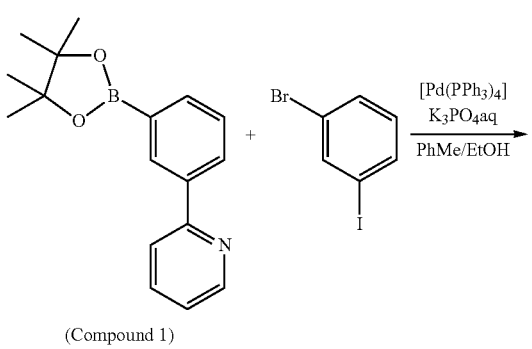

(Compound 1)

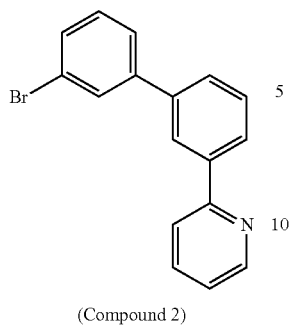

(Compound 2)

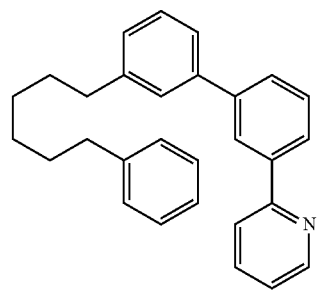

(Compound 3)

Synthesis Example 3: Synthesis Example for Compound 3

In a nitrogen flow, 1.02 g of magnesium (turnings) was put into a 100-mL four-neck flask, and with stirring, 5.07 g of 6-phenyl-1-bromohexane dissolved in 15 mL of dry diethyl ether was dropwise added thereto at room temperature, taking 10 minutes, and thereafter this was stirred at room temperature for 1 hour. The obtained Grignard reagent solution was dropwise added to a 100-ml three-neck flask containing 4.35 g of the compound 2, 0.39 g of [NiCl$_2$(dppp)] and 40 mL of dry diethyl ether, in a nitrogen flow at room temperature, taking 10 minutes. Subsequently, this was stirred for 1 hour at room temperature. Next, an aqueous solution of ammonium chloride was added thereto to stop the reaction, and then water and ethyl acetate were added thereto for liquid separation washing, and thereafter the oily phase was dried with sodium sulfate. Next, the solvent was removed under reduced pressure. The obtained residue was purified through silica gel column chromatography (eluent: ethyl acetate/hexane=1/9) to give 4.51 g of a yellow oil (compound 3).

[Chem. 27]

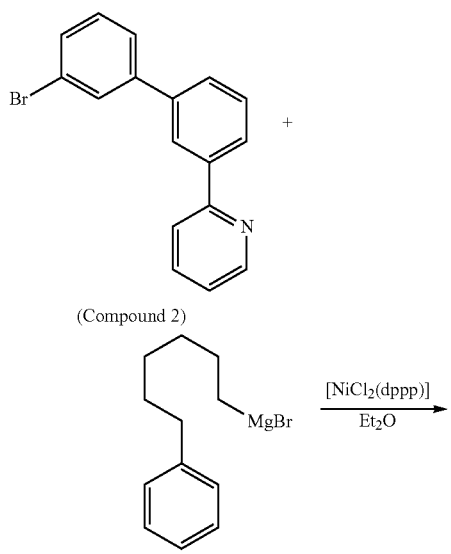

Synthesis Example 4: Synthesis Example for Compound D-1

In a nitrogen flow, 4.51 g of the compound 3, 1.45 g of [Ir(acac)$_3$] and 56 g of glycerin were put in a 200-mL four-neck flask, and bubbled with nitrogen in an oil bath at 100° C. for 1 hour. Subsequently, with the temperature of the oil bath kept elevated stepwise from 205° C. up to 230° C., this was stirred for 10 hours in total. Acetylacetone produced as a by-product was removed through the branch pipe during the reaction. Subsequently, this was cooled to room temperature, and water, methanol and dichloromethane were added thereto for liquid separation washing, and thereafter the oily phase was dried with sodium sulfate. Next, the solvent was removed under reduced pressure. The obtained residue was purified through silica gel column chromatography (eluent: dichloromethane/hexane=3/7) to give 1.0 g of the intended product (HPLC purity by 254-nm UV detector was nearly 100%). The $^1$H-NMR chart of the obtained compound is shown in FIG. 1.

The compound was mixed with phenylcyclohexane in an amount of 1.5% by weight relative to the latter and heated up to 120° C., whereupon the compound immediately dissolved to give a homogeneous solution. Subsequently, the solution was stored at room temperature for 2 months, and kept having a homogeneous state.

[Chem. 28]

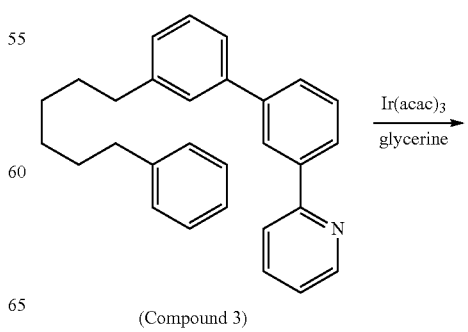

(Compound 3)

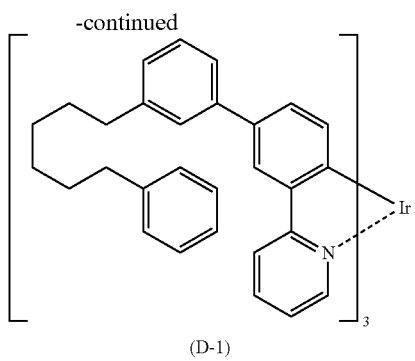

(D-1)

Synthesis Example for Compound D-2 of the Invention

Synthesis Example 5: Synthesis Example for Compound 4

In a nitrogen flow, magnesium (turnings) (6.6 g) and dry tetrahydrofuran (30 mL) were put into a reactor, and with stirring, a dry tetrahydrofuran (100 mL) solution of 3-phenyl-1-bromopropane (49.8 g) was gradually and dropwise added thereto to be in a flux, and thereafter stirred at room temperature for 30 minutes. The obtained Grignard reagent solution was gradually and dropwise added to a reactor containing a dry tetrahydrofuran (130 mL) solution of 3-bromobenzonitrile (45.2 g), in a nitrogen flow at room temperature. Subsequently, this was stirred for 1 hour at 60° C. Next, an aqueous solution of ammonium chloride was added thereto to stop the reaction, and then water and dichloromethane were added thereto for liquid separation washing, and thereafter the organic phase was dried with magnesium sulfate. Next, the solvent was removed under reduced pressure. The obtained residue was purified through silica gel column chromatography to give the compound 4 (20 g).

[Chem. 29]

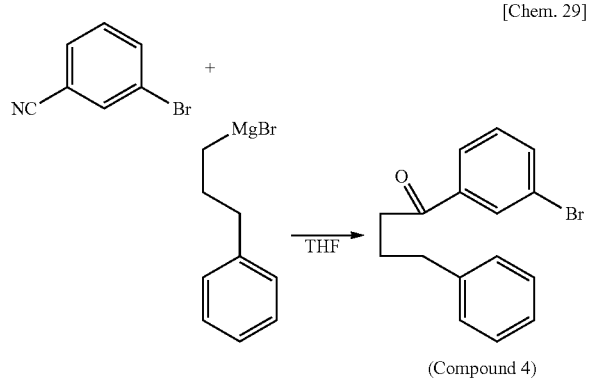

(Compound 4)

Synthesis Example 6: Synthesis Example for Compound 5

Sodium hydroxide (6.62 g) was added to a 2-(2-ethoxyethoxy)ethanol (220 mL) solution of the compound 4 (20.0 g), and then bubbled with nitrogen for 15 minutes with heating in an oil bath at 50° C. Hydrazine monohydrate (8 mL) was gradually and dropwise added thereto, and then gently refluxed in an oil bath at 110° C. for 2 hours. Once the heating was stopped, and a branched condenser tube was attached to the reactor. The temperature of the oil bath was stepwise elevated up to 180° C., and with removing the evaporated fraction through the branch pipe of the branched condenser tube, this was further stirred. After 1 hour, the evaporated fraction was detected little, and the heating was stopped. This was cooled to room temperature in an ice bath, and then the reaction solution was poured into 1 L of water. Using 1 N hydrochloric acid, this was made to have pH<1, then extracted with toluene, and the organic phase was washed with water and brine, then dried with MgSO$_4$, and concentrated under reduced pressure. The residue was purified through column chromatography to give the compound 5 (10.9 g).

[Chem. 30]

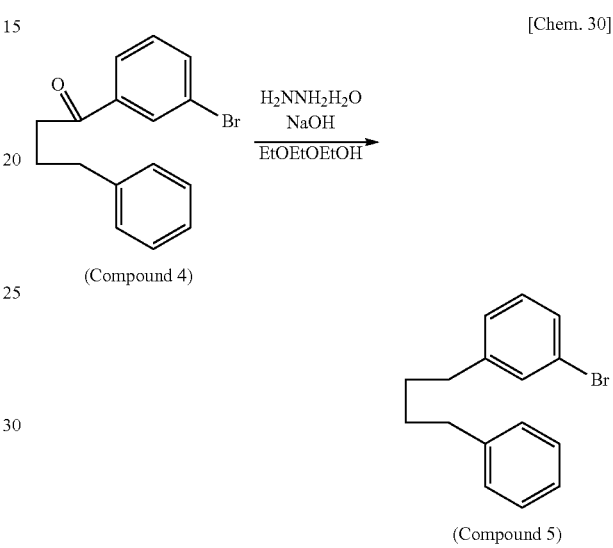

(Compound 5)

Synthesis Example 7: Synthesis Example for Compound 6

Bubbled with nitrogen, a toluene/ethanol mixed solution (3/1, 130 mL) and an aqueous solution of tripotassium phosphate (2.0 M, 50 mL) were added to the compound 1 (11.6 g) and the compound 5 (10.9 g). Pd(PPh$_3$)$_4$ (1.23 g) was added thereto, and with heating under reflux, this was stirred for 4 hours. After restored to room temperature, this was extracted with toluene, and the organic phase was washed with brine, then dried with anhydrous magnesium sulfate, and the solvent was evaporated away under reduced pressure. The residue was purified through column chromatography to give the compound 6 (12.8 g).

[Chem. 31]

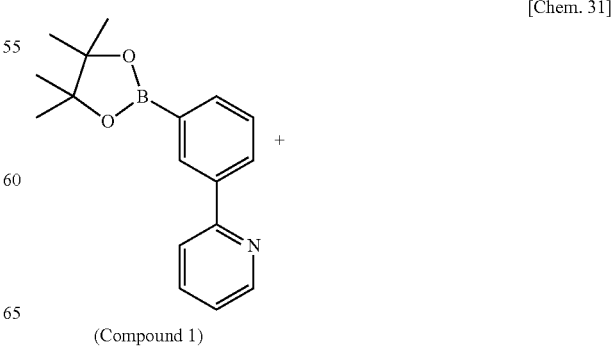

(Compound 1)

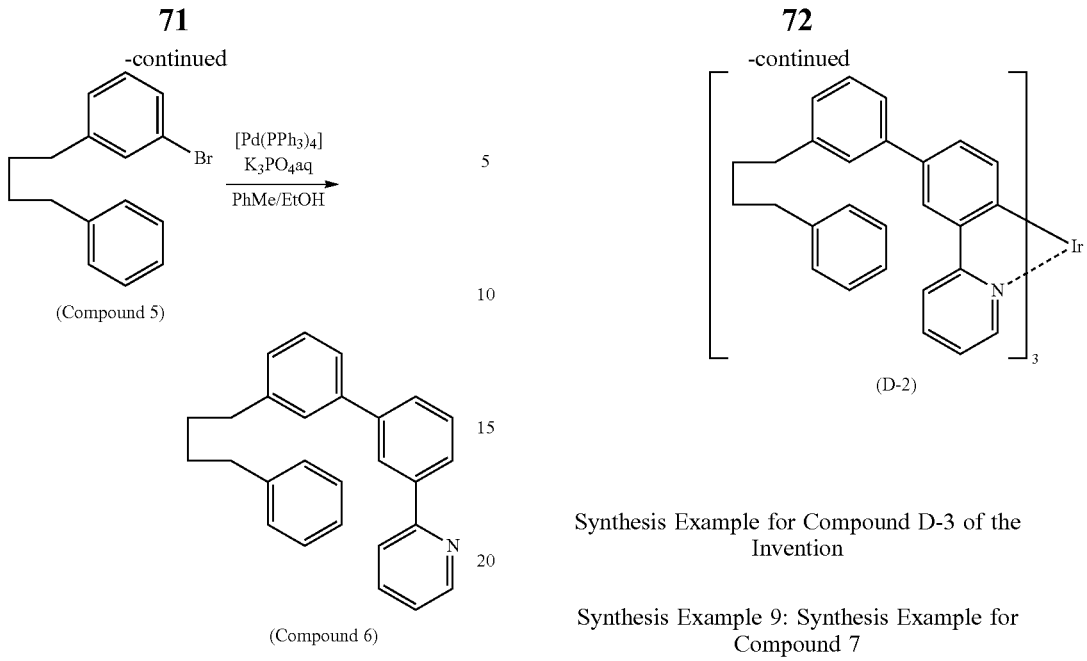

(Compound 5)

(Compound 6)

(D-2)

Synthesis Example 8: Synthesis Example for Compound D-2

In a nitrogen flow, a suspension of the compound 6 (12.8 g), Ir(acac)₃ (4.20 g) and glycerin (100 g) was bubbled with nitrogen for 15 minutes in an oil bath at 150° C. Subsequently, with the temperature of the oil bath kept elevated stepwise from 200° C. up to 230° C., this was stirred for 9 hours in total. Acetylacetone produced as a by-product was removed through the branch pipe during the reaction. Subsequently, this was cooled to room temperature, and water and dichloromethane were added thereto for liquid separation washing, and thereafter the organic phase was dried with magnesium sulfate. Next, the solvent was removed under reduced pressure. The obtained residue was purified through silica gel column chromatography to give the compound D-2 (0.7 g).

The compound was mixed with phenylcyclohexane in an amount of 1.5% by weight relative to the latter and heated up to 120° C., whereupon the compound immediately dissolved to give a homogeneous solution. Subsequently, the solution was stored at room temperature for 1 month, and kept having a homogeneous state.

[Chem. 32]

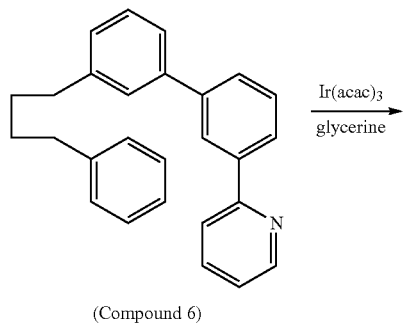

(Compound 6)

Synthesis Example for Compound D-3 of the Invention

Synthesis Example 9: Synthesis Example for Compound 7

In a nitrogen flow, magnesium (turnings) (7.10 g) and dry tetrahydrofuran (30 mL) were put into a reactor, and a dry tetrahydrofuran (100 mL) solution of 6-phenyl-1-bromohexane (64.0 g) was gradually and dropwise added thereto to be in a flux, and thereafter stirred at 60° C. for 1 hour. The obtained Grignard reagent solution was gradually and dropwise added to a reactor containing a dry tetrahydrofuran (130 mL) solution of 3-bromobenzonitrile (53.1 g), in a nitrogen flow at room temperature. Subsequently, this was stirred for 1 hour at 60° C. After this was restored to room temperature, an aqueous solution of ammonium chloride was added thereto to stop the reaction, and then water and methylene chloride were added thereto for liquid separation washing, and thereafter the organic phase was dried with magnesium sulfate. Next, the solvent was removed under reduced pressure. The obtained residue was purified through column chromatography to give the compound 7 (62.5 g).

[Chem. 33]

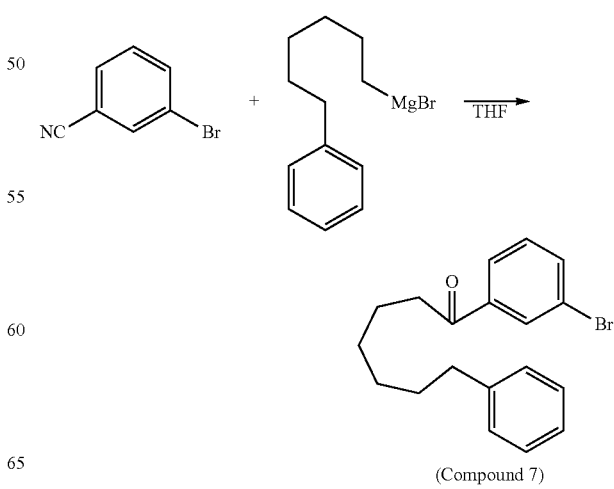

(Compound 7)

Synthesis Example 10: Synthesis Example for Compound 8

Sodium hydroxide (17.6 g) was added to a 2-(2-ethoxyethoxy)ethanol (420 mL) solution of the compound 7 (62.5 g), and then bubbled with nitrogen for 15 minutes with heating in an oil bath at 50° C. Hydrazine monohydrate (22.0 g) was gradually and dropwise added thereto, and then gently refluxed in an oil bath at 110° C. for 2 hours. Once the heating was stopped, and a branched condenser tube was attached to the reactor. The temperature of the oil bath was stepwise elevated up to 180 to 210° C., and with removing the evaporated fraction through the branch pipe of the branched condenser tube, this was further stirred. After 1 hour, the evaporated fraction was detected little, and the heating was stopped. This was cooled to room temperature in an ice bath, and then the reaction solution was poured into 1 L of water. Using 1 N hydrochloric acid, this was made to have pH<1, then extracted with methylene chloride, and the organic phase was washed with water and brine, then dried with MgSO$_4$, and concentrated under reduced pressure. The residue was purified through column chromatography to give the compound 8 (41.2 g).

[Chem. 34]

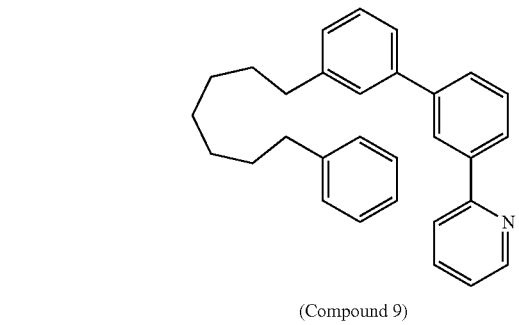

(Compound 7)

(Compound 8)

Synthesis Example 11: Synthesis Example for Compound 9

A toluene/ethanol mixed solution (3/1, 130 mL) and an aqueous solution of tripotassium phosphate (2.0 M, 52 mL) were added to the compound 1 (12.1 g) and the compound 8 (13.6 g), and then bubbled with nitrogen for 30 minutes. Pd(PPh$_3$)$_4$ (0.95 g) was added thereto, and with heating under reflux, this was stirred for 3 hours. After restored to room temperature, this was extracted with toluene, and the organic phase was washed with brine, then dried with anhydrous magnesium sulfate, and the solvent was evaporated away under reduced pressure. The residue was purified through column chromatography to give the compound 9 (16.4 g).

[Chem. 35]

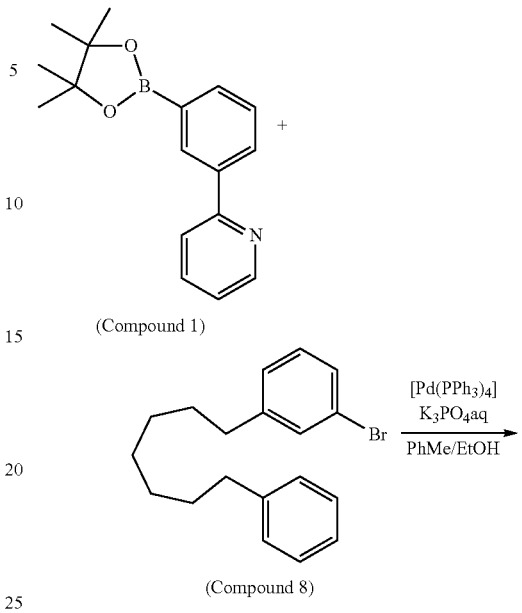

(Compound 1)

(Compound 8)

(Compound 9)

Synthesis Example 12: Synthesis Example for Compound D-3

In a nitrogen flow, a suspension of the compound 9 (8.65 g), Ir(acac)$_3$ (2.61 g) and glycerin (130 g) was bubbled with nitrogen for 30 minutes in an oil bath at 120° C. Subsequently, with the temperature of the oil bath kept elevated stepwise from 220° C. up to 240° C., this was stirred for 7 hours in total. Acetylacetone produced as a by-product was removed through the branch pipe during the reaction. Subsequently, this was cooled to room temperature, and water was added thereto and the aqueous phase was removed. Next, dichloromethane was added thereto for liquid separation washing, and the organic phase was dried with magnesium sulfate. The solvent was removed under reduced pressure. The obtained residue was purified through column chromatography to give the compound D-3 (0.19 g).

The compound was mixed with phenylcyclohexane in an amount of 1.5% by weight relative to the latter and heated up to 120° C., whereupon the compound immediately dissolved to give a homogenous solution. Subsequently, the solution was stored at room temperature for 1 month, and kept having a homogeneous state.

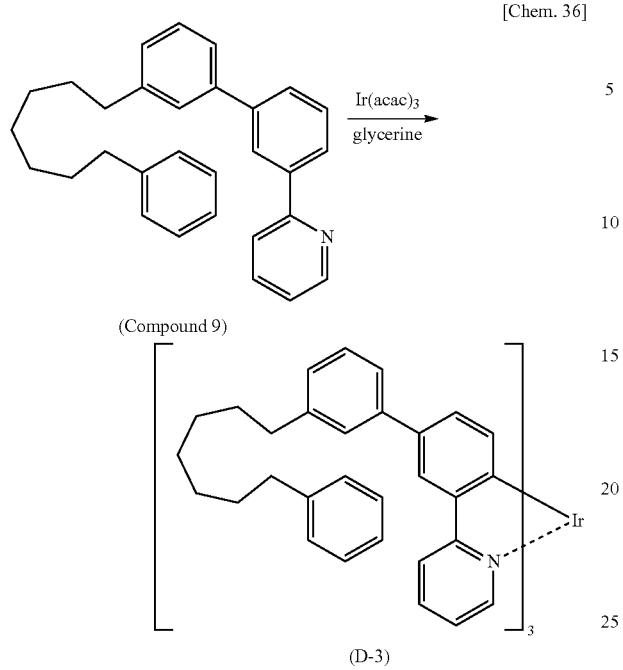

(Compound 9)

(D-3)

Synthesis Example for Comparative Compound D-4

Synthesis Example 13: Synthesis Example for Compound 10

In a nitrogen flow, magnesium (turnings) (1.34 g) was put into a four-neck flask, and with stirring, dibromohexane (7.29 g) dissolved in dry diethyl ether (30 mL) was dropwise added thereto at room temperature, and thereafter stirred at room temperature for 1 hour. The obtained Grignard reagent solution was dropwise added to a four-neck flask containing the compound 2 (6.15 g), [NiCl$_2$(dppp)] (0.59 g) and dry diethyl ether (40 mL), in a nitrogen flow at room temperature. Subsequently, this was stirred for 1 hour at room temperature. Next, an aqueous solution of ammonium chloride was added thereto to stop the reaction, and then water and ethyl acetate were added thereto for liquid separation washing, and thereafter the oily phase was dried with magnesium sulfate. Next, the solvent was removed under reduced pressure. The obtained residue was purified through column chromatography to give the compound 10 (5.97 g).

[Chem. 37]

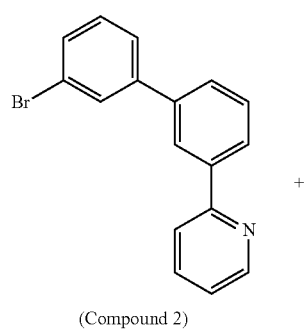

(Compound 2)

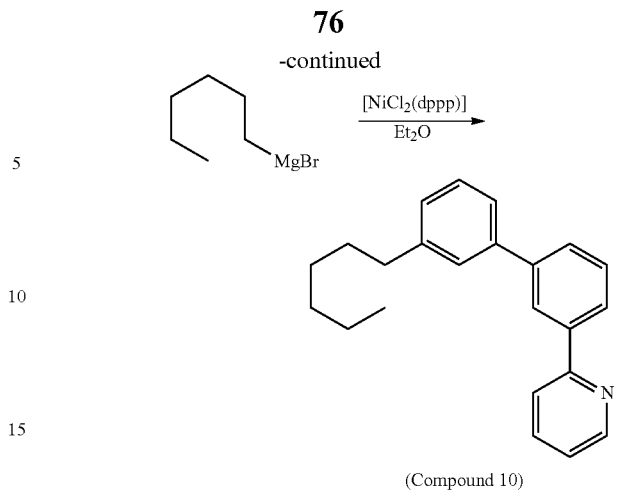

(Compound 10)

Synthesis Example 14: Synthesis Example for Comparative Compound D-4

In a nitrogen flow, a suspension of the compound 10 (5.65 g), Ir(acac)$_3$ (2.17 g) and glycerin (108 g) was bubbled with nitrogen for 40 minutes in an oil bath at 110° C. Subsequently, with the temperature of the oil bath kept elevated stepwise from 205° C. up to 230° C., this was stirred for 9 hours in total. Acetylacetone produced as a by-product was removed through the branch pipe during the reaction. Subsequently, this was cooled to room temperature, and water, methanol and dichloromethane were added thereto for liquid separation washing, and thereafter the organic phase was dried with magnesium sulfate. The solvent was removed under reduced pressure. The obtained residue was purified through column chromatography to give the compound D-4 (1.08 g).

[Chem. 38]

Synthesis Example for Comparative Compound D-6

Synthesis Example 15: Synthesis Example for Compound 11

In a nitrogen flow, an aqueous solution (70 mL) of sodium carbonate (27.0 g) was added to a toluene/ethanol mixed solution (2/1, 160 mL) of 2-(3-bromophenyl)pyridine (20.0 g) and 4-hexylphenylboronic acid (21.0 g), and bubbled with nitrogen for 30 minutes. Pd(PPh$_3$)$_4$ (1.00 g) was added thereto, and further bubbled with nitrogen for 10 minutes, and thereafter stirred under reflux for 3 hours in an oil bath at 105° C. Subsequently, this was cooled to room temperature, then water and toluene were added thereto for liquid separation washing, and the organic phase was dried with magnesium sulfate. Next, the solvent was removed under reduced pressure. The obtained residue was purified through column chromatography to give the compound 11 (27.3 g).

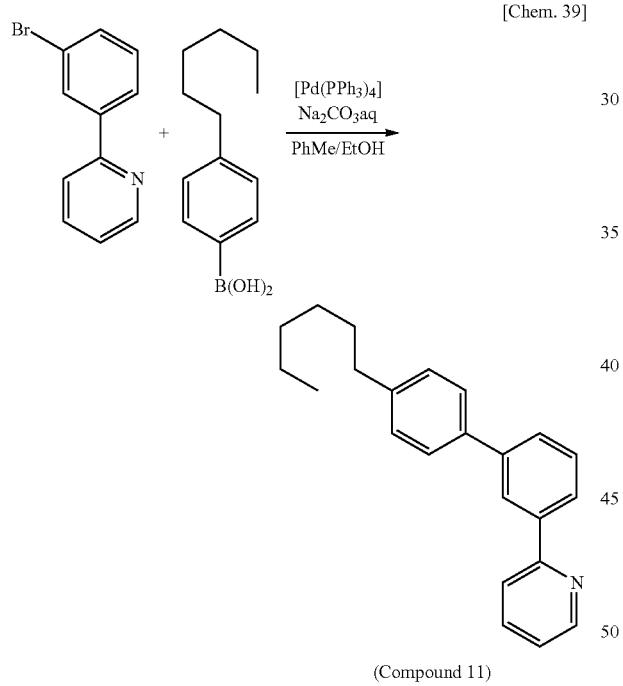

[Chem. 39]

(Compound 11)

Synthesis Example 16: Synthesis Example for Comparative Compound D-6

In a nitrogen flow, a suspension of the compound 11 (18.3 g), Ir(acac)$_3$ (7.14 g) and glycerin (243 g) was bubbled with nitrogen for 30 minutes in an oil bath at 100° C. Subsequently, with the temperature of the oil bath kept elevated stepwise from 230° C. up to 250° C., this was stirred for 6 hours in total. Acetylacetone produced as a by-product was removed through the branch pipe during the reaction. Subsequently, this was cooled to room temperature, and water and methanol were added thereto and the aqueous phase was removed. Next, dichloromethane was added thereto for liquid separation washing, and the organic phase was dried with magnesium sulfate. The solvent was removed under reduced pressure. The obtained residue was purified through column chromatography and recrystallized from toluene to give the compound D-6 (0.9 g).

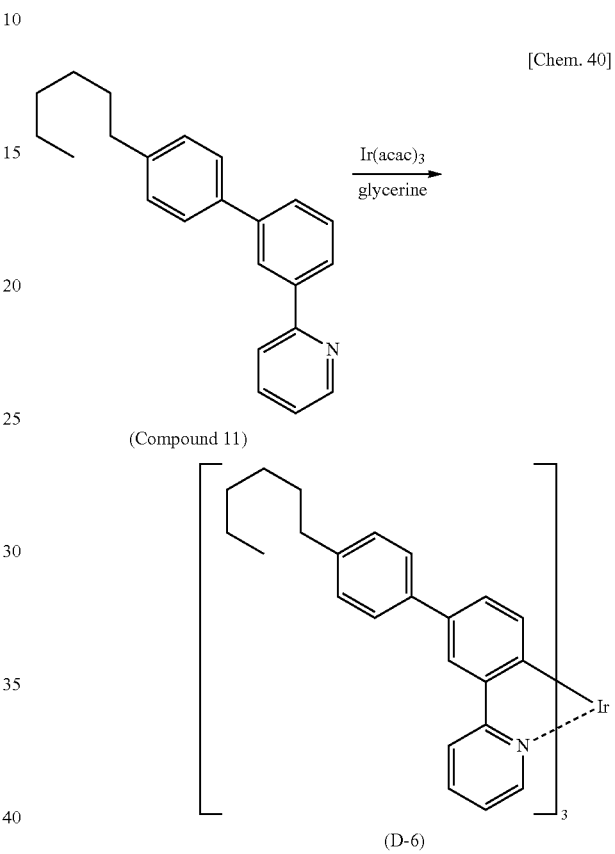

[Chem. 40]

(Compound 11)

(D-6)

Synthesis Example for Comparative Compound D-7

Synthesis Example 17: Synthesis Example for Compound 13

A toluene/ethanol mixed solution (2/1, 150 mL) and an aqueous solution of tripotassium phosphate (2.0 M, 25 mL) were added to 2-(3-bromophenyl)pyridine (4.19 g) and the compound 12 (6.34 g), and then bubbled with nitrogen for 30 minutes. Pd(PPh$_3$)$_4$ (0.68 g) was added thereto, and with heating under reflux, this was stirred for 3 hours. After restored to room temperature, this was extracted with toluene, and the organic phase was washed with brine, then dried with anhydrous magnesium sulfate, and the solvent was evaporated away under reduced pressure. The residue was purified through column chromatography to give the compound 13 (5.36 g). The compound 12 was obtained according to the method described in JP-A 2011-195462.

[Chem. 41]

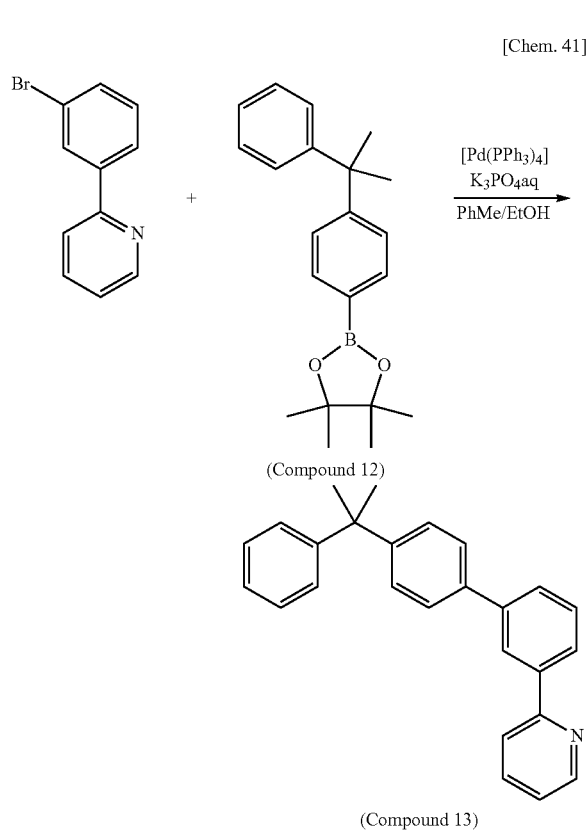

Synthesis Example 18: Synthesis Example for Comparative Compound D-7

In a nitrogen flow, a suspension of the compound 13 (5.20 g), Ir(acac)$_3$ (1.83 g) and glycerin (95 g) was bubbled with nitrogen for 30 minutes in an oil bath at 80° C. Subsequently, with the temperature of the oil bath kept elevated stepwise from 220° C. up to 230° C., this was stirred for 8.5 hours in total. Acetylacetone produced as a by-product was removed through the branch pipe during the reaction. Subsequently, this was cooled to room temperature, and ethanol was added thereto and glycerin was removed. Next, dichloromethane was added thereto for liquid separation washing, and the organic phase was dried with magnesium sulfate. The solvent was evaporated away under reduced pressure. The obtained residue was purified through column chromatography to give the compound D-7 (0.38 g).

[Chem. 42]

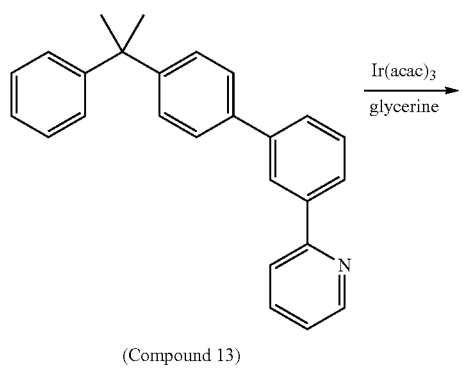

Synthesis Example for Comparative Compound D-8

Synthesis Example 19: Synthesis Example for Compound 14

5-Chloro-2-nitrobenzaldehyde (50 g), phenylboronic acid (39.4 g), tripotassium phosphate (85.8 g), S—PHOS (bought from Wako Pure Chemicals, 12.2 g) and toluene (500 mL) were put into a reactor in that order, and bubbled with nitrogen for 30 minutes. Pd(OAc)$_2$ (3.03 g) was added thereto, and stirred for 9 hours with heating under reflux. This was restored to room temperature, then methylene chloride was added thereto, and filtered through Celite. The filtrate was extracted and washed, and the organic phase was dried with anhydrous magnesium sulfate. The solvent was evaporated away under reduced pressure. The residue was purified through column chromatography to give the compound 14 (37.7 g).

[Chem. 43]

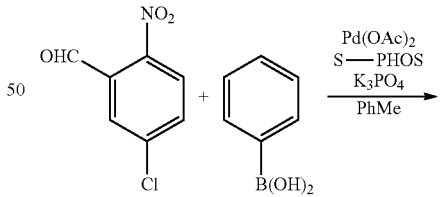

Synthesis Example 20: Synthesis Example for Compound 15

Ethanol (200 mL) was added to the compound 14 (15 g), and heated at 50° C. to be a solution. Iron powder (9.2 g) and 0.1 N hydrochloric acid (33 mL) were added thereto in that order, and stirred for 3 hours with heating under reflux. Since the starting material remained, 1 N hydrochloric acid (1 mL) was added thereto and further heated under reflux for 1 hour. Since the starting material still remained, 1 N hydrochloric acid (2 mL) was added, and further heated under reflux for 1 hour. After this was restored to room temperature, 3'-bromoacetophenone (10.5 g) and powdered potassium hydroxide (4.4 g) were added thereto in that order. This was stirred at room temperature for 30 minutes, and then 3'-bromoacetophenone (1.31 g) was added thereto and further stirred at room temperature for 2 hours. The reaction liquid was filtered, the filter residue was dissolved in methylene chloride, again filtered, and the filtrate was concentrated under reduced pressure. The residue was processed through column chromatography, and the obtained solid was washed with ethanol to give the compound 15 (22.7 g).

liquid separation washing, and the organic phase was dried with magnesium sulfate. Next, the solvent was removed under reduced pressure. The obtained residue was purified through column chromatography to give the compound 16 (10.4 g).

[Chem. 45]

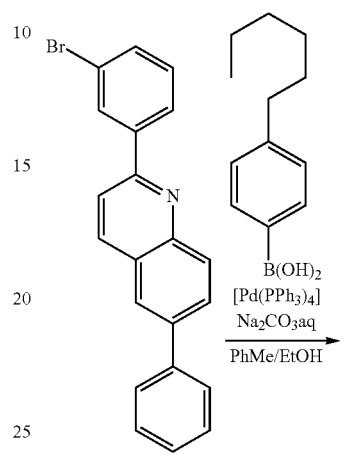

(Compound 15)

[Chem. 44]

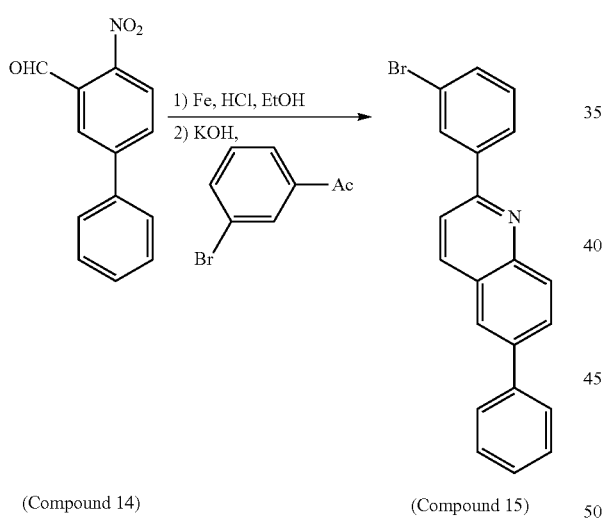

(Compound 14)    (Compound 15)

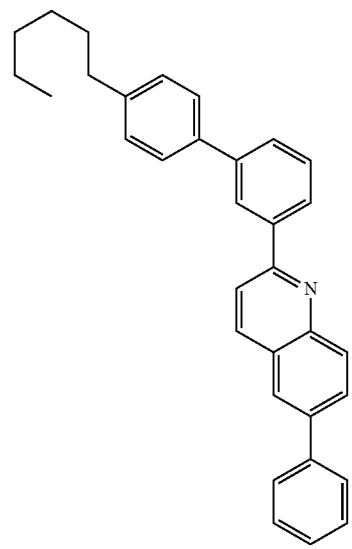

(Compound 16)

Synthesis Example 21: Synthesis Example for Compound 16

In a nitrogen flow, a toluene/ethanol mixed solution (2/1, 150 mL) of the compound 15 (9.0 g) and 4-hexylphenylboronic acid (6.2 g) was bubbled with nitrogen for 30 minutes. Bubbled with nitrogen for 30 minutes, an aqueous solution (50 mL) of sodium carbonate (10.6 g) and Pd(PPh$_3$)$_4$ (1.4 g) were added thereto in that order, and stirred for 10 hours under reflux. Next, this was cooled to room temperature, then water and methylene chloride were added thereto for

Synthesis Example 22: Synthesis Example for Compound 17

In a nitrogen flow, 2-ethoxyethanol (66 mL) and water (22 mL) were added to the intermediate 16 (10.4 g) and IrCl$_3$·n-hydrate (4.4 g), and stirred for 20 hours with heating under reflux. Subsequently, this was extracted with dichloromethane, and the organic layer was washed with water, concentrated under reduced pressure and poured into methanol for reprecipitation to give the compound 17 (12.5 g).

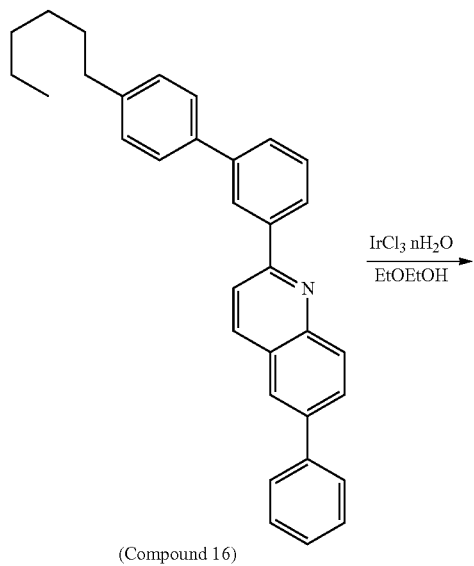

(Compound 16)

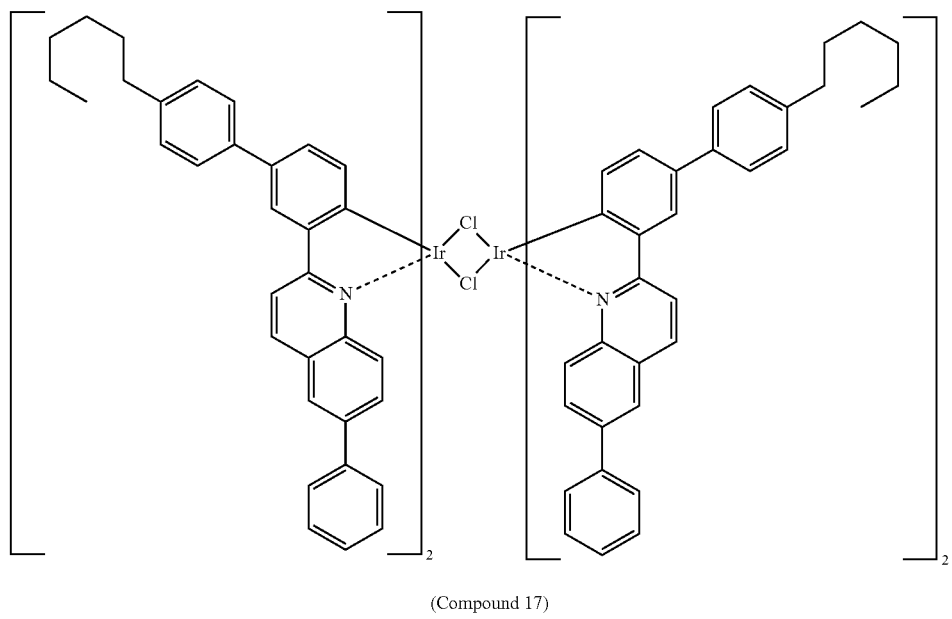

(Compound 17)

Synthesis Example 23: Synthesis Example for Compound 18

In a nitrogen flow, the compound 17 (12.5 g), sodium acetylacetonate (3.4 g) and 2-ethoxyethanol (150 mL) were put into a reactor in that order, and stirred at 135° C. for 10 hours. Subsequently, this was extracted with dichloromethane, and the organic phase was washed with brine, dried with sodium sulfate, and concentrated under reduced pressure. The residue was processed through column chromatography and washed with methanol in suspension to give the compound 18 (8.89 g) in a purity of 20%.

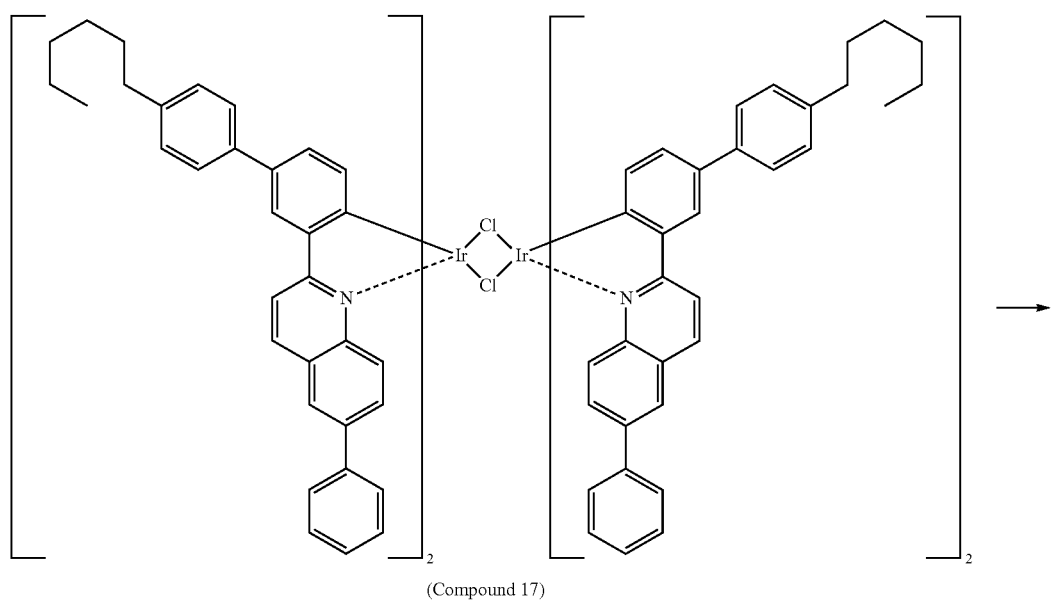

(Compound 17)

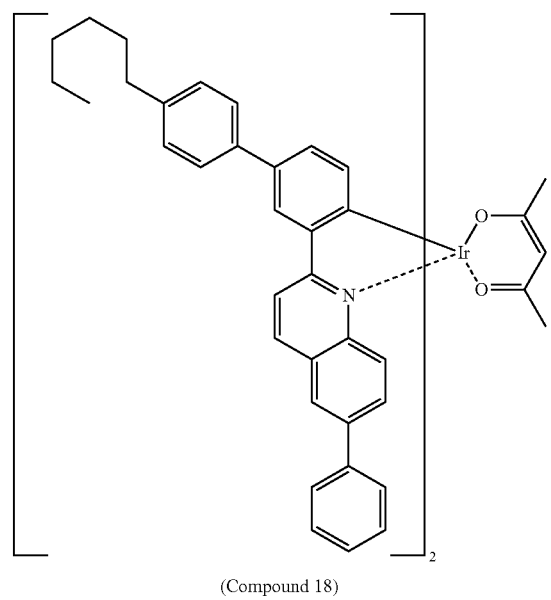

(Compound 18)

Synthesis Example 24: Synthesis Example for Comparative Compound D-8

In a nitrogen flow, glycerol (45 mL) was added to the compound 16 (2.9 g), and bubbled with nitrogen in an oil bath at 90° C. The compound 18 (20% purity, 8.85 g) was added thereto, and stirred at 240° C. to 250° C. for 13.5 hours. Subsequently, methanol was added thereto, and the precipitate was taken out through suction filtration. This was processed through column chromatography and reprecipitated from methanol to give the compound D-8 (0.2 g).

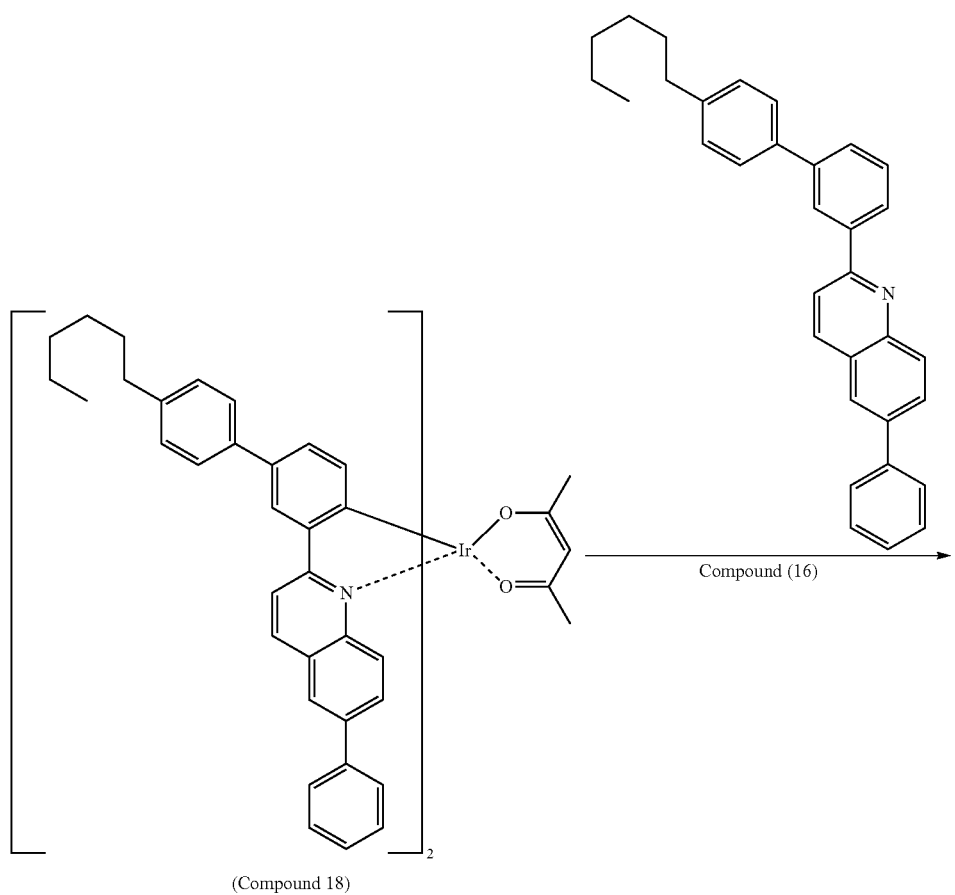
(Compound 18)
Compound (16)
[Chem. 48]
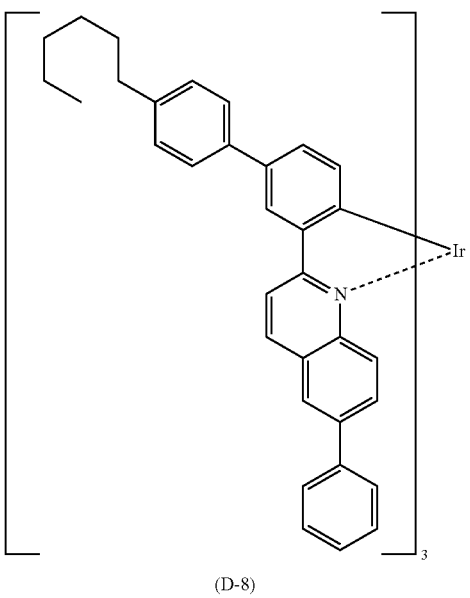
(D-8)

Synthesis Example for Comparative Compound D-9

Synthesis Example 25: Synthesis Example for Compound 19

2-Aminobenzophenone (15.0 g), 3'-bromoacetophenone (18.2 g), acetic acid (75 mL) and concentrated sulfuric acid (1.3 mL) were put into a reactor in that order, and heated under reflux for 9.5 hours. The reaction liquid was poured into water, extracted and washed with ethyl acetate, and the organic phase was dried with $MgSO_4$, and concentrated under reduced pressure. This was purified through column chromatography to give the compound 19 (24.2 g).

[Chem. 49]

further heated for 7.5 hours under reflux. This was restored to room temperature, then water and toluene were added thereto for liquid separation washing, and the organic phase was dried with magnesium sulfate. Next, the solvent was removed under reduced pressure. The obtained residue was purified through column chromatography to give the compound 20 (24.1 g).

[Chem. 50]

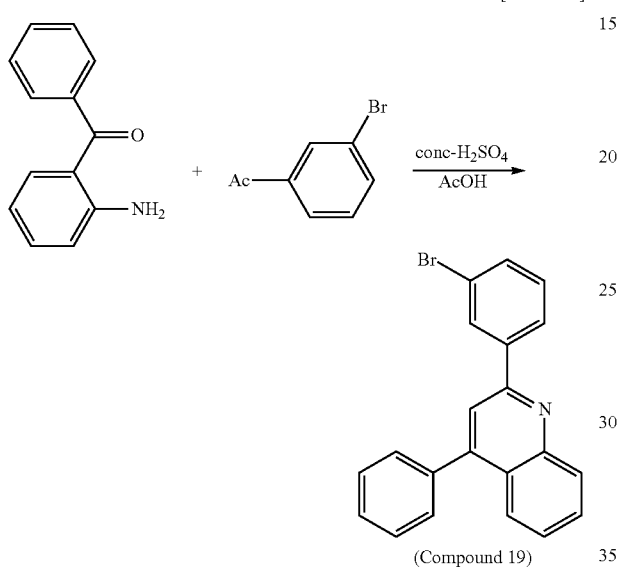

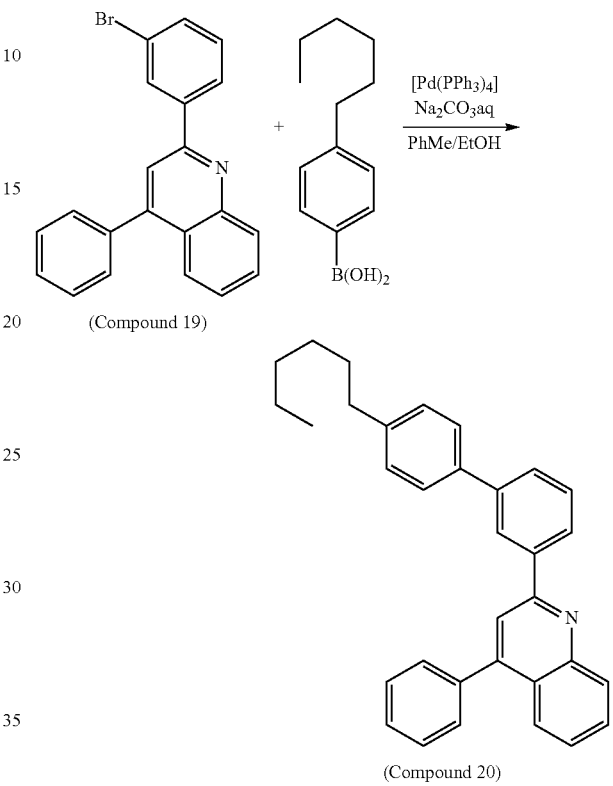

Synthesis Example 26: Synthesis Example for Compound 20

In a nitrogen flow, a toluene/ethanol mixed solution (1/1, 400 mL) of the compound 19 (24.2 g) and 4-hexylphenylboronic acid (18.0 g) was bubbled with nitrogen for 30 minutes. Bubbled with nitrogen for 30 minutes, an aqueous solution (100 mL) of sodium carbonate (21.4 g) and $Pd(PPh_3)_4$ (2.33 g) were added thereto in that order, and stirred for 8 hours under reflux. Next, this was cooled to room temperature, 4-hexylphenylboronic acid (5.5 g) and $Pd(PPh_3)_4$ (0.8 g) were added thereto in that order, and Synthesis Example 27: Synthesis Example for Compound 21

In a nitrogen flow, 2-ethoxyethanol (71 mL) an water (24 mL) were added to the compound 20 (12.0 g) and $IrCl_3$.n-hydrate (4.7 g), and stirred for 11 hours with heating under reflux. Subsequently, this was extracted with dichloromethane, and the organic layer was washed with water, concentrated under reduced pressure and poured into methanol for reprecipitation to give the compound 21 (11.9 g).

[Chem. 51]

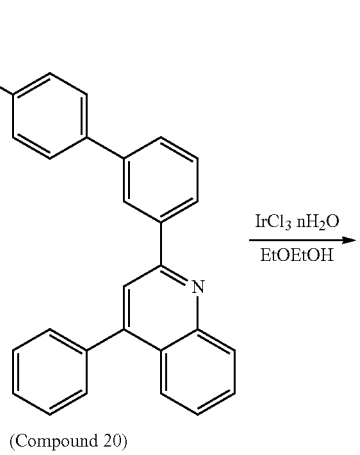

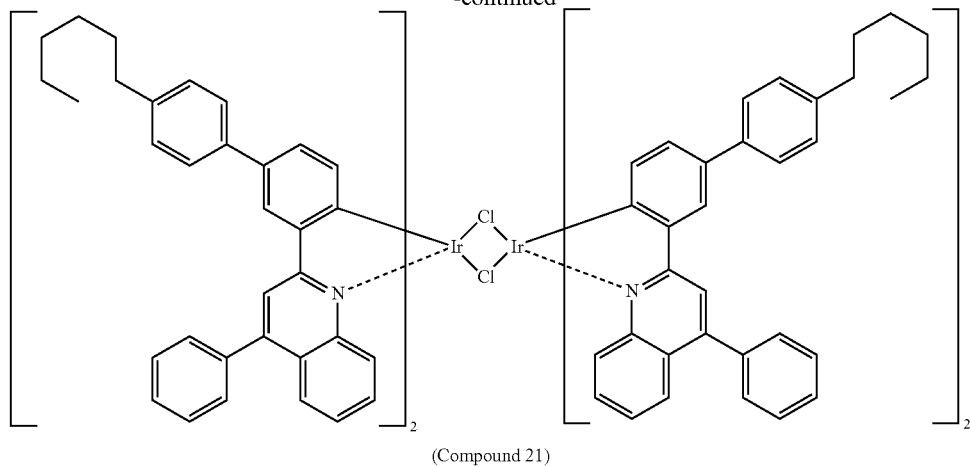

(Compound 21)

Synthesis Example 28: Synthesis Example for Compound 22

In a nitrogen flow, the compound 21 (11.9 g), sodium acetylacetonate (3.3 g) and 2-ethoxyethanol (140 mL) were put into a reactor in that order, and stirred at 135° C. for 8 hours. Subsequently, this was extracted with dichloromethane, and the organic phase was washed with saturated saline, dried with sodium sulfate, and concentrated under reduced pressure. Repeatedly the residue was processed through column chromatography and washed with methanol in suspension to give the compound 22 (6.9 g).

[Chem. 52]

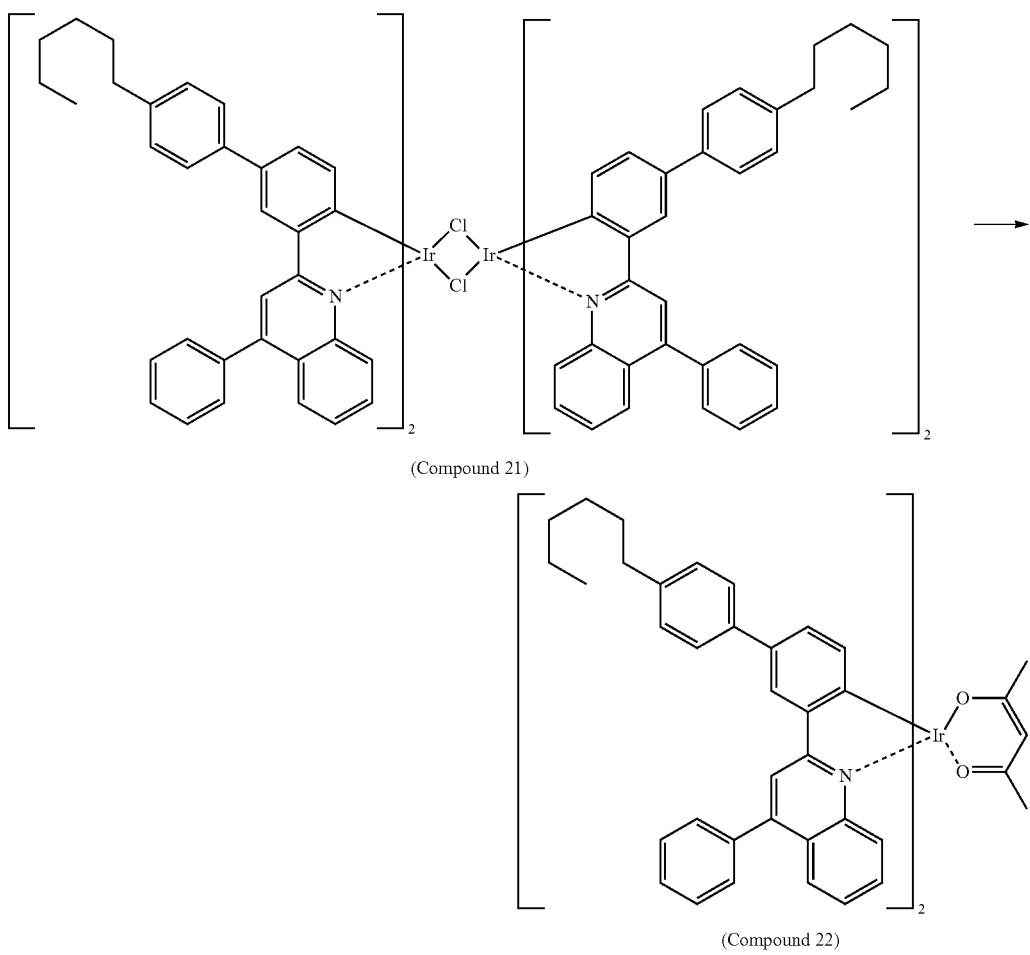

(Compound 21)

(Compound 22)

Synthesis Example 29: Synthesis Example for Comparative Compound D-9

In a nitrogen flow, glycerol (172 mL) was added to the compound 20 (12.1 g), and bubbled with nitrogen for 30 minutes in an oil bath at 80° C. The compound 22 (6.9 g) was added thereto, and stirred at 200° C. for 15 hours. Subsequently, methanol was added thereto, and the oily substance was separated from the solution. The oily substance was dissolved in methylene chloride, and filtered through Celite. The filtrate was concentrated, and the residue was processed through column chromatography and reprecipitated repeatedly multiple times to give the compound D-9 (0.6 g).

Synthesis Example for Compound D-10 of the Invention

Synthesis Example 30: Synthesis Example for Compound 23

Ethanol (420 mL) was added to the compound 14 (42.5 g), and heated at 50° C. to be a solution. Iron powder (41.8 g) and 0.1 N hydrochloric acid (94 mL) were added thereto in that order, and stirred for 80 minutes with heating under reflux. After this was restored to room temperature, 3'-(3-bromophenyl)acetophenone (51.5 g) and powdered potassium hydroxide (12.6 g) were added thereto in that order, and stirred for 4 hours with heating under reflux. The reaction liquid was filtered through Celite, the residue was extracted a few times with methylene chloride, and the

[Chem. 53]

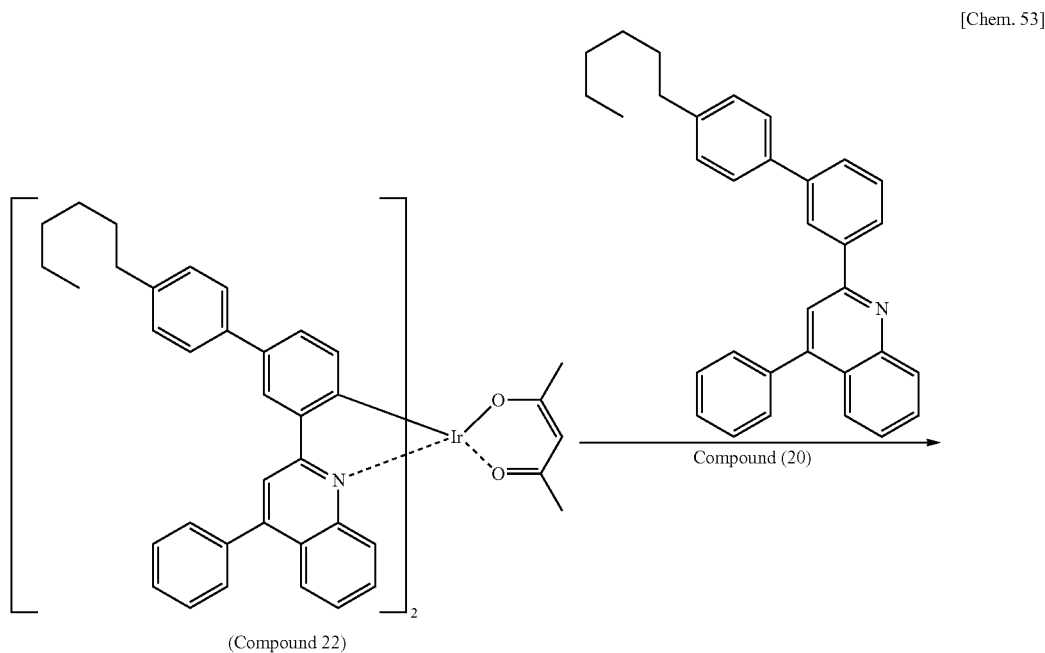

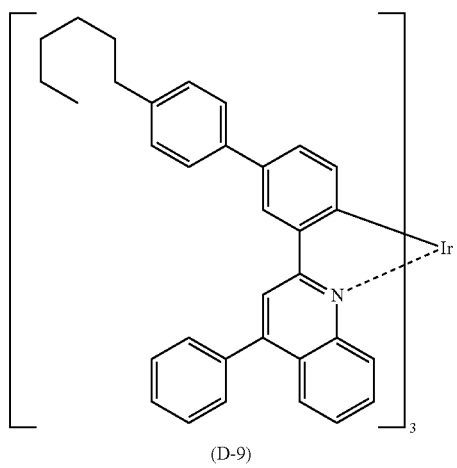

insoluble was again separated through Celite filtration. The obtained filtrates were combined and concentrated under reduced pressure, extracted and washed with methylene chloride, and the organic phase was washed with brine, dried with MgSO₄, and concentrated under reduced pressure. The residue was processed through column chromatography, and the obtained solid was reprecipitated with methylene chloride/hexane to give the compound 23 (101 g).

[Chem. 54]

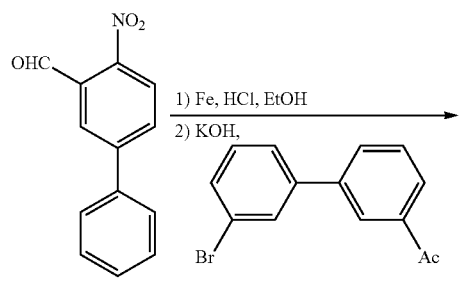

(Compound 14)

[Chem. 55]

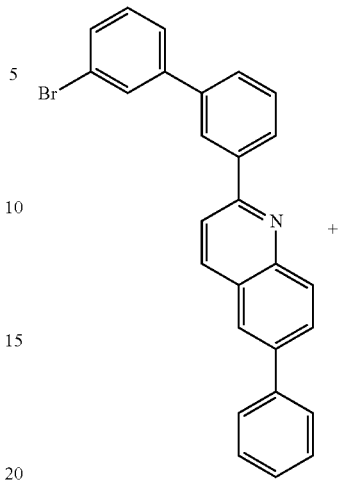

(Compound 23)

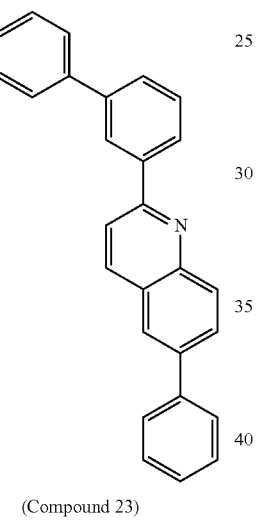

(Compound 23)

Synthesis Example 31: Synthesis Example for Compound 24

In a nitrogen flow, magnesium (turnings) (14 g) was put into a rector, and with stirring, 6-phenyl-1-bromohexane (83.3 g) dissolved in dry diethyl ether (210 mL) was gradually and dropwise added thereto. Subsequently, this was stirred at room temperature for 1 hour. The obtained Grignard reagent solution was dropwise added to a reactor containing the compound 23 (101 g), [NiCl₂(dppp)] (6.3 g) and dry diethyl ether (750 mL), in a nitrogen flow at room temperature, and then stirred at room temperature for 2 hours. Subsequently, an aqueous solution of ammonium chloride was added thereto to stop the reaction, and then water and methylene chloride were added thereto for liquid separation washing, and thereafter the organic phase was dried with magnesium sulfate. Next, the solvent was removed under reduced pressure. The obtained residue was purified through column chromatography to give the compound 24 (54.4 g).

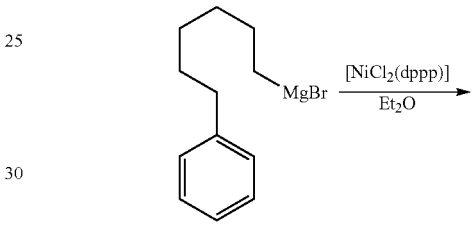

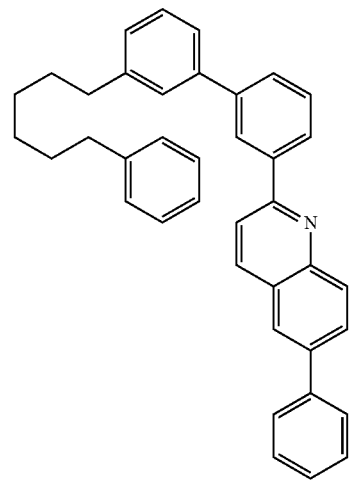

(Compound 24)

Synthesis Example 32: Synthesis Example for Compound 25

Bubbled with nitrogen, 2-ethoxyethanol (200 mL) and water (20 mL) were added to the compound 24 (20 g) and IrCl₃·n-hydrate (6.33 g) in a nitrogen flow. With the inner temperature kept stepwise elevated up to 100 to 136° C., this was stirred for 13.5 hours in total. Subsequently, this was extracted with dichloromethane, and the organic phase was washed with water and concentrated under reduced pressure to give the compound 25 as a crude product.

[Chem. 56]

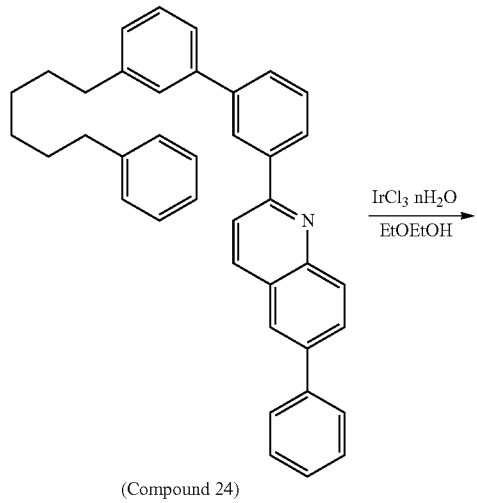

(Compound 24)

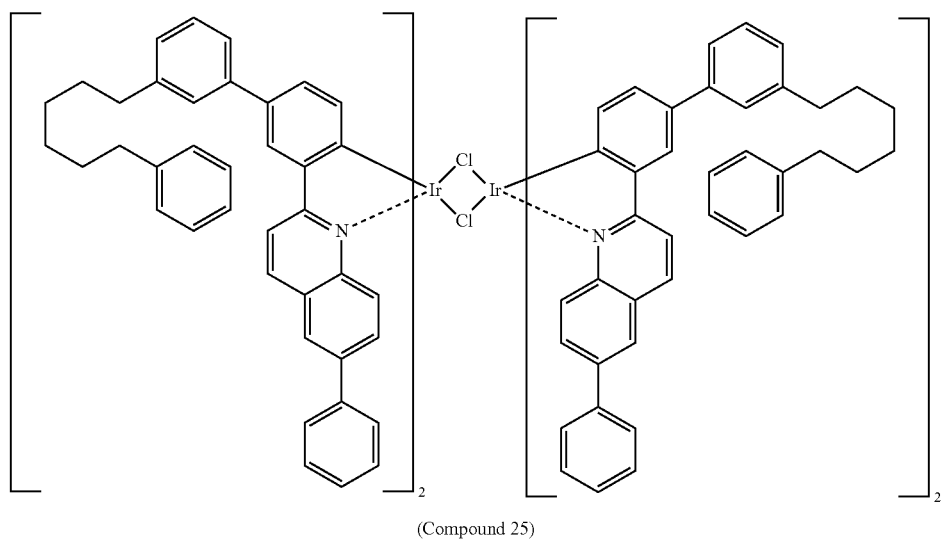

(Compound 25)

Synthesis Example 33: Synthesis Example for Compound 26

In a nitrogen flow, the crude product of compound 25, sodium acetylacetonate (4.5 g) and 2-ethoxyethanol (200 mL) were put into a reactor in that order, and stirred at 135° C. for 40 minutes. Subsequently, this was extracted with dichloromethane, and the organic phase was washed with brine, dried with magnesium sulfate, and concentrated under reduced pressure. Repeatedly the residue was processed through column chromatography and washed with methanol in suspension to give the compound 26 (22.8 g).

[Chem. 57]

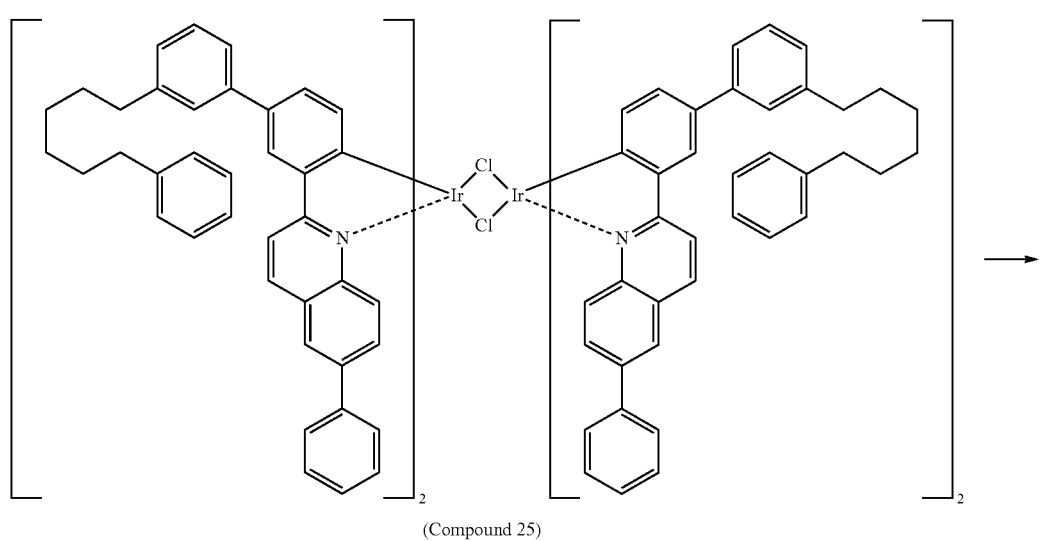

(Compound 25)

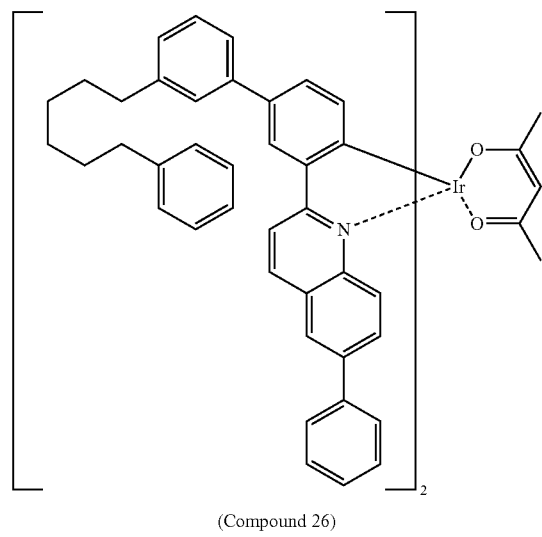

(Compound 26)

Synthesis Example 34: Synthesis Example for Compound D-10

In a nitrogen flow, the compound 26 (22.8 g) and the compound 24 (63.5 g) were stirred in an oil bath at 260° C. for 24 hours. The residue was purified through column chromatography and reprecipitation to give the compound D-10 (3.48 g).

The compound was mixed in phenylcyclohexane in an amount of 1.5% by weight relative to the latter, and heated up to 120° C., whereupon the compound immediately dissolved to give a homogeneous solution. Subsequently, the solution was stored at room temperature for 2 months, and kept having a homogeneous state.

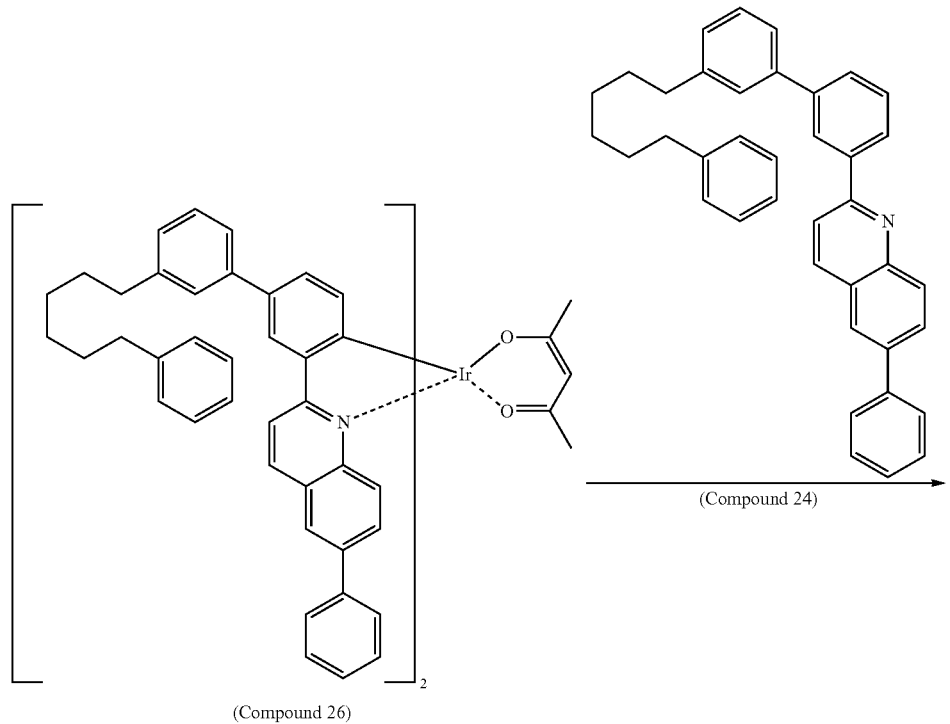

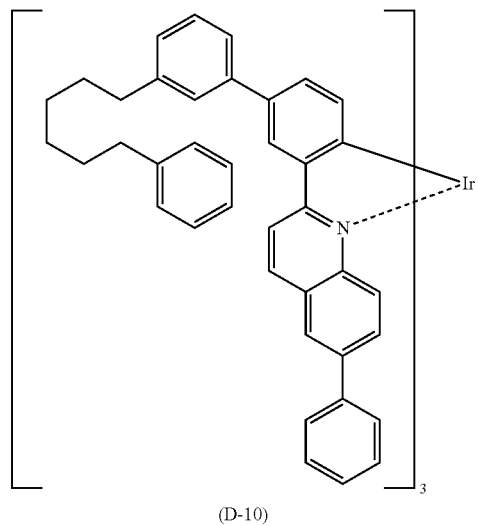

Synthesis Example for Compound D-11 of the Invention

Synthesis Example 35: Synthesis Example for Compound 27

In a nitrogen flow, the compound 19 (120 g), bispinacolatodiboron (102 g), potassium acetate (167 g), and dewatered dimethyl sulfoxide (600 mL) were put into a reactor in that order, and bubbled with nitrogen at 50° C. for 30 minutes. [PdCl$_2$(dppf)]CH$_2$Cl$_2$ (8.16 g) was added thereto, and then stirred at an inner temperature of from 80 to 85° C. for 4.5 hours. Subsequently, this was cooled to room temperature, poured into water (2.1 L), the precipitate was taken out through filtration, the resulting solid was extracted and washed with dichloromethane, and the organic phase was dried with magnesium sulfate. Subsequently, the solvent was removed under reduced pressure, and the obtained residue was purified through column chromatography to give the compound 27 (129 g).

[Chem. 59]

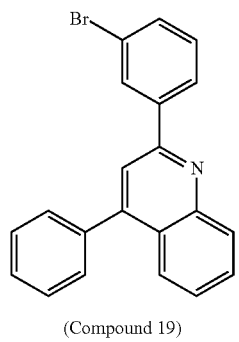 + 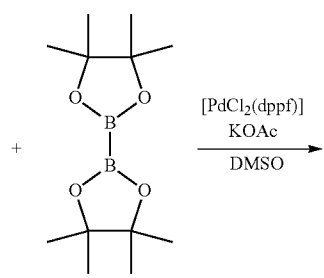 →[PdCl₂(dppf)] KOAc DMSO]

(Compound 19)

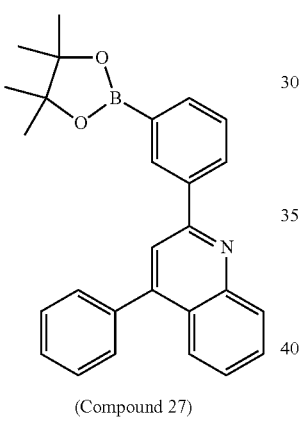

(Compound 27)

Synthesis Example 36: Synthesis Example for Compound 28

The compound 27 (122 g), 3-bromoiodobenzene (127 g), and toluene/ethanol mixed solution (2/1, 1140 mL) were put in a reactor in that order, and bubbled with nitrogen for 30 minutes. An aqueous solution of tripotassium phosphate (2.0 M, 346 mL) was added thereto, and further bubbled with nitrogen for 15 minutes. [Pd(PPh₃)₄] (10.4 g) was added thereto, and stirred for 4.5 hours with heating under reflux. This was restored to room temperature, extracted with toluene, and the organic phase was washed with brine, dried with anhydrous magnesium sulfate, and the solvent was evaporated away under reduced pressure. The residue was purified through column chromatography to give the compound 28 (97 g).

[Chem. 60]

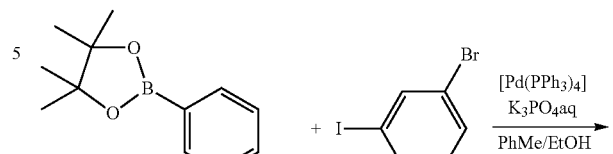

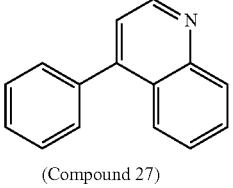

(Compound 27)

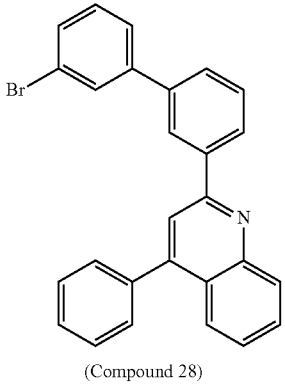

(Compound 28)

Synthesis Example 37: Synthesis Example for Compound 29

In a nitrogen flow, magnesium (turnings) (9.4 g) was put into a reactor, and with stirring, 6-phenyl-1-bromohexane (74.5 g) dissolved in dry diethyl ether (200 mL) was gradually and dropwise added thereto, and thereafter stirred at room temperature for 1 hour. The obtained Grignard reagent solution was dropwise added to a reactor containing the compound 28 (67.4 g), [NiCl₂(dppp)] (4.2 g) and dry diethyl ether (440 mL), in a nitrogen flow at room temperature, and then kept stirred at room temperature for 1 hour. Subsequently, an aqueous solution of ammonium chloride was added thereto to stop the reaction, and then water and methylene chloride were added thereto for liquid separation washing, and thereafter the organic phase was dried with magnesium sulfate. Next, the solvent was removed under reduced pressure. The obtained residue was purified through column chromatography to give the compound 29 (64.5 g).

[Chem. 61]

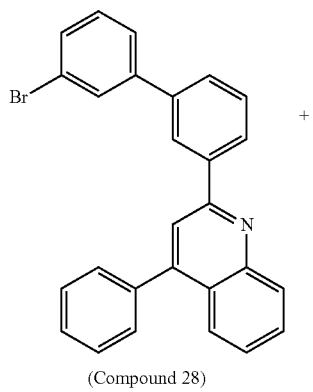

(Compound 28)

+

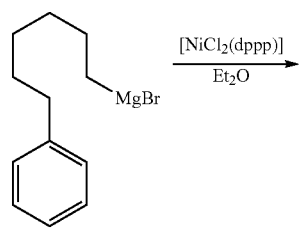

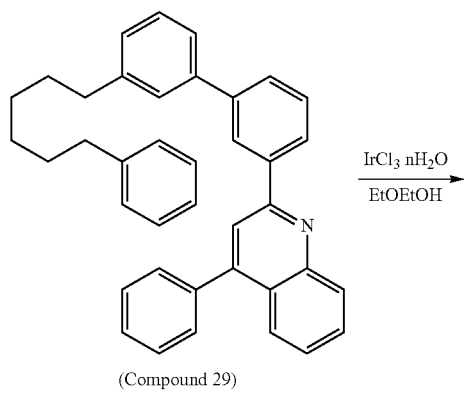

(Compound 29)

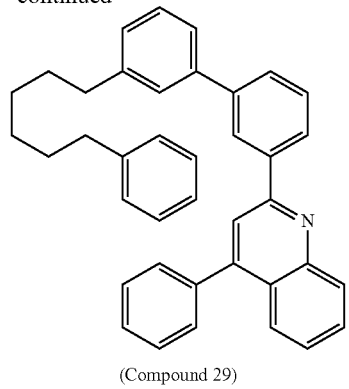

(Compound 29)

Synthesis Example 38: Synthesis Example for Compound 30

Bubbled with nitrogen, 2-ethoxyethanol (115 mL) and water (15 mL) were added to the compound 29 (11.4 g) and IrCl$_3$.n-hydrate (3.59 g) in a nitrogen flow. With the inner temperature kept stepwise elevated up to 100 to 135° C., this was stirred for 11 hours in total. Subsequently, this was extracted with dichloromethane, and the organic phase was washed with water and concentrated under reduced pressure to give the compound 30 as a crude product.

[Chem. 62]

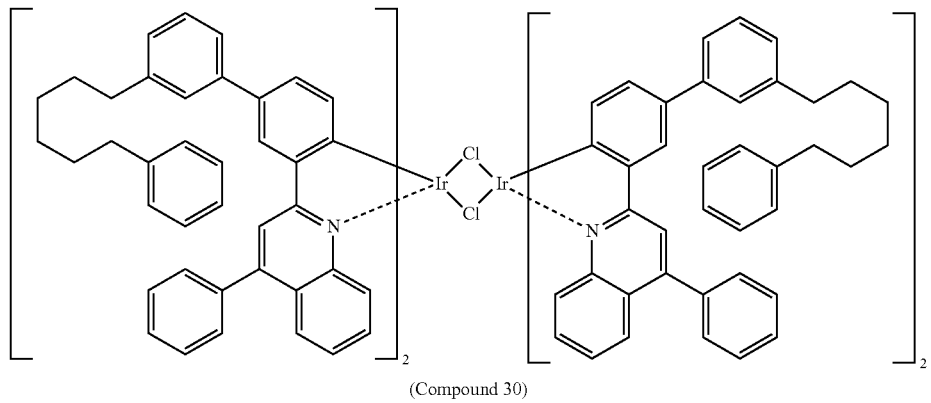

(Compound 30)

Synthesis Example 39: Synthesis Example for Compound 31

In a nitrogen flow, the crude product of compound 30, sodium acetylacetonate (2.43 g) and 2-ethoxyethanol (130 mL) were put into a reactor in that order, and stirred at an inner temperature of 135° C. for 1 hour. Subsequently, this was extracted with dichloromethane, and the organic phase was washed with brine, dried with magnesium sulfate, and concentrated under reduced pressure. Repeatedly the residue was processed through column chromatography and washed with methanol in suspension to give the compound 31 (7.64 g).

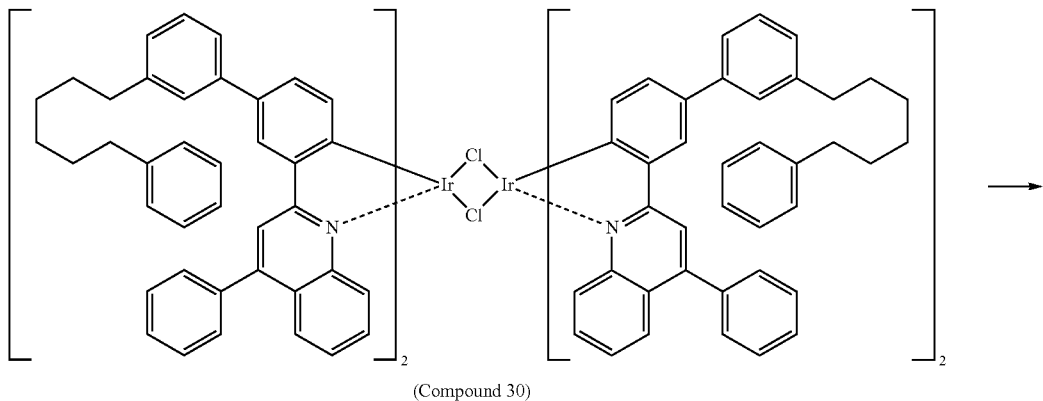

(Compound 30)

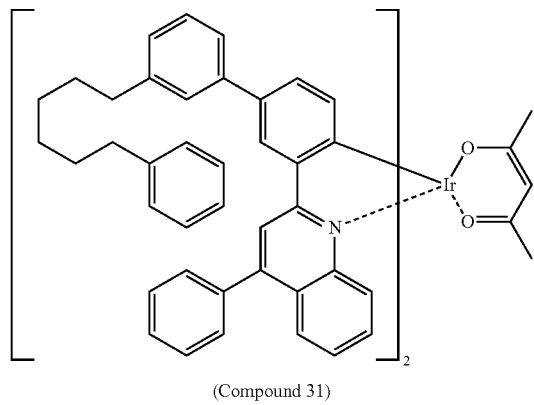

(Compound 31)

Synthesis Example 40: Synthesis Example for Compound D-11

In a nitrogen flow, the compound 31 (7.6 g) and the compound 29 (29.7 g) were stirred in an oil bath at 260 to 270° C. for 18 hours. The residue was purified through column chromatography and reprecipitation to give the compound D-11 (0.4 g).

The compound was mixed in phenylcyclohexane in an amount of 1.5% by weight relative to the latter, and heated up to 120° C., whereupon the compound immediately dissolved to give a homogeneous solution. Subsequently, the solution was stored at room temperature for 2 months, and kept having a homogeneous state.

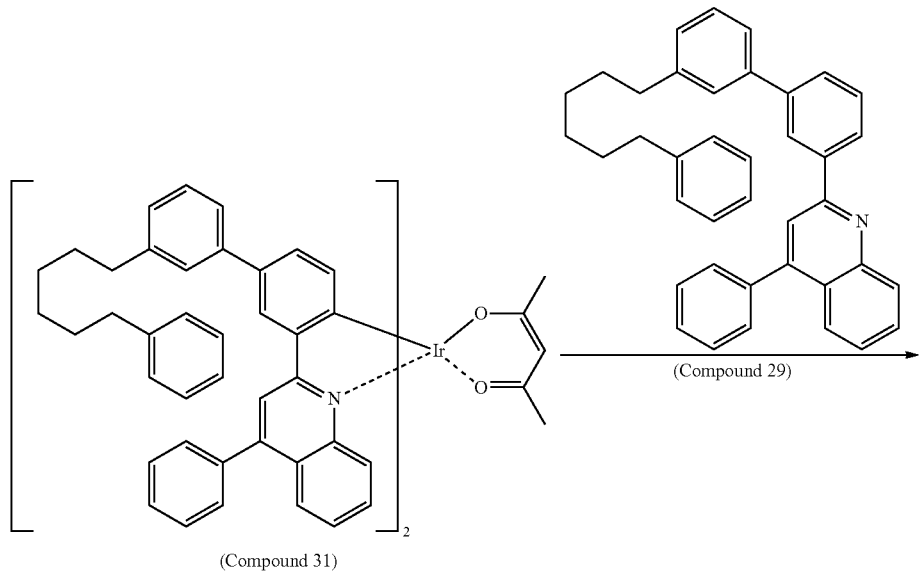

(Compound 29)

(Compound 31)

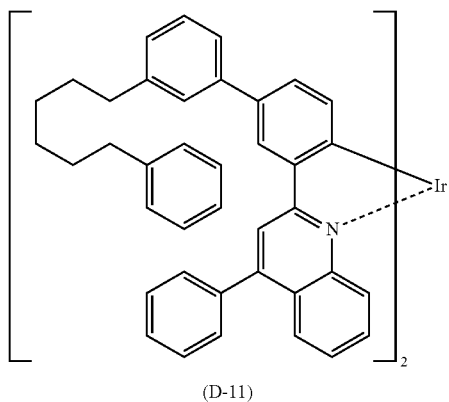

(D-11)

Example 1

[Production of Organic Electroluminescent Element]

An organic electroluminescent element having the configuration shown in FIG. 2 was produced according to the method mentioned below.

On a glass substrate 1 having, as deposited thereon, an indium tin oxide (ITO) transparent conductive film having a thickness of 70 nm (sputtered product, having a sheet resistance of 15Ω), an anode was formed by patterning thereon in stripes each having a width of 2 mm, according to ordinary photolithography combined with hydrochloric acid etching. The thus-patterned ITO substrate was ultrasonically washed with a neutral detergent and then washed with pure water, thereafter dried with compressed nitrogen, and finally washed with UV/ozone.

Next, a hole injection layer was formed according to a wet-process film formation method as mentioned below. An aromatic amino group-having polymer compound of the following formula (PB-1) (weight-average molecular weight: 33000, number-average molecular weight: 25000) and an aromatic amino group-having polymer compound of (PB-2) (weight-average molecular weight: 76000, number-average molecular weight: 40000), and an electron-accepting compound (A-1) having the structural formula mentioned below were used as the materials for forming a hole injection layer, and applied onto the substrate in a mode of spin coating under the condition mentioned below, thereby forming a uniform thin film having a thickness of 40 nm.

The polymer compounds PB-1 and PB-2 were produced with reference to the method disclosed in WO2009/102027.

The numerals in the structural formula PB-1 mentioned below indicate the ratio of the two recurring units each parenthesized by [ ]. Ar in the structural formula PB-2 includes the aryl groups shown on the right side of the structural formula, and the two aryl groups exist in the molar ratio expressed by x.

[Chem. 65]
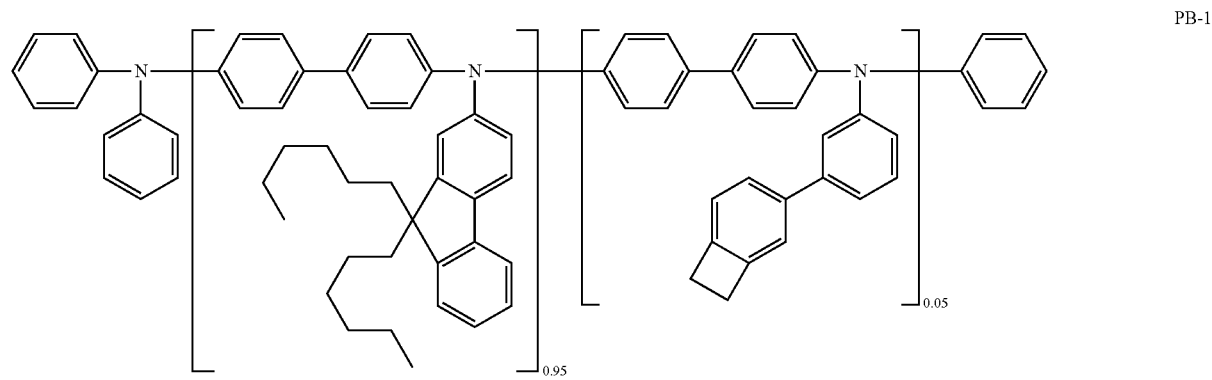
PB-1
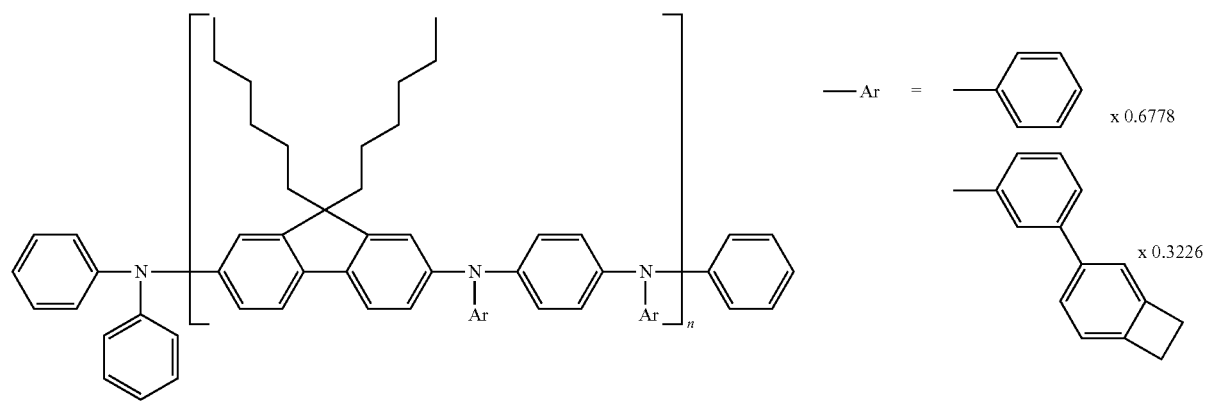
PB-2
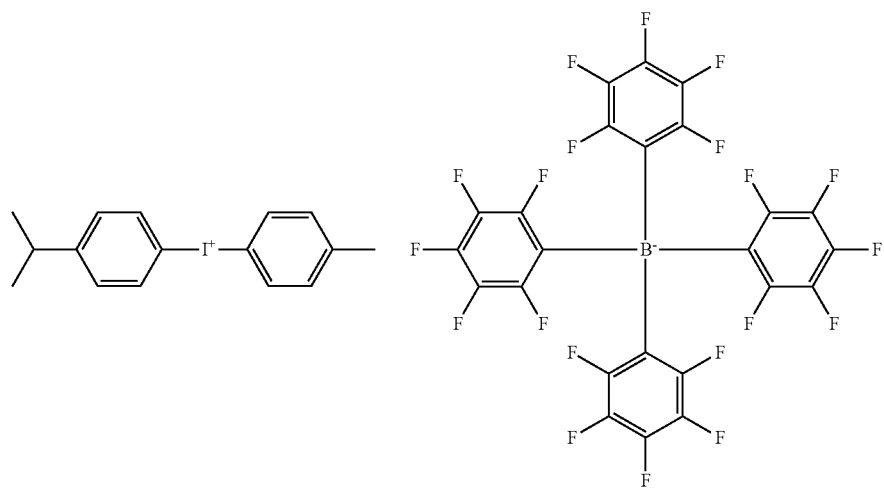
A-1

<Composition for Hole Injection Layer>

| (Solvent) ethyl benzoate (Coating Liquid Concentration) | |
|---|---|
| PB-1 | 0.875% by weight |
| PB-2 | 2.625% by weight |
| A-1 | 0.525% by weight |

<Film Formation Condition>
(Spin Coating Atmosphere): air, 23° C.
(Drying Condition): 230° C.×60 minutes Subsequently, a hole transport layer was formed according to a wet-process film formation method as mentioned below. As a material for the hole transport layer, an aromatic amino group-having polymer compound of a charge-transporting material (PB-3) having a structural formula mentioned below (weight-average molecular weight: 79000, number-average molecular weight: 54000) was dissolved in a solvent of phenylcyclohexane to prepare a composition for an organic electroluminescent element, and the composition for an organic electroluminescent element was used and applied onto the above in a mode of spin coating under the condition mentioned below, thereby forming a thin film having a thickness of 11 nm.

Ar in the structural formula PB-3 includes the two aryl groups shown on the right side of the structural formula, and the two aryl groups exist in the molar ratio expressed by the numerals. The polymer compound PB-3 was produced with reference to the method disclosed in WO2011/099531.

[Chem. 66]

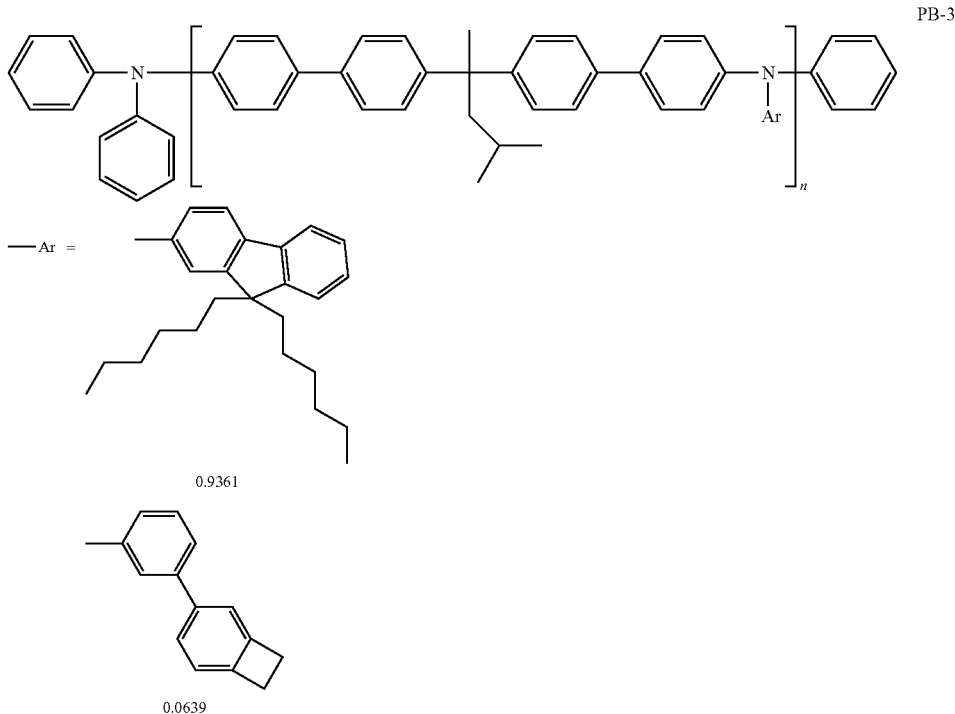

<Composition for Hole Transport Layer>

| (Solvent) phenylcyclohexane (Coating Liquid Concentration) | |
|---|---|
| PB-3 | 1.0% by weight |

<Film Formation Condition>
(Spin Coating Atmosphere): dry nitrogen, 32° C.
(Drying Condition): 230° C.×60 minutes (in dry nitrogen)

Subsequently, for forming a light-emitting layer, an organic compound (HO-1) and an organic compound (HO-2) mentioned below as charge-transporting materials, and an iridium complex compound (D-1) mentioned below as a light-emitting material were used to prepare an iridium complex compound-containing composition, and the composition was applied onto the hole transport layer in a mode of spin coating under the condition mentioned below, thereby forming a light-emitting layer having a thickness of 50 nm.

[Chem. 67]

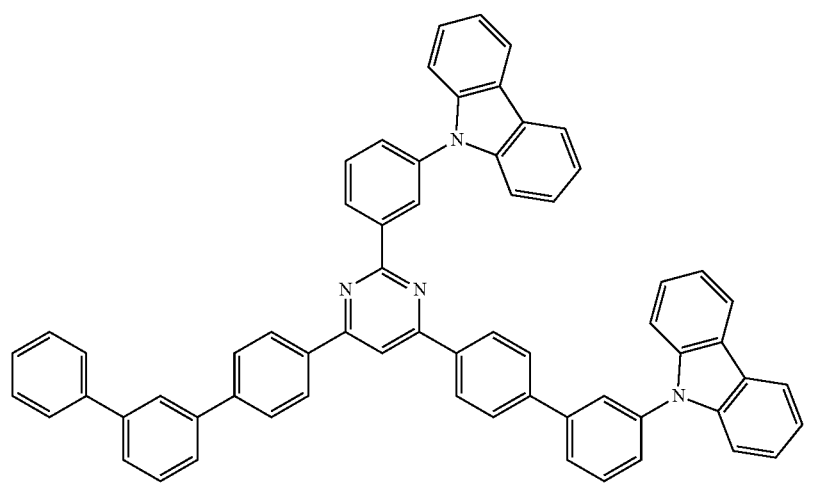

HO-1

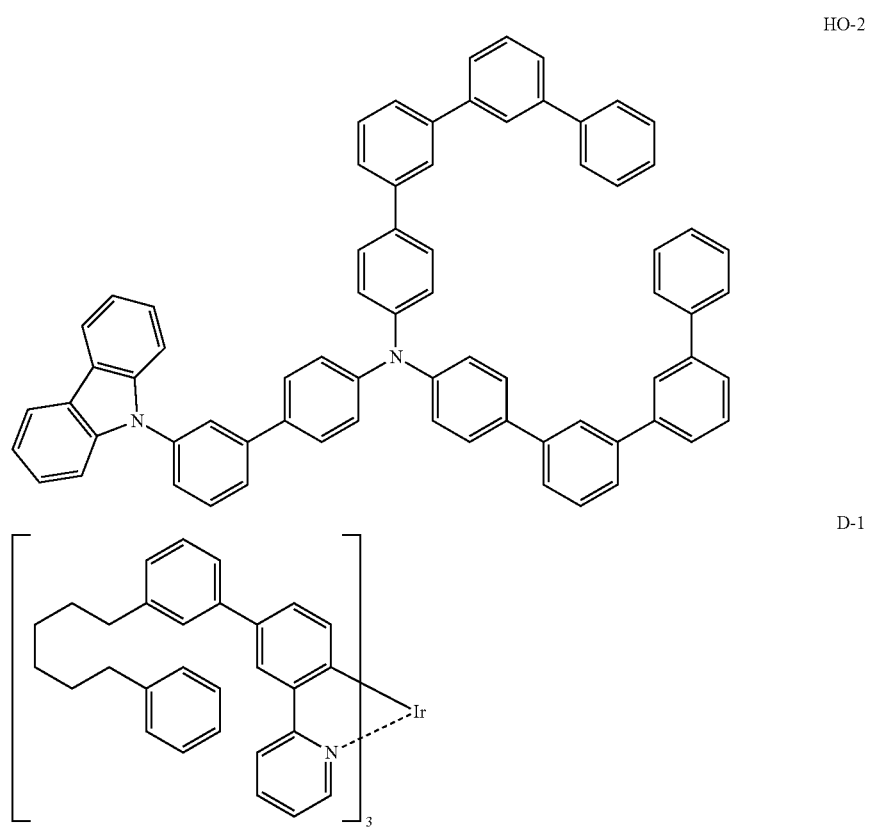

HO-2

D-1

<Composition for Light-Emitting Layer>

| (Solvent) phenylcyclohexane (Coating Liquid Concentration) | |
|---|---|
| HO-1 | 1.2% by weight |
| HO-2 | 3.6% by weight |
| D-1 | 0.48% by weight |

<Spin Coating Condition>

(Spin Coating Atmosphere): dry nitrogen, 35° C.

(Drying Condition): 120° C.×20 minutes (in dry nitrogen)

The substrate was once taken out in air, and then immediately set in the chamber of a vacuum vapor deposition apparatus. The chamber was roughly degassed via a rotary pump, and then depressurized via a cryopump. A vapor deposition mask was arranged on the substrate in a predetermined region thereof, and previously, necessary vapor deposition materials were separately put in individual ceramic crucibles and arranged in the chamber.

Next, as a hole-blocking layer, a compound (HB-1) shown below was layered on the above to have a thickness of 10 nm.

[Chem. 68]

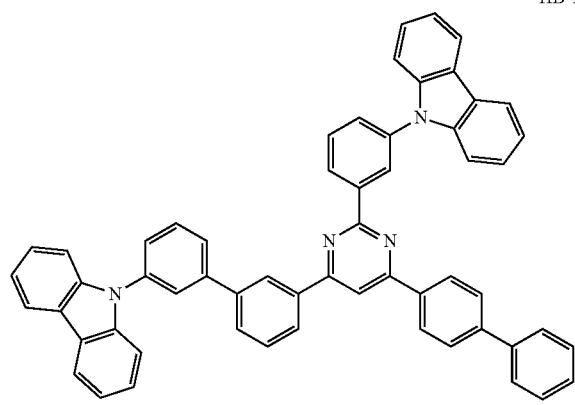

HB-1

Next, on the hole-blocking layer, as an electron transport layer, an aluminium 8-hydroxyquinoline complex (ET-1) shown below was vapor-deposited in the same manner as above, and the layer thickness was 20 nm.

[Chem. 69]

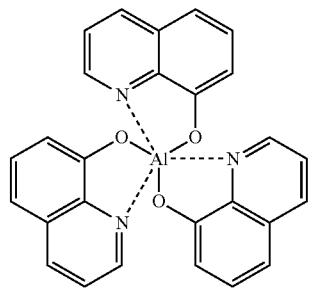

ET-1

Regarding the temperature thereof in vacuum vapor deposition to form the above hole-blocking layer and electron transport layer, the substrate was kept at room temperature.

The element that had been processed for vapor deposition to have up to the electron transport layer was once taken out from the vacuum vapor deposition apparatus into air, and as a mask for cathode deposition, a stripy shadow mask with a stripe width of 2 mm was tightly attached to the element so that the cathode stripes could be orthogonal to the anode ITO stripes, and the element was set in a different vacuum vapor deposition apparatus and, like that for the organic layers, the chamber was degassed to have a vacuum degree of $3.3 \times 10^{-4}$ Pa or less.

Next, as an electron injection layer, a film of lithium fluoride (LiF) was formed to have a thickness of 0.5 nm.

Next, on the electron injection layer, an aluminium layer having a thickness of 80 nm was formed as a cathode. In forming the electron injection layer and the cathode by vapor deposition thereon, the substrate was kept at room temperature.

As in the above, an organic electroluminescent element having a light-emitting surface part in a size of 2 mm×2 mm was obtained.

The maximum wavelength of the light emission spectrum of the element was 520 nm, and this was identified as one from the iridium complex compound (D-1).

Comparative Example 1

An organic electroluminescent element was produced in the same manner as in Example 1, except that the compound D-1 used in forming the light-emitting layer in Example 1 was changed to the compound D-4 represented by the following formula.

Comparative Example 2

An organic electroluminescent element was produced in the same manner as in Example 1, except that the compound D-1 used in forming the light-emitting layer in Example 1 was changed to the compound D-5 represented by the following formula. The compound D-5 was obtained according to the method described in JP-A 2010-202644.

[Chem. 70]

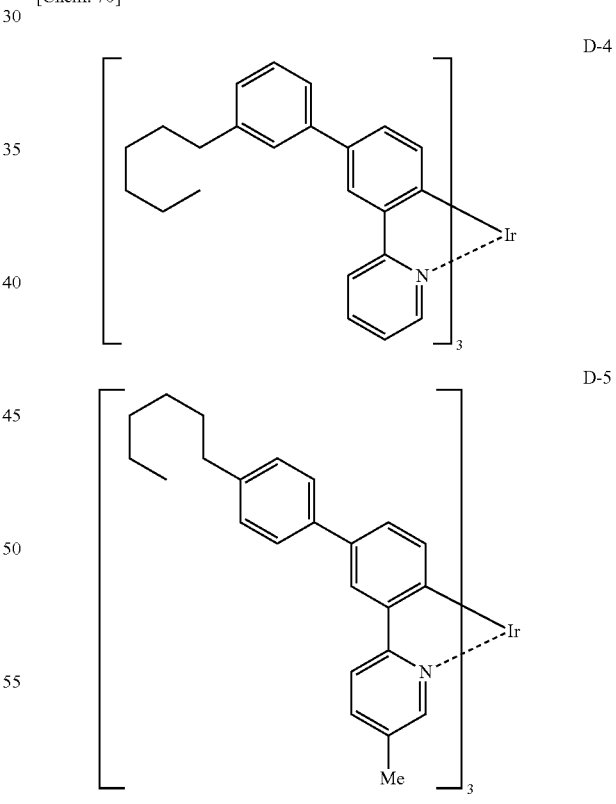

The characteristics of the organic electroluminescent elements produced in Example 1 and Comparative Examples 1 and 2, as well as the test results thereof in a direct current drive test at an initial brightness of 10,000 cd/m$^2$ to count the time taken until brightness reduction to 90% (LT$_{90}$ relative operating lifetime) are shown in Table 1.

TABLE 1

| | Light-Emitting Material | Power Efficiency in Current Application at 10 mA/cm² (relative to the reference value 1 in Example 1) | $LT_{90}$ Relative Operating Lifetime (initial brightness 10000 cd/m², relative to the reference value 1 in Example 1) |
|---|---|---|---|
| Example 1 | D-1 | 1 | 1 |
| Comparative Example 1 | D-4 | 0.92 | 0.65 |
| Comparative Example 2 | D-5 | 0.96 | 0.57 |

As shown in Table 1, it is known that the organic electroluminescent element having the layer containing the iridium complex compound of the present invention has a high power efficiency and has a long operating lifetime.

Comparative Example 3

The compound (D-6) having the following structural formula was tested for the solubility in phenylcyclohexane at room temperature (25° C.), but the solubility thereof was less than 0.2% by weight. Accordingly, using the compound failed in film formation through wet-process film formation, and therefore failed in testing of element characteristics.

[Chem. 71]

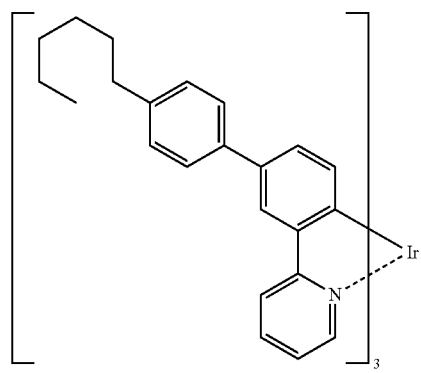

D-6

Comparative Example 4

The compound (D-7) having the following structural formula was tested for the solubility in phenylcyclohexane at room temperature (25° C.), and the compound dissolved in a ratio of 0.85% by weight. The next day, however, the solution precipitated. Accordingly, using the compound failed in film formation through wet-process film formation, and therefore failed in testing of element characteristics.

[Chem. 72]

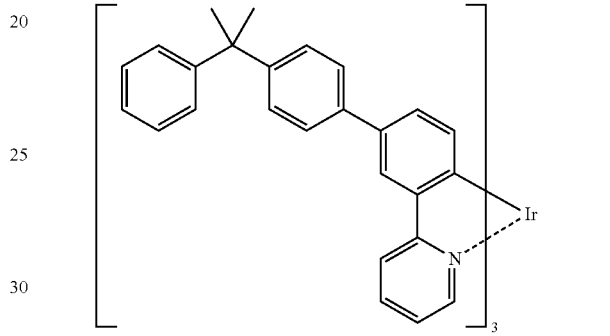

D-7

Example 2

An organic electroluminescent element was produced in the same manner as in Example 1, except that the hole-blocking layer in Example 1 was changed to the following compound (HB-2). The maximum wavelength of the light emission spectrum of the element was 521 nm, and this was identified as one from the iridium complex compound (D-1).

[Chem. 73]

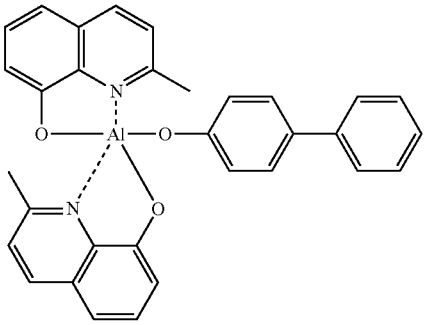

HB-2

Examples 3 and 4, Comparative Example 5

Organic electroluminescent elements were produced in the same manner as in Example 2, except that the light-emitting material used in forming the light-emitting layer in Example 2 was changed to the compound shown in Table 2.

The characteristics of the organic electroluminescent elements produced in Examples 2 to 4 and Comparative Example 5, as well as the test results thereof in a direct current drive test at an initial brightness of 10,000 cd/m² to count the time taken until brightness reduction to 80% ($LT_{80}$ relative operating lifetime) are shown in Table 2.

TABLE 2

| | Light-Emitting Material | Drive Voltage in Current Application at 10 mA/cm² (difference from Example 2) | $LT_{80}$ Relative Operating Lifetime (initial brightness 10000 cd/m², relative to the reference value 1 in Example 2) |
|---|---|---|---|
| Example 2 | D-1 | — | 1 |
| Example 3 | D-2 | −0.04 V | 1.0 |
| Example 4 | D-3 | −0.14 V | 0.89 |
| Comparative Example 5 | D-5 | +0.66 V | 0.39 |

As shown in Table 2, it is known that the organic electroluminescent elements having the layer containing the iridium complex compound of the present invention need a low drive voltage and have a long drive life.

Comparative Example 6

An element was produced in the same manner as in Example 1, except that the charge-transporting material used in forming the light-emitting layer in Example 1 was changed from HO-1 to HO-3 shown below.

The characteristics of the organic electroluminescent element produced in Comparative Example 6, as well as the test result thereof in a direct current drive test at an initial brightness of 10,000 cd/m² to count the time taken until brightness reduction to 90% ($LT_{90}$ relative operating lifetime) are shown in Table 3.

[Chem. 74]

As shown in Table 3, it is known that the organic electroluminescent element having the layer containing the iridium complex compound of the present invention has a high power efficiency and has a long drive life since the element contains a nitrogen-containing aromatic heterocyclic compound as the charge-transporting material therein.

Comparative Example 7

An element was produced in the same manner as in Example 1, except that the charge-transporting materials HO-1 and HO-2 used in forming the light-emitting layer in Example 1 were changed to HO-3 and HO-4 shown below, and that the light-emitting material D-1 was changed to D-8 shown below.

[Chem. 75]

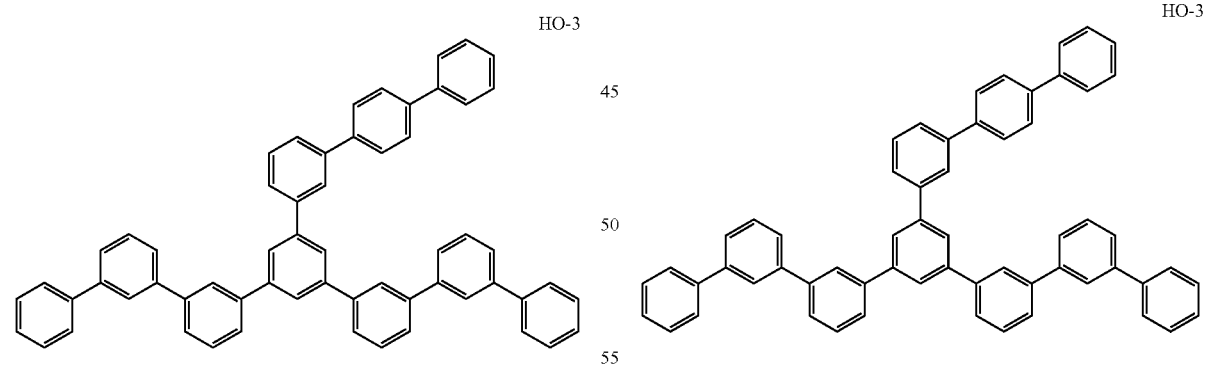

TABLE 3

| | Charge-transporting Material | Power Efficiency in Current Application at 10 mA/cm² (relative to the reference value 1 in Example 1) | $LT_{90}$ Relative Operating Lifetime (initial brightness 10000 cd/m², relative to the reference value 1 in Example 1) |
|---|---|---|---|
| Example 1 | HO-1/HO-2 | 1 | 1 |
| Comparative Example 6 | HO-3/HO-2 | 0.86 | 0.17 |

-continued

HO-4
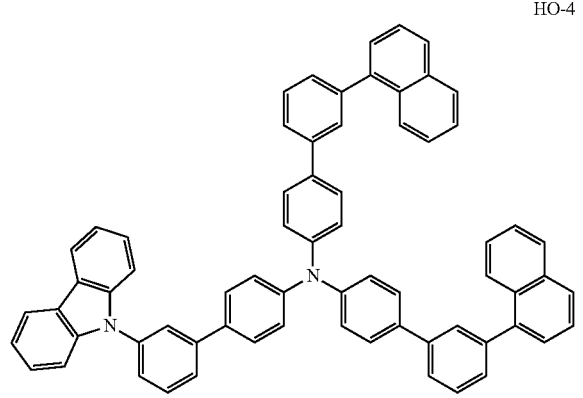

[Chem. 76]

D-9
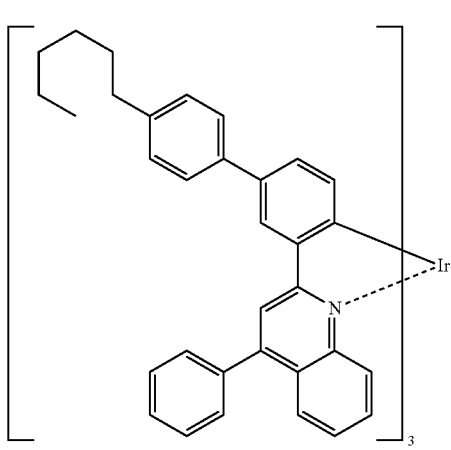

D-8
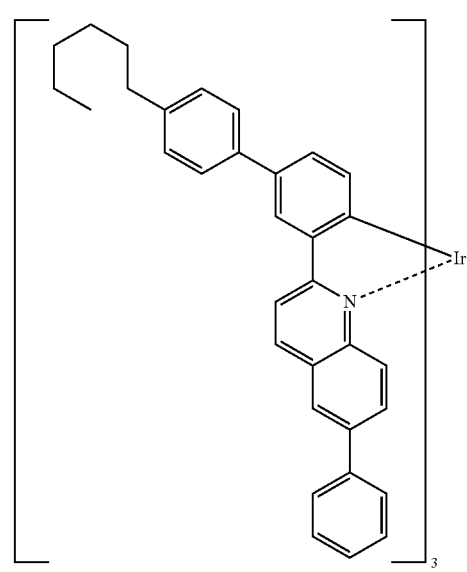

D-10
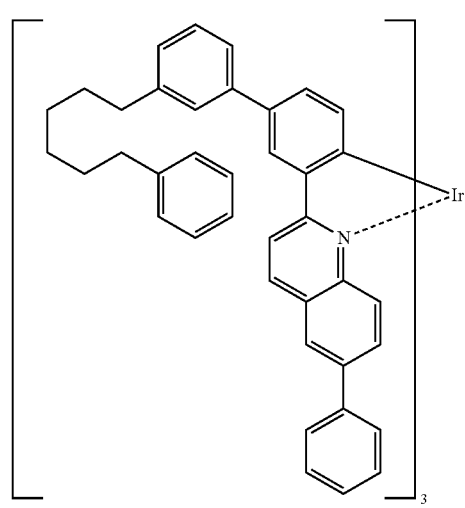

<Composition for Light-Emitting Layer>

| (Solvent) phenylcyclohexane (Coating Liquid Concentration) | |
|---|---|
| HO-3 | 1.2% by weight |
| HO-4 | 3.6% by weight |
| D-8 | 0.336% by weight |

Comparative Example 8, Examples 5 to 8

Elements were produced in the same manner as in Comparative Example 7, except that the light-emitting material and the charge-transporting material used in forming the light-emitting layer in Comparative Example 7 were changed to the combination of the compounds shown in Table 4. Of the compounds given in the column of the light-emitting material in Table 4, the structures of D-9 to D-11 are shown below. Of the compounds given in the column of the charge-transporting material in Table 4, the structures of HO-5 and HO-6 are shown below.

D-11
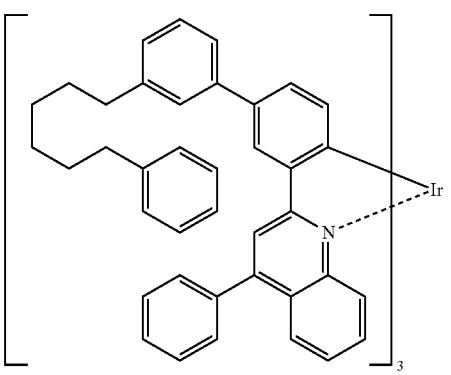

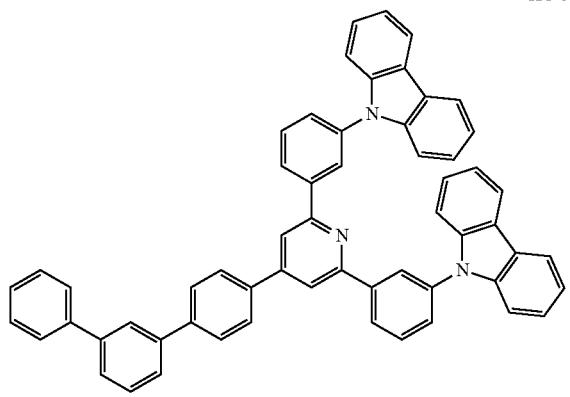

HO-5

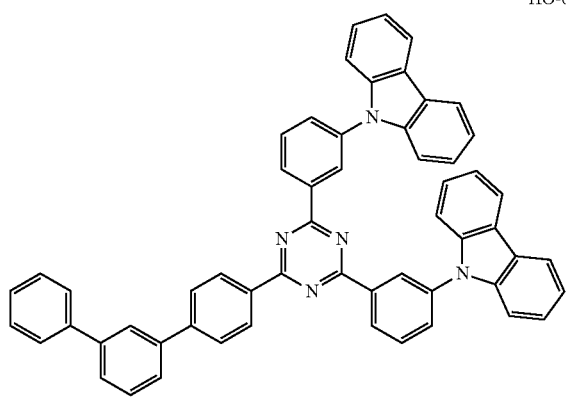

HO-6

The characteristics of the obtained organic electroluminescent elements, as well as the test result thereof in a direct current drive test at an initial brightness of 7,000 cd/m² to count the time taken until brightness reduction to 85% ($LT_{85}$ relative operating lifetime) are shown in Table 4.

TABLE 4

| | Light-Emitting Material | Charge-Transporting Material | Power Efficiency in Current Application at 10 mA/cm² (relative to the reference value 1 in Comparative Example 7) | $LT_{85}$ Relative Operating Lifetime (initial brightness 7000 cd/m², relative to the reference value 1 in Reference Example 7) |
|---|---|---|---|---|
| Comparative Example 7 | D-8 | HO-3/HO-4 | 1 | 1 |
| Comparative Example 8 | D-9 | HO-3/HO-4 | 0.89 | 1.1 |
| Example 5 | D-10 | HO-3/HO-4 | 1.25 | 1.2 |
| Example 6 | D-11 | HO-3/HO-4 | 1.16 | 1.4 |
| Example 7 | D-11 | HO-5/HO-4 | 1.23 | 1.4 |
| Example 8 | D-11 | HO-6/HO-4 | 1.46 | 3.6 |

As shown in Table 4, it is known that the organic electroluminescent elements having the layer containing the organic metal complex of the present invention have a high power efficiency and have a long operating lifetime. In addition, it is also known that the charge-transporting material to be used in the elements preferably contains a nitrogen-containing aromatic heterocyclic compound.

While the present invention has been described in detail with reference to specific embodiments thereof, it will be apparent to one skilled in the art that various changes and modifications can be made therein without departing from the spirit and scope thereof. The present application is based on a Japanese patent application filed on Jan. 13, 2012 (Application No. 2012-005118) and a Japanese patent application filed on Sep. 14, 2012 (Application No. 2012-202908), the contents of which are incorporated herein by reference.

REFERENCE SIGNS LIST

1 Substrate
2 Anode
3 Hole Injection Layer
4 Hole Transport Layer
5 Light-Emitting Layer
6 Hole-Blocking Layer
7 Electron Transport Layer
8 Electron Injection Layer
9 Cathode

The invention claimed is:

1. An iridium complex compound represented by the following formula (1):

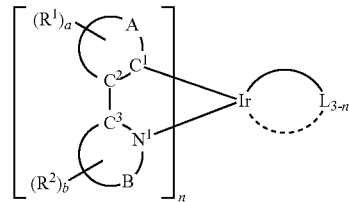

(1)

in the formula (1), the ring A represents a 6-membered or 5-membered aromatic hydrocarbon ring, containing the carbon atoms $C^1$ and $C^2$ or a 6-membered or 5-membered heteroaromatic ring containing the carbon atoms $C^1$ and $C^2$, the ring B represents a 6-membered or 5-membered nitrogen-containing heteroaromatic ring containing the carbon atom $C^3$ and the nitrogen atom $N^1$; L represents an organic ligand; a and b each independently indicate an integer of from 1 to 4; n indicates an integer of from 1 to 3;

$R^1$ and $R^2$ each represent a substituent bonding to ring A and ring B, respectively, multiple $R^1$s and $R^2$s each are the same or different, and $R^1$ and $R^2$ represents a structure of formula (2) or any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero) arylamino group having from 3 to 20 carbon atoms, or a (hetero)aryl group having from 3 to 20 carbon atoms; these groups are optionally substituted with an atom or group selected from the group consisting of a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero) aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, and a (hetero)aryl group having from 3 to 20 carbon atoms;

when a is 2 or more and multiple R's neighbor to each other, then the neighboring $R^1$s may bond directly, or may bond via an alkylene group having from 3 to 12 carbon atoms, an alkenylene group having from 3 to 12 carbon atoms, or an arylene group having from 6 to 12 carbon atoms thereby to further form a ring; when b is 2 or more and multiple $R^2$s neighbor to each other, then the neighboring $R^2$s may bond directly, or may bond via an alkylene group having from 3 to 12 carbon atoms, an alkenylene group having from 3 to 12 carbon atoms, or an arylene group having from 6 to 12 carbon atoms thereby to further form a ring; $R^1$ and $R^2$ may bond directly, or may bond via an alkylene group having from 3 to 12 carbon atoms, an alkenylene group having from 3 to 12 carbon atoms, or an arylene group having from 6 to 12 carbon atoms thereby to further form a ring; the ring formed by bonding of $R^1$s, $R^2$s or $R^1$ and $R^2$ is optionally substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero) arylsilyl group having from 3 to 20 carbon atoms, an alkylcarbonyl group having from 2 to 20 carbon atoms, a (hetero)arylcarbonyl group having from 4 to 20 carbon atoms, an alkyl amino group having from 2 to 20 carbon atoms, a (hetero)aryl amino group having from 3 to 20 carbon atoms, or a (hetero)aryl group having from 3 to 20 carbon atoms;

provided that at least one of $R^1$ is represented by the structure of formula (2):

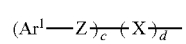

(2)

in the formula (2), multiple Xs are the same or different, and X represents a (hetero)arylene group having from 6 to 20 carbon atoms, multiple $Ar^1$s are the same or different, and $Ar^1$ represents a (hetero)aryl group having from 3 to 20 carbon atoms; wherein these groups are optionally substituted with an atom or group selected from the group consisting of a fluorine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero) arylamino group having from 3 to 20 carbon atoms, and a (hetero)aryl group having from 3 to 20 carbon atoms; Z is represented by the following formula (3); c indicates an integer of 1; d indicates an integer of from 1 to 3:

(3)

in the formula (3), multiple R's are the same or different, and R' represents a hydrogen atom, a fluorine atom, a chlorine atom, a bromine atom, an alkyl group having from 1 to 20 carbon atoms, an alkoxy group having from 1 to 20 carbon atoms, a (hetero)aryloxy group having from 3 to 20 carbon atoms, or a (hetero)aryl group having from 3 to 20 carbon atoms; r indicates an integer of from 2 to 20.

2. The iridium complex compound according to claim 1, wherein in the formula (1), at least one of the substituents $R^2$s bonding to the ring B is represented by the formula (2).

3. The iridium complex compound according to claim 1, wherein in the formula (1), the ring A is a benzene ring or a pyridine ring.

4. The iridium complex compound according to claim 1, which is represented by the following formula (1-1):

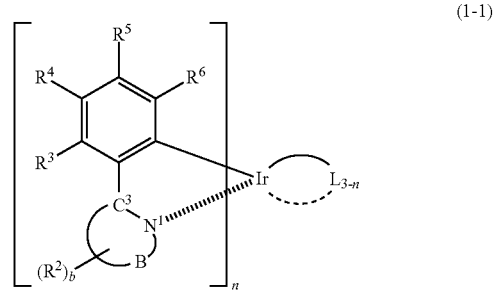

(1-1)

in the formula (1-1), the ring B, $R^2$, L, b and n each have the same meanings as in the formula (1);

$R^3$ to $R^6$ each are the same or different, and represent a structure of formula (2) or any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms; wherein these groups are optionally substituted with an atom or group selected from the group consisting of a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, and a (hetero)aryl group having from 3 to 20 carbon atoms;

regarding $R^3$ to $R^6$, the neighboring $R^3$s to $R^6$s may bond directly, or may bond via an alkylene group having from 3 to 12 carbon atoms, an alkenylene group having from 3 to 12 carbon atoms, or an arylene group having from 6 to 12 carbon atoms thereby to form a ring; wherein these rings are optionally substituted with an atom or group selected from the group consisting of a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkyl silyl group having from 1 to 20 carbon atoms, a (hetero)aryl silyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, and a (hetero)aryl group having from 3 to 20 carbon atoms;

provided that the iridium complex compound represented by the formula (1-1) has at least one group represented by the formula (2) at $R^3$ to $R^6$.

5. The iridium complex compound according to claim 4, wherein $R^4$ is represented by the formula (2).

6. The iridium complex compound according to claim 4, wherein $R^5$ is represented by the formula (2).

7. The iridium complex compound according to claim 1, wherein the ring B is a pyridine ring, a pyrazine ring, a pyrimidine ring, an imidazole ring, an oxazole ring or a thiazole ring.

8. The iridium complex compound according to claim 1, wherein the ring B is a pyridine ring.

9. The iridium complex compound according to claim 1, wherein the ring B is a pyrazine ring.

10. The iridium complex compound according to claim 1, wherein the ring B is a pyrimidine ring.

11. The iridium complex compound according to claim 1, wherein the ring B is an imidazole ring.

12. The iridium complex compound according to claim 1, wherein in the formula (2), $Ar^1$ is an aromatic hydrocarbon group having from 6 to 20 carbon atoms.

13. A light-emitting material comprising the iridium complex compound according to claim 1.

14. A composition comprising the iridium complex compound according to claim 1 and a solvent.

15. An organic electroluminescent element comprising an anode, a cathode and at least one organic layer between the anode and the cathode, wherein at least one layer of the organic layers is a layer formed using the composition according to claim 14.

16. An organic electroluminescent element comprising an anode, a cathode and at least one organic layer between the anode and the cathode, wherein at least one layer of the organic layers contains the iridium complex compound according to claim 1.

17. The organic electroluminescent element according to claim 16, wherein the organic layer further contains a nitrogen-containing aromatic heterocyclic compound as a charge transport material.

18. A display using the electroluminescent element according to claim 16.

19. A lighting using the electroluminescent element according to claim 16.

20. An iridium complex compound represented by the following formula (1):

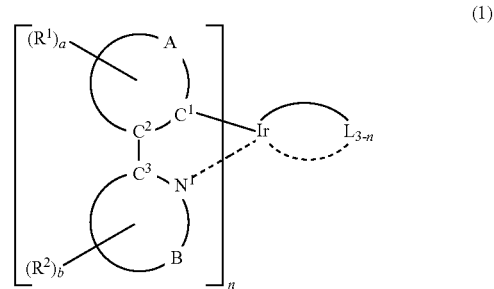

in the formula (1), the ring A represents a 6-membered or 5-membered aromatic hydrocarbon ring, containing the carbon atoms $C^1$ and $C^2$ or a 6-membered or 5-membered heteroaromatic ring containing the carbon atoms $C^1$ and $C^2$, the ring B represents a 6-membered or 5-membered nitrogen-containing heteroaromatic ring containing the carbon atom $C^3$ and the nitrogen atom $N^1$; L represents an organic ligand; a and b each independently indicate an integer of from 1 to 4; n indicates an integer of from 1 to 3;

$R^1$ and $R^2$ each represent a substituent bonding to ring A and ring B, respectively, multiple $R^1$s and $R^2$s each are the same or different, and $R^1$ and $R^2$ represents a structure of formula (2) or any of a hydrogen atom, a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms; these groups are optionally substituted with an atom or group selected from the group consisting of a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, and a (hetero)aryl group having from 3 to 20 carbon atoms;

when a is 2 or more and multiple $R^1$s neighbor to each other, then the neighboring $R^1$s may bond directly, or may bond via an alkylene group having from 3 to 12 carbon atoms, an alkenylene group having from 3 to 12 carbon atoms, or an arylene group having from 6 to 12 carbon atoms thereby to further form a ring; when b is 2 or more and multiple $R^2$s neighbor to each other, then the neighboring $R^2$s may bond directly, or may bond via an alkylene group having from 3 to 12 carbon atoms, an alkenylene group having from 3 to 12 carbon atoms, or an arylene group having from 6 to 12 carbon atoms thereby to further form a ring; $R^1$ and $R^2$ may bond directly, or may bond via an alkylene group having from 3 to 12 carbon atoms, an alkenylene group having from 3 to 12 carbon atoms, or an arylene group having from 6 to 12 carbon atoms thereby to further form a ring; the ring formed by bonding of $R^1$s, $R^2$s or $R^1$ and $R^2$ is optionally substituted with a fluorine atom, a chlorine atom, a bromine atom, an alkyl group having from 1 to 20 carbon atoms, a (hetero)aralkyl group having from 7 to 40 carbon atoms, an alkoxy group having from 1 to 20 carbon atoms, a (hetero)aryloxy group having from 3 to 20 carbon atoms, an alkylsilyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, or a (hetero)aryl group having from 3 to 20 carbon atoms;

provided that at least one of $R^1$ is represented by the structure of formula (2):

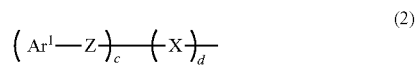

(2)

in the formula (2), multiple Xs are the same or different, and X represents a (hetero)arylene group having from 6 to 20 carbon atoms, multiple $Ar^1$s are the same or different, and $Ar^1$ represents a (hetero)aryl group having from 3 to 20 carbon atoms; wherein these groups are optionally substituted with an atom or group selected from the group consisting of a fluorine atom, an alkyl group having from 1 to 20 carbon atoms, an alkoxy group having from 1 to 20 carbon atoms, a (hetero)aryloxy group having from 3 to 20 carbon atoms, an alkyl silyl group having from 1 to 20 carbon atoms, a (hetero)arylsilyl group having from 3 to 20 carbon atoms, an alkylcarbonyl group having from 2 to 20 carbon atoms, a (hetero)arylcarbonyl group having from 4 to 20 carbon atoms, an alkylamino group having from 2 to 20 carbon atoms, a (hetero)arylamino group having from 3 to 20 carbon atoms, and a (hetero)aryl group having from 3 to 20 carbon atoms; Z is represented by the following formula (3); c indicates an integer of 1; d indicates an integer of from 1 to 3:

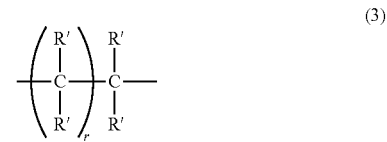

(3)

in the formula (3), multiple R's are the same or different, and R' represents a hydrogen atom, a fluorine atom, a chlorine atom, a bromine atom, an alkyl group having from 1 to 20 carbon atoms, an alkoxy group having from 1 to 20 carbon atoms, a (hetero)aryloxy group having from 3 to 20 carbon atoms, or a (hetero)aryl group having from 3 to 20 carbon atoms; r indicates an integer of from 1 to 20.

* * * * *